US006531586B1

(12) United States Patent
St. George-Hyslop et al.

(10) Patent No.: US 6,531,586 B1
(45) Date of Patent: Mar. 11, 2003

(54) GENETIC SEQUENCES RELATED TO ALZHEIMER'S DISEASE

(75) Inventors: Peter H. St. George-Hyslop, Toronto (CA); Johanna M. Rommens, Toronto (CA); Paul E. Fraser, Toronto (CA)

(73) Assignees: The Hospital for Sick Children, Toronto (CA); HSC Research and Development Limited Partnership, Toronto (CA); The Governing Council of the University of Toronto, Toronto (CA)

(*) Notice: Subject to any disclaimer, the term of this patent is extended or adjusted under 35 U.S.C. 154(b) by 0 days.

(21) Appl. No.: 08/431,048

(22) Filed: Apr. 28, 1995

(51) Int. Cl.[7] .......................... C12N 15/11; C12N 15/63; C12N 15/85; C07H 21/04
(52) U.S. Cl. ................. 536/23.5; 536/23.1; 435/320.1; 435/325; 435/69.1
(58) Field of Search ......................... 435/6, 69.1, 172.1, 435/172.3, 320.1, 325, 375, 252.3, 254.11; 800/2, DIG. 1, DIG. 2; 536/23.5

(56) References Cited

U.S. PATENT DOCUMENTS

| 5,297,562 A | 3/1994 | Potter ........................... 128/898 |
| 5,545,808 A | 8/1996 | Hew et al. ...................... 800/2 |
| 5,668,006 A | * 9/1997 | Hadcock et al. .......... 435/252.3 |

FOREIGN PATENT DOCUMENTS

| CA | 2054302 | 4/1992 |
| CA | 2071105 | 12/1992 |
| CA | 2096911 | 11/1993 |
| WO | 94/00569 | 1/1994 |
| WO | 94/23049 | 10/1994 |
| WO | WO 97/03086 | 1/1997 |
| WO | WO 97/03192 | 1/1997 |
| WO | WO 97/03999 | 2/1997 |

OTHER PUBLICATIONS

Taniguchi et al., "Cloning of the cDNA encoding rat Presenilin–1," Gene, 186:1, 73–75 (1997).
Citron et al., "Mutant Presenilins of Alzheimer's Disease Increase Production of 42–residue Amyloid β–protein in Both Transfected Cells and Transgenic Mice," Nat. Med., 3:67–72 (1997).
Mullins et al., "Transgenesis in Nonmurine Species," Hypertension, vol. 22(4): 630–633 (1993).
Pursel et al., "Genetic Engineering of Livestock," Science, 244: 1281–1288 (1989).
Salter et al., "Transgenic Chickens: Insertion of Retroviral Genes into the Chicken Germ Line." Virology, 157: 236–240 (1987).
Felsenstein etal. (1995) Alzheimer's Parkenson's Diseases, I.Hanin, ed. Plenum Press NY, p. 401–409.*
Selkoe (1991) Nature 354, 432–433.*
Lannfelt etal. (1993) Behav. Brain Res. 5–7, 207–213.*
Oster–Granite (1996) J. Neuroscience 16, 6732–6741.*
Kappell et al (1992) Current Opinion in Biotechnology 3, 548–553.*
Wall (1996) Theriogenology 45, 57–68.*
Mullins et al (1996) Journal of Clinical Investigation 98, S37–S40.*
(Seamark (1994) Reproductive Fertility and Development 6, 653–657.*
Strojek and Wagner (1988) Genetic Engineering 10, 221–246.*
(Houdebine (1994) Journal of Biotechnology 34, 269–287.*
Li et al., "Identification and expression analysis of a potential familial Alzheimer disease gene on chromosome 1 related to AD3," Proc. Natl. Acad. Sci., USA, 92:12180–4 (1995).
Murrell et al., "A Mutation in the Amyloid Precursor Protein Associated with Hereditary Alzheimer's Disease," Science, 254:97–99 (1991).
Yamada et al., "Complementary DNA for the Mouse Homolog of the Human Amyloid Beta Protein Precursor," Biochem. Biophys. Res. Comm. 149(2):665–71 (1987).
L'Hernault et al., "Mutation of a Putative Sperm Membrane Protein but not Its Associated Meiotic Divisions," J. Cell Biol. 119:55–68 (1992).
Johansson, E., et al., The Journal of Biological Chemistry, 270(35):20615–20620 (1995).
Pawlak, A., et al., EMBL Sequence Data Library, Dec. 20, 1994,Accession No. T18858.
Auffray, C., et al., EMBL Sequence Data Library, Feb. 17, 1995, Accession No. F08730.
Zahraoui, A., et al., EMBL Sequence Data Library, Jul. 22, 1994, Accession No. X56740.
Drivas, G.T., et al., EMBL Sequence Data Library, Feb. 19, 1991, Accession No. X53143.
Chambon, P., et al., EMBL Sequence Data Library, Feb. 7, 1992, Accession No. M84820.
Fleischhauer, K., et al., EMBL Sequence Data Library, Mar. 31, 1992, Accession No. X63522.
Yu, V.C., et al., EMBL Sequence Data Library, Dec. 10, 1991, Accession No. M81766.
Sevigny, G., et al., EMBL Sequence Data Library, Jan. 7, 1995, Accession No. U17104.
Walkley, N.A., et al., EMBL Sequence Data Library, Jan. 1, 1994, Accession No. X74801.
Hillier, L., et al., EMBL Sequence Data Library, Apr. 22, 1995, Accession No. R12984.
Fujiwara, T., et al., EMBL Sequence Data Library, Aug. 25, 1995, Accession No. D55326.

(List continued on next page.)

Primary Examiner—Michael C. Wilson
(74) Attorney, Agent, or Firm—Darby & Darby

(57) ABSTRACT

The present invention relates to the identification, isolation and cloning of a mammalian polynucleotide which encodes a Alzheimer's related membrane protein (ARMP). The invention also contemplates mutant polynucleotides and polynucleotides that encode ARMP homologs. Vectors encoding the protein and host cells transfected with the vector are further contemplated by the present invention.

46 Claims, 6 Drawing Sheets

OTHER PUBLICATIONS

Hillier, L., et al., EMBL Sequence Data Library, Mar. 6, 1995, Accession No. T64843.

Chartier–Harlin, et al., "Early onset Alzheimer's disease caused by mutations at codon 717 of the β–amyloid precursor protein gene," *Nature*, vol. 353:844–846 (1991).

Foncin, et al., "Alzheimer's Presenile dementia transmitted in an extended kindred," *Rev. Neurol (Paris)*, vol. 141:194–202 (1985).

Goate, et al., "Segregation of a missense mutation in the amyloid precursor protein gene with familial Alzheimer's disease," *Nature*, vol. 349:704–706 (1991).

Goudsmit, et al., "Familial Alzheimer's Disease in two kindreds of the same geographic and ethnic origin: a clinical and genetic study," *J. Neurol. Sci.*, vol. 49:79–89 (1981).

Gyapay, et al., "The 1993–94 Genethon human genetic linkage map," *Nature Genetics*, vol. 7:246–311 (1994).

Karlinsky, et al., "Molecular and prospective phenotypic characterization of a pedigree with familial Alzheimer's disease and a missense mutation in codon 717 of the β–amyloid precursor protein (APP) gene," *Neurology*, vol. 42:1445–1453 (1992).

Katzman, R., "Alzheimer's Disease," *N.Eng.J.Med.*, vol. 314:964–973, (1986).

Mullan, et al., "A pathogenic mutation for probable Alzheimer's disease in the APP gene at the N–terminus of β–amyloid," *Nature Genetics*, vol. 1:345–347 (1992).

Mullan, et al., "A locus for familial early–onset Alzheimer's disease on the long arm of chromosome 14, proximal to the α1–antichymotrypsin gene," *Nature Genetics*, vol. 2:340–342 (1992).

Murrell, et al., "A mutation in the amyloid precursor protein associated with hereditary Alzheimer's Disease," *Science*, vol. 254:97–99 (1991).

Nee, et al., "A family with histologically confirmed Alzheimer's Disease," *Arch Neurol*, vol. 40:203–208 (1983).

Pericak–Vance, et al., "Genetic linkage studies in Alzheimer's Disease families," *Exp. Neurol*, vol. 102:271–279 (1988).

Rogaev, et al., "Analysis of the c–FOS gene on chromosome 14 and the promoter of the amyloid precursor protein gene in familial Alzheimer's disease," *Neurology*, vol. 43:2275–2279 (1993).

Rommens, et al., "A transcription map of the region containing the Huntington disease gene," *Hum. Molec. Genet.*, vol. 2:901–907 (1993).

St. George–Hyslop, et al., "Genetic linkage studies suggest that Alzheimer's disease is not a single homogeneous disorder," *Nature*, vol. 347:194–197 (1990).

St. George–Hyslop, et al., "Genetic evidence for a novel familial Alzheimer's disease locus on chromosome 14," *Nature Genetics*, vol: 2:330–334 (1992).

St. George–Hyslop, et al., "Alzheimer's Disease and Possible Gene Interaction," *Science*, vol. 263:537 (1994).

Saunders, et al., "Association of apolipoprotein E allele e4 with the late–onset familial and sporadic Alzheimer's disease," *Neurology*, vol. 43:1467–1472 (1993).

Schellenberg, et al., "Genetic Linkage Evidence for a Familial Alzheimer's Disease Locus on Chromosome 14," *Science*, vol. 258:668–670 (1992).

Schellenberg, et al., "Chromosome 14 and Late–Onset Familial Alzheimer Disease (FAD)," *Am. J. Hum. Genet.*, vol. 53:619–628 (1993).

Strittmatter, et al., "Apolipoprotein E: high avidity binding to β–amyloid and increased frequency of type 4 allele in late–onset familial Alzheimer's disease," *Proc. Nat'l. Acad. Sci. USA*, vol. 90:1977–1981 (1993).

Van Broeckhoven, et al., "Mapping of a gene predisposing to early–onset Alzheimer's disease to chromosome 14q24.3," *Nature Genetics*, vol. 2:335–339 (1992).

Wong, et al., "Mutation of the gene for the human lysosomal serine protease Cathepsin G is not the cause of aberrant APP processing in familial Alzheimer disease," *Neurosci. Lett*, vol. 152:96–98 (1993).

\* cited by examiner

Met 146 Lev

Leu 286 Val

Cys    410    Tyr

US 6,531,586 B1

GENETIC SEQUENCES RELATED TO ALZHEIMER'S DISEASE

FIELD OF THE INVENTION

The present invention relates generally to the field of neurological and physiological disfunctions associated with Alzheimer's Disease. More particularly, the invention is concerned with the identification, isolation and cloning of the gene which when mutated is associated with Alzheimer's Disease as well as its transcript, gene products and associated sequence information and neighbouring genes. The present invention also relates to methods of diagnosing for and detection of carriers of the gene, Alzheimer Disease diagnosis, gene therapy using recombinant technologies and therapy using the information derived from the DNA, protein, and the metabolic function of the protein.

BACKGROUND OF THE INVENTION

In order to facilitate reference to various journal articles, a listing of the articles is provided at the end of this specification.

Alzheimer's Disease (AD) is a degenerative disorder of the human central nervous system characterized by progressive memory impairment and cognitive and intellectual decline during mid to late adult life (Katzman, 1986). The disease is accompanied by a constellation of neuropathologic features principal amongst which are the presence of extracellular amyloid or senile plaques and the neurofibrillary degeneration of neurons. The etiology of this disease is complex, although in some families it appears to be inherited as an autosomal dominant trait. However, even amongst these inherited forms of AD, there are at least three different genes which confer inherited susceptibility to this disease (St George-Hyslop at al., 1990). The ε4 (Cys112Arg) allelic polymorphism of the Apolipoprotein E (ApoE) gene has been associated with AD in a significant proportion of cases with onset late in life (Saunders et al., 1993; Strittmatter et al., 1993). Similarly, a very small proportion of familial cases with onset before age 65 years have been associated with mutations in the β-amyloid precursor protein (APP) gene (Chartier-Harlin et al., 1991; Goate et al., 1991; Murrell et al., 1991; Karlinsky at al., 1992; Mullan et al., 1992). A third locus (AD3) associated with a larger proportion of cases with early onset AD has recently been mapped to chromosome 14q24.3 (Schellenberg at al., 1992; St George-Hyslop et al., 1992; Van Broeckhoven et al., 1992).

Although chromosome 14q carries several genes which could be regarded as candidate genes for the site of mutations associated with AD3 (e.g. cFOS, alpha-1-antichymotrypsin, and cathepsin G), most of these candidate genes have been excluded on the basis of their physical location outside the AD3 region and/or the absence of mutations in their respective open reading frames (Schellenberg, G D et al., 1992; Van Broeckhoven, C et al., 1992; Rogaev et al., 1993; Wong et al., 1993).

There have been several developments and commercial directions in respect of treatment of Alzheimer's Disease and diagnosis thereof. Published PCT application WO 94 23049 describes transfection of high molecular weight YAC DNA into specific mouse cells. This method is used to analyze large gene complexes, for example the transgenic mice may have increased amyloid precursor protein gene dosage, which mimics the trisomic condition that prevails in Downs Syndrome and the generation of animal models with β-amyloidosis prevalent in individuals with Alzheimer's Disease. Published international application WO 94 00569 describes transgenic non-human animals harbouring large trans genes such as the trans gene comprising a human amyloid precursor protein gene. Such animal models can provide useful models of human genetic diseases such as Alzheimer's Disease.

Canadian Patent application 2096911 describes a nucleic acid coding for amyloid precursor protein-cleaving protease, which is associated with Alzheimer's Disease and Down's syndrome. The genetic information may be used to diagnose Alzheimer's disease. The genetic information was isolated from chromosome 19. Canadian patent application 2071105, describes detection and treatment of inherited or acquired Alzheimer's disease by the use of YAC nucleotide sequences. The YACs are identified by the numbers 23CB10, 28CA12 and 26FF3.

U.S. Pat. No. 5,297,562, describes detection of Alzheimer's Disease having two or more copies of chromosome 21. Treatment involves methods for reducing the proliferation of chromosome 21 trisomy. Canadian Patent application 2054302, describes monoclonal antibodies which recognize human brain cell nucleus protein encoded by chromosome 21 and are used to detect changes or expression due to Alzheimer's Disease or Down's Syndrome. The monoclonal antibody is specific to a protein encoded by human chromosome 21 and is linked to large pyramidal cells of human brain tissue.

By extensive effort and a unique approach to investigating the AD3 region of chromosome 14q, we have isolated, cloned and sequenced the Alzheimer's related membrane protein (ARMP) gene from within the AD3 region on chromosome 14q24.3. In addition, the direct sequencing of RT-PCR products spanning this 3.0 kb cDNA transcript isolated from affected members of six large pedigrees linked to chromosome 14, has led to the discovery of missense mutations in each of the six pedigrees. These mutations are absent in normal chromosomes. We have established that the ARMP gene is causative of familial Alzheimer's Disease type AD3. In realizing this link, it is understood that mutations in this gene can be associated with other cognitive, intellectual, or psychological diseases such as cerebral hemorrhage, schizophrenia, depression, mental retardation and epilepsy. These phenotypes are present in these AD families and these phenotypes have been seen in mutations of the APP protein gene. The Amyloid Precursor Protein (APP) gene is also associated with inherited Alzheimer's Disease. The identification of both normal and mutant forms of the ARMP gene and gene products has allowed for the development of screening and diagnostic tests for ARMP utilizing nucleic acid probes and antibodies to the gene product. Through interaction with the defective gene product and the pathway in which this gene product is involved, gene therapy, manipulation and delivery are now made possible.

SUMMARY OF THE INVENTION

Various aspects of the invention are summarized as follows. In accordance with a first aspect of the invention, a purified mammalian polynucleotide is provided which codes for Alzheimer's related membrane protein (ARMP). The polynucleotide has a sequence which is the functional equivalent of the DNA sequence of ATCC deposit 97124, deposited Apr. 28, 1995. The mammalian polynucleotide may be in the form of DNA, genomic DNA, cDNA, mRNA and various fragments and portions of the gene sequence encoding ARMP. The mammalian DNA is conserved in many species, particularly humans and rodents, especially mice. The souse sequence encoding ARMP has greater than 95% homology with the human sequence encoding the same protein.

Purified human nucleotide sequences which encode mutant ARMP have mutations at nucleotide position i) 685, A→C ii) 737, A→G iii) 986, C→A, iv) 1105, C→G and v) 1478, G→A of Sequence ID No: 1.

The nucleotide sequences encoding ARMP have an alternate splice form in the genes open reading frame. The human cDNA sequence which codas for ARMP has sequence ID No. 1. The mouse sequence which encodes ARMP has sequence ID No. 3. Various DNA and RNA probes and primers may be made from appropriate polynucleotide lengths selected from the sequences. Portions of the sequence also encode antigenic determinants of the ARMP.

Suitable expression vectors comprising the nucleotide sequences are provided along with suitable host cells transfected with such expression vectors.

In accordance with another aspect of the invention, purified mammalian Alzheimer's related membrane protein is provided. The purified protein has an amino acid sequence encoded by polynucleotide sequence as identified above or the human and mouse sequences of sequence ID No. 2 and sequence ID No. 4. The purified protein may have substitution mutations selected from the group consisting of positions identified in Sequence ID No: 2.

i) M 146L
ii) H 163R
iii) A 246E
iv) L 286V and
v) C 410 Y

Polypeptides of at least six amino acid residues are provided. The polypeptides of six or greater amino acid residues may define antigenic epitopes of the ARMP. Monoclonal antibodies having suitably specific binding affinity for the antigenic regions of the ARMP are prepared by use of corresponding hybridama cell lines. In addition, polyclonal antibodies may be prepared which add suitable specific binding affinities for antigenic regions of the ARMP.

In accordance with another aspect of the invention a bioassay is provided for determining if a subject has a normal or mutant ARMP, where the bioassay comprises providing a biological sample from the subject
conducting a biological assay on the sample to detect a normal or mutant gene sequence coding for ARMP, a normal or mutant ARMP amino acid sequence, or a normal or defective protein function.

In accordance with another aspect of the invention, a process is provided for producing ARMP comprising culturing one of the above described transfected host cells under suitable conditions, to produce the ARMP by expressing the DNA sequence. Alternatively, ARMP may be isolated from mammalian cells in which the ARMP is normally expressed.

In accordance with another aspect of the invention, a therapeutic composition comprises ARMP and a pharmaceutically acceptable carrier.

In accordance with another aspect of the invention, a recombinant vector for transforming a mammalian tissue cell to express therapeutically effective amounts of ARMP in the cells is provided. The vector is normally delivered to the cells by a suitable vehicle. Suitable vehicles include vaccinia virus, adenovirus, adeno associated virus, retrovirus, liposome transport, neuraltropic viruses and Herpes simplex virus.

In accordance with another aspect of the invention, a method of treating a patient deficient in normal ARMP comprises administering to the patient a therapeutically effective amount of the protein targeted at a variety of patient cells which normally express ARMP. The extent of administration of normal ARMP may be sufficient to override any effect the presence of the mutant ARMP may have on the patient. As an alternative to protein, suitable ligands and therapeutic agents such as small molecules and other drug agents may be suitable for drug therapy.

In accordance with another aspect of the invention an immunotherapy for treating a patient having Alzheimer's Disease comprises treating the patient with antibodies specific to the mutant ARMP to reduce biological levels or activity of the mutant ARMP in the patient. To facilitate such amino acid therapy, a vaccine composition may be provided for evoking an immune response in a patient of Alzheimer's Disease where the composition comprises a mutant ARMP and a pharmaceutically acceptable carrier with or without a suitable excipient. Therapy with specific ligands which bind to normal or wild type ARMP of either mutant or wild type and which augments normal function of ARMP in membranes and/or cells or inhibits the bad effect of the mutant.

In accordance with another aspect of the invention, a transgenic animal model for Alzheimer's Disease has the mammalian polynucleotide sequence with at least one mutation which when expressed results in mutant ARMP in the animal cells and thereby manifests a phenotype. For example, the human Prion gene when overexpressed in rodent peripheral nervous system and muscle cells causes a quite different response in the animal than the human. The animal may be a rodent and is preferably a mouse.

In accordance with another aspect of the invention a transgenic mouse model for Alzheimer's Disease has the mouse gene encoding ARMP mutated to manifest the symptoms. The transgenic mouse may exhibit symptoms of cognitive memory or behavioural disturbances. In addition or alternatively, the symptoms may appear as cellular tissue disorders such as in mouse liver, kidney spleen or bone marrow.

In accordance with another aspect of the invention, the protein can be used an a starting point for rationale drug design to provide ligands, therapeutic drugs or other types of small chemical molecules.

BRIEF DESCRIPTION OF THE DRAWINGS

Various aspects of the invention are described hereinafter with respect to the drawings wherein.

Figure 1:
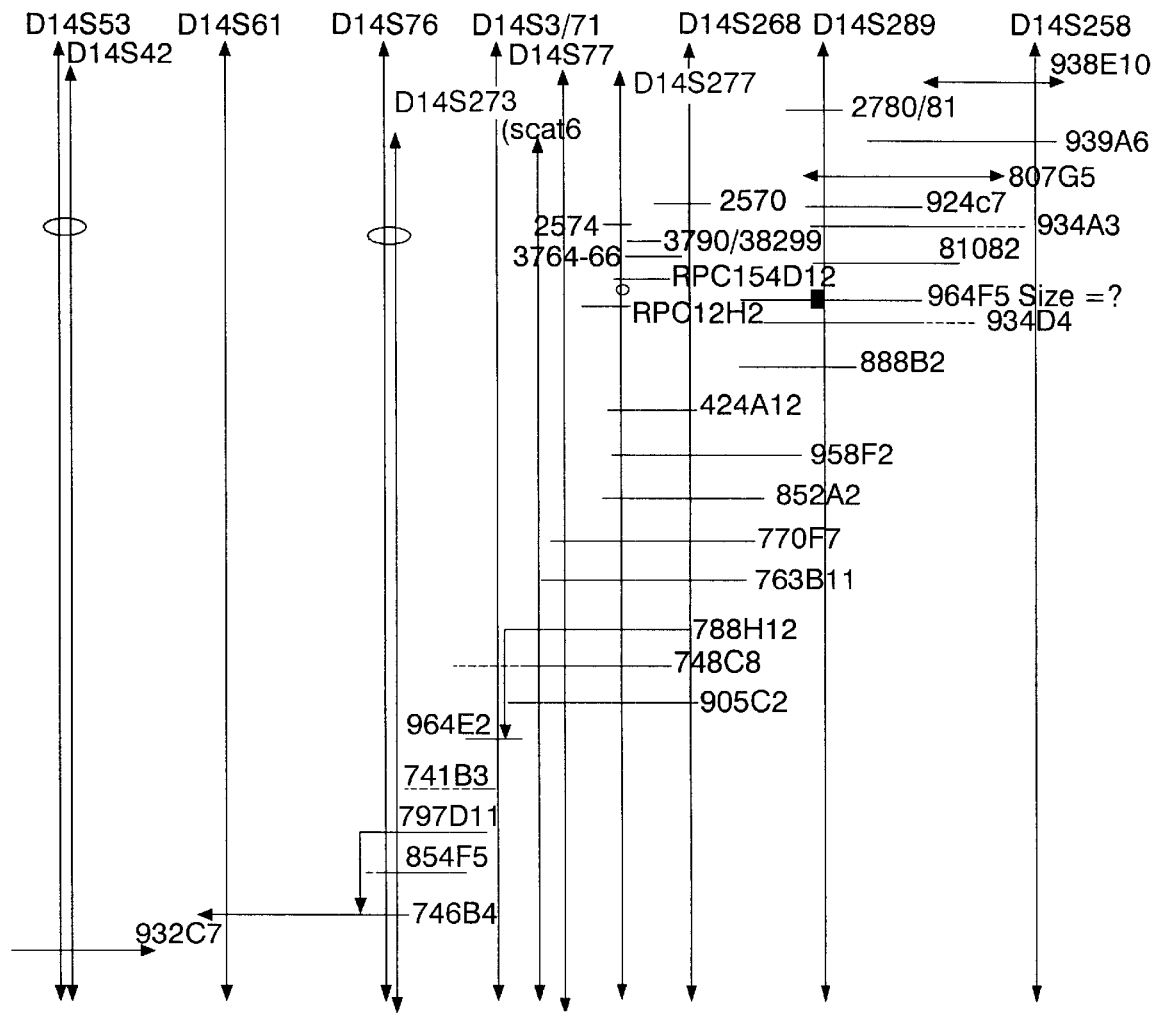
FIG. 1. Is the constructed contig of overlapping genomic DNA fragments cloned into YACs spanning a FAD locus on chromosome 14q.
Figure 2A:
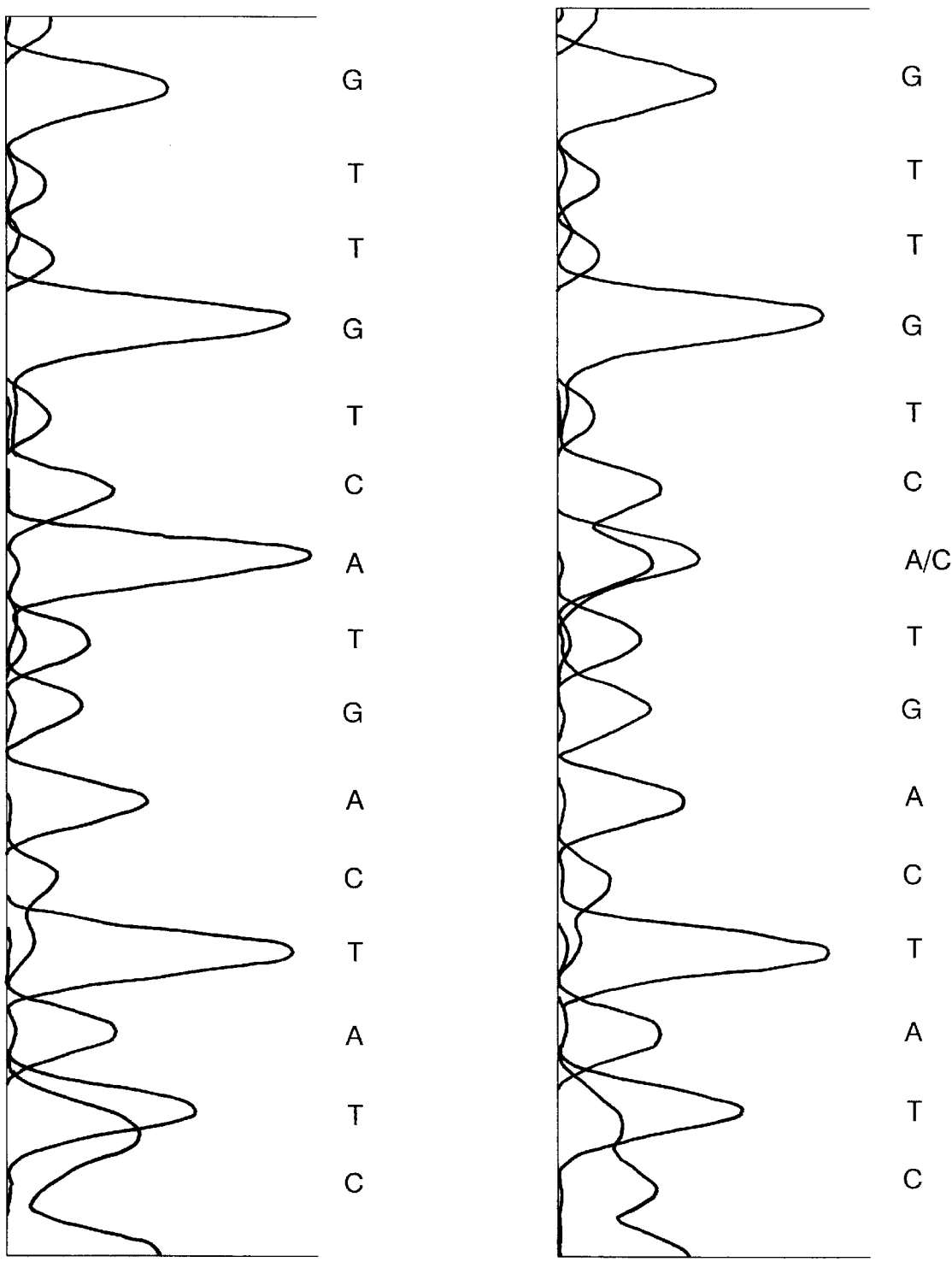
FIGS. 2A–2E. Automated fluorescent chromatograms representing the change in nucleic acids which direct (by codon) the amino acid sequence of the gene. (Wild-type sequence is denoted by first sequence identifier and mutated sequence is denoted by the second sequence identified)
Figure 2B:
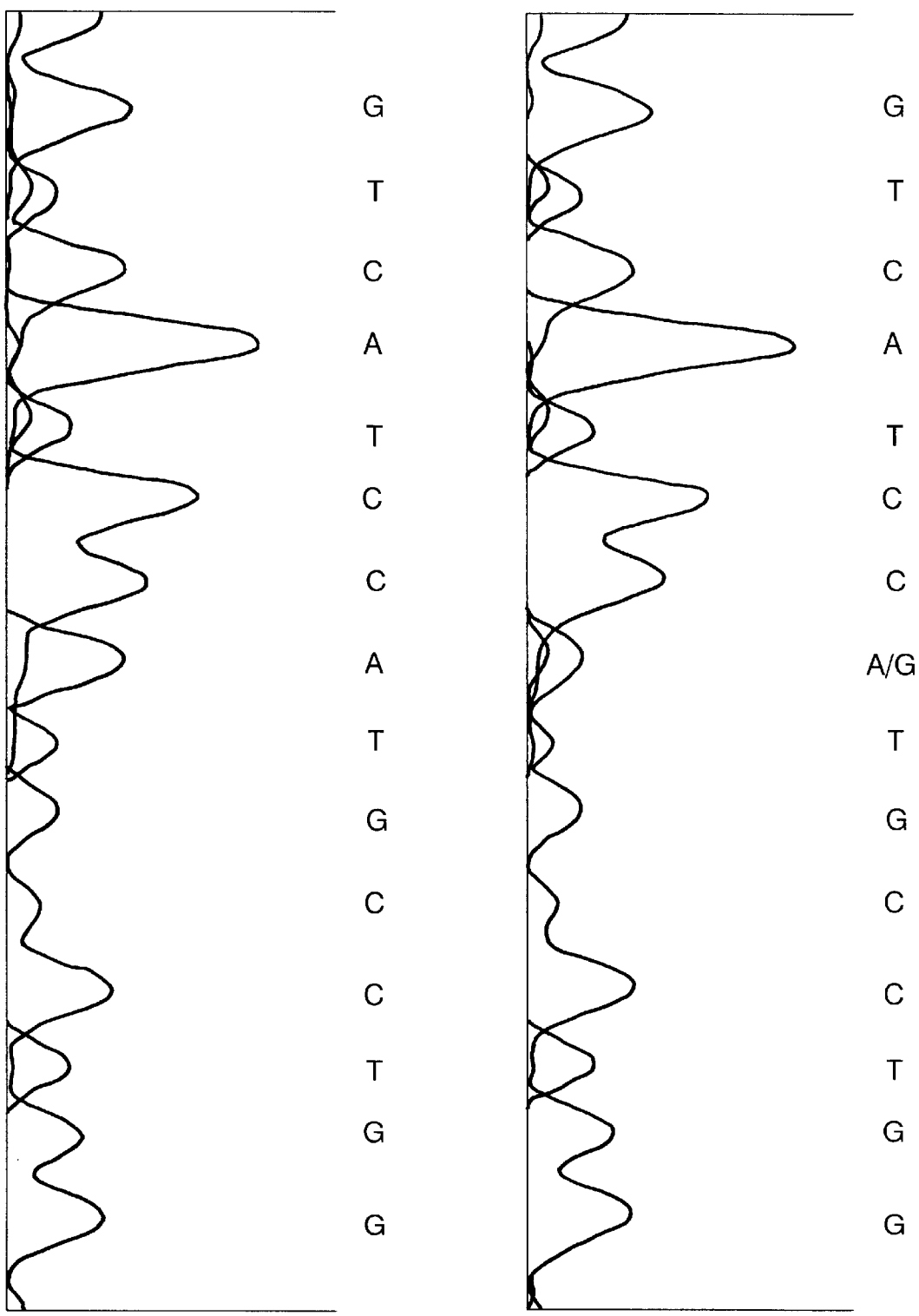
Figure 2C:
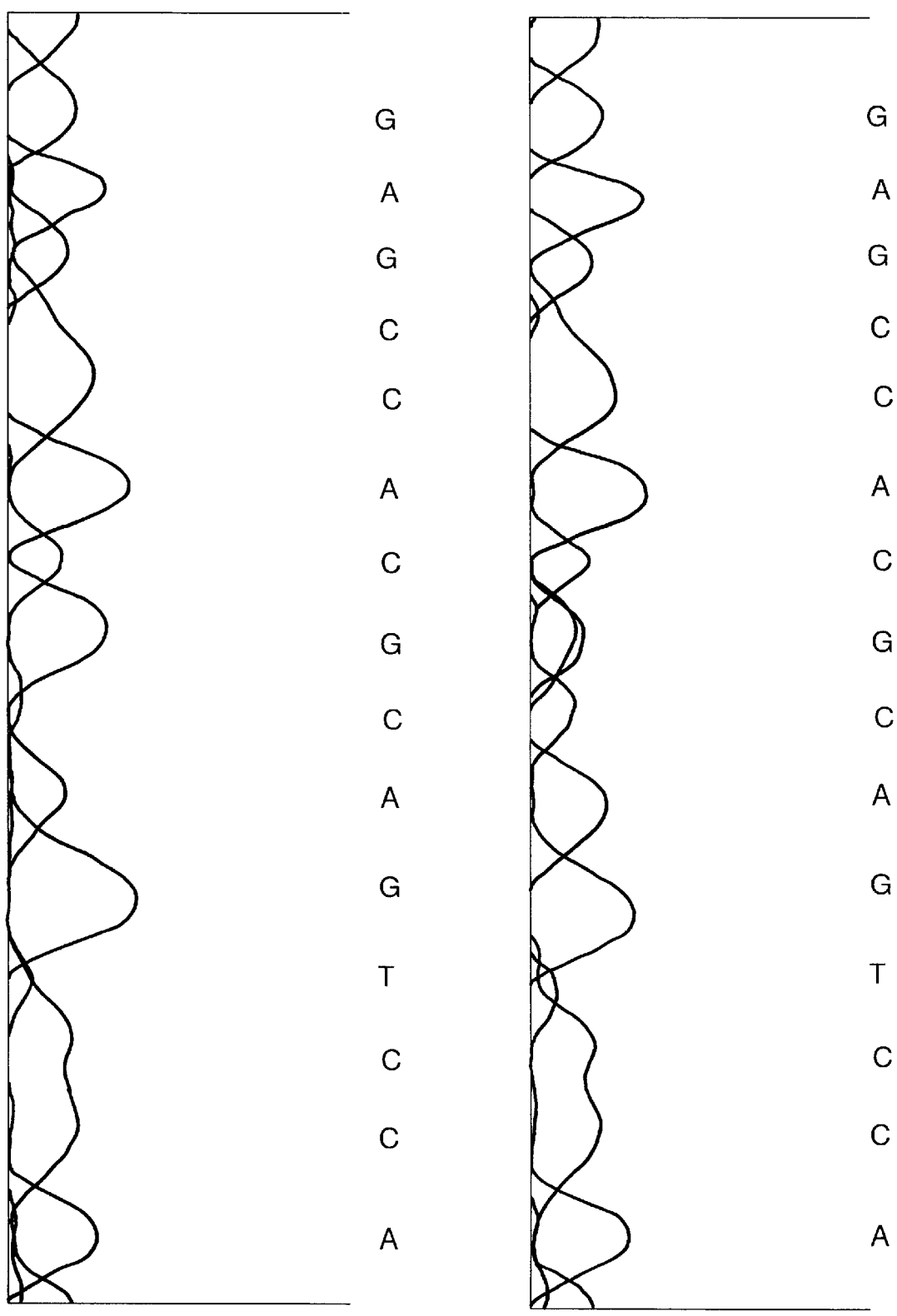
Figure 2D:
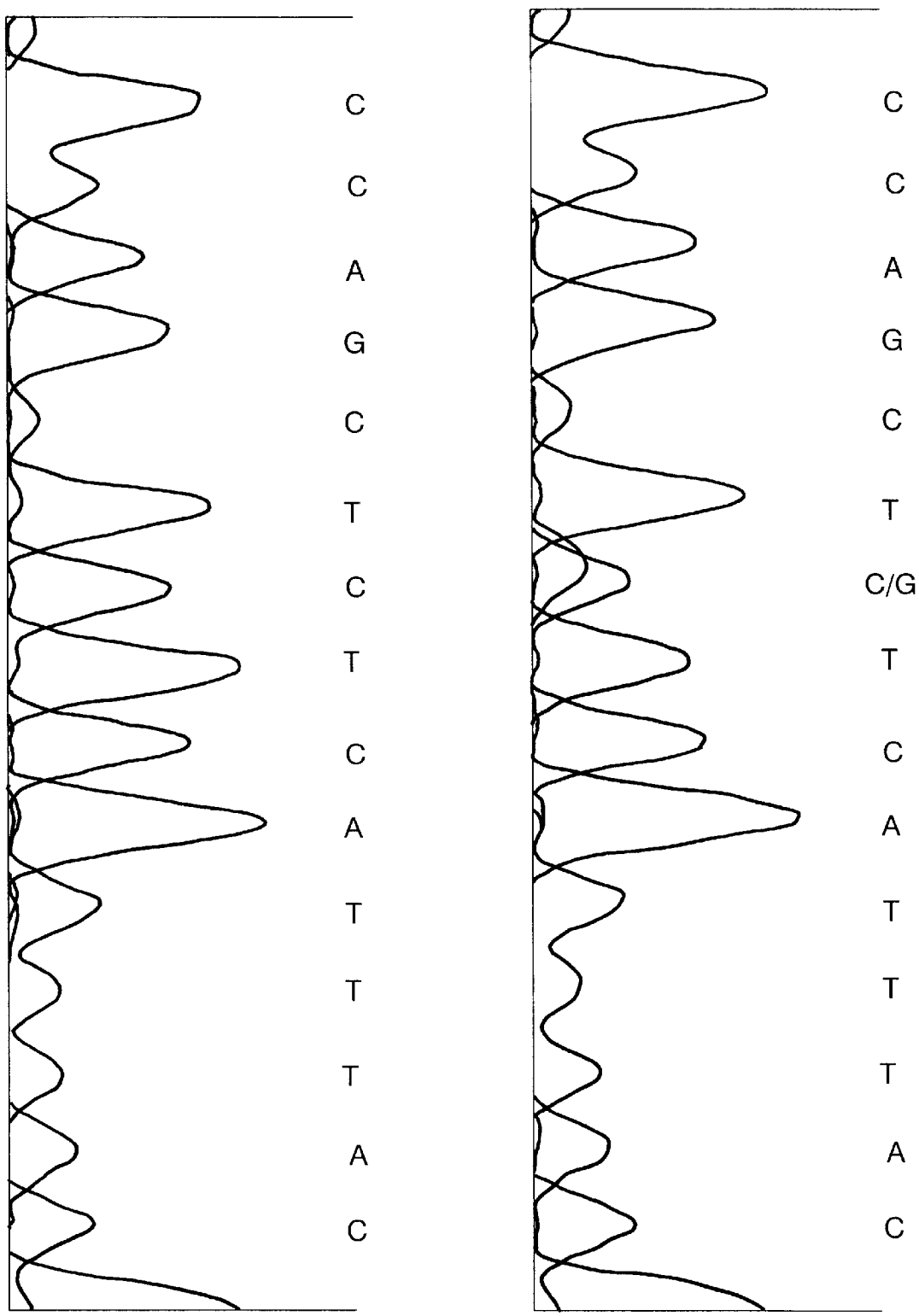
Figure 2E:
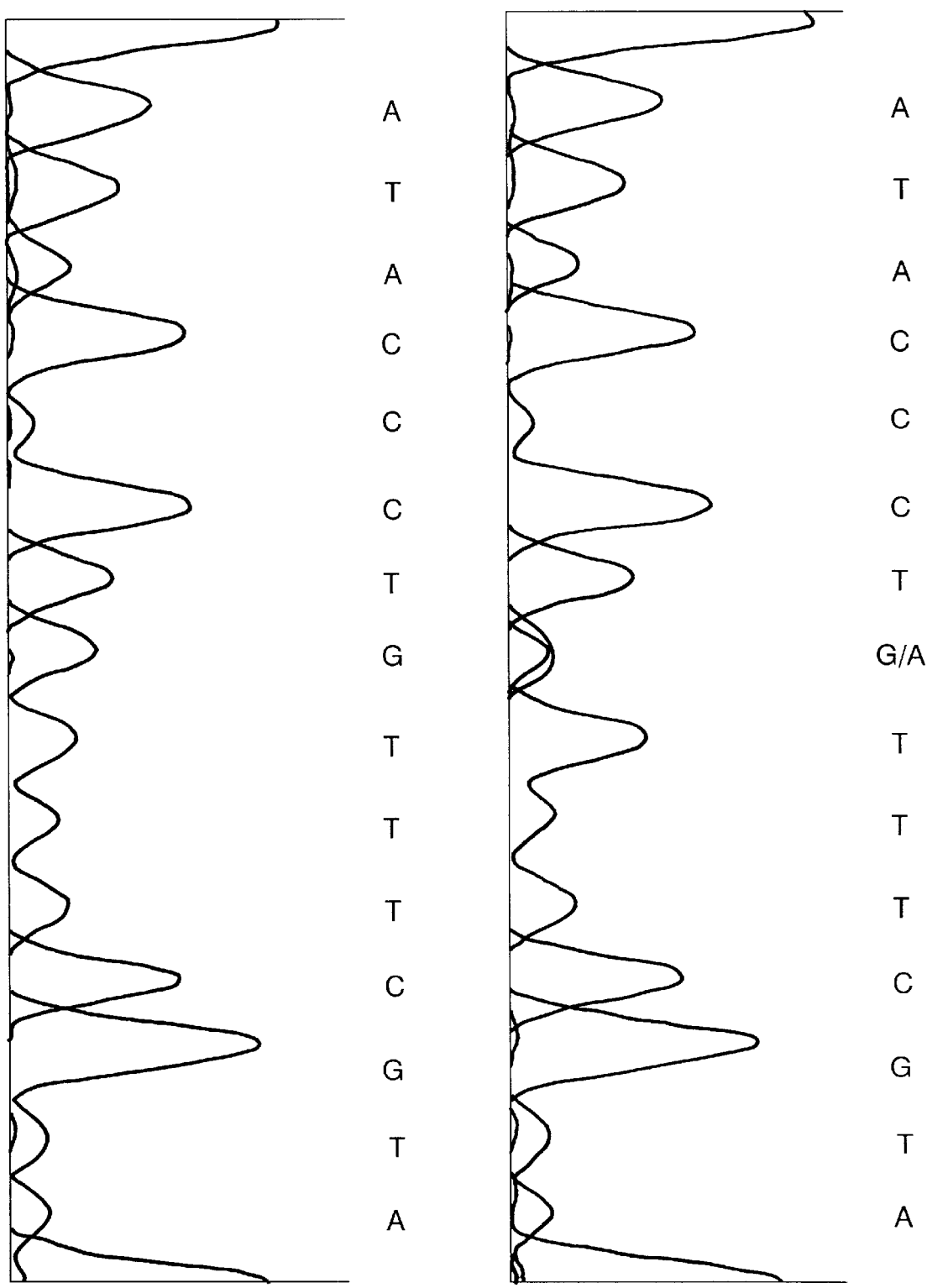

(a) Met 146 Leu (SEQ ID NO:146, SEQ ID NO:147)
(b) His 163 Arg (SEQ ID NO:148, SEQ ID NO:149)
(c) Ala 246 Glu (SEQ ID NO:150, SEQ ID NO:151)
(d) Glu 286 Val (SEQ ID NO:152, SEQ ID NO:153)
(e) Cys 410 Tyr (SEQ ID NO:154, SEQ ID NO:155)

DETAILED DESCRIPTION OF PREFERRED EMBODIMENTS

In order to facilitate review of the various embodiments of the invention and an understanding of various elements and constituents used in making the invention and using same, the following definition of terms used in the invention description is as follows:

AD—Alzheimer's disease

AD3—an aggressive type of Alzheimer's disease

FAD—Familial alzheimer's disease

ARMP—Alzheimer's related membrane protein, encoded by the ARMP gene. The preferred source of protein is the mammalian protein as isolated from human, animal. Alternatively, functionally equivalent proteins may exist in plants, insects and invertebrates. The protein may be produced by recombinant organisms, and as chemically or enzymatically synthesized. This definition is understood to include the various polymorphic forms of the protein wherein amino acid substitutions or deletions of the sequence does not affect the essential functioning of the protein, or its structure.

ARMP carrier—a mammal in apparent good health whose chromosomes contain a mutant ARMP gene that may be transmitted to the offspring and who will develop Alzheimer's Disease in mid to late adult life.

ARMP gene—the gene whose mutant forms are associated with familial Alzheimer's Disease and/or other inheritable disease phenotypes (eg. cerebral hemorrhage, mental retardation, schizophrenia, psychosis, and depression). This definition is understood to include the various sequence polymorphisms that exist, wherein nucleotide substitutions in the gene sequence do not affect the essential function of the gene product as well as functional equivalents of cDNA of Sequence ID No. 1 and No: 3. This term primarily relates to an isolated coding sequence, but can also include some or all of the flanking regulatory elements and/or introns.

Mutant ARMP—a mammalian protein that is highly analogous to ARMP in terms of primary structure, but wherein one or more amino acid deletions and/or substitutions result in impairment of its essential function, so that mammals, especially humans, whose ARMP producing cells express mutant ARMP rather than the normal ARMP demonstrate the symptoms of Alzheimer's Disease and/or other relevant inherible phenotypes (eg. cerebral hemorrhage, mental retardation, schizophrenia, psychosis, and depression).

hARMP gene—human ARMP gene mARMP gene—mouse gene analogous to the human ARMP gene.

Functional equivalent as used in describing gene sequences and amino acid sequences means that a recited sequence need not be identical to the definitive sequence of the Sequence ID Nos but need only provide a sequence which functions biologically and/or chemically the equivalent of the definitive sequence. Hence sequences which correspond to a definitive sequence may also be considered as functionally equivalent sequence.

ORF—open reading frame.

PCR—polymerase chain reaction.

contig—continuous cloned regions

YAC—yeast artificial chromosome

Protein—A polypeptide composed of individual amino acids which are identified as single letter nomenclature.

RT-PCR—reverse transcription polymerase chain reaction.

SSR—Simple sequence repeat polymorphism.

Missense mutation—A mutation of the nucleic acid sequence which alters a codon to that of another amino acid, causing an altered translation product to be made.

Pedigree—In human genetics, a diagram showing the ancestral relationships and transmission of genetic traits over several generations in a family.

linkage analysis—Analysis of co-segregation of a disease trait or disease gene with polymorphic genetic markers of defined chromosomal location.

The present invention is concerned with the identification and sequencing of the mammalian ARMP gene in order to gain insight into the cause and etiology of familial Alzheimer's Disease. From this information, screening methods and therapies for the diagnosis and treatment of the disease can be developed. The gene has been identified, isolated and cloned, and its transcripts and gene products identified and sequenced. During such identification of the gene, considerable sequence information has also been developed on intron information in the ARMP gene, flanking untranslated information and signal information and information involving neighbouring genes in the AD3 chromosome region. Direct sequencing of overlapping RT-PCR products spanning the human gene isolated from affected members of large pedigrees linked to chromosome 14 has led to the discovery of missense mutations which co-segregate with the disease.

Although it in generally understood that Alzheimer's Disease is a neurological disorder, most likely in the brain, we have found expression of ARMP in varieties of human tissue such as heart, brain, placenta, lung, liver, skelatal muscle, kidney and pancreas. Although this gene is expressed widely, the clinically apparent phenotype exists in brain although it is conceivable that biochemical phenotypes may exist in these other tissues. As with other genetic diseases much as Huntington's Disease and APP—Alzheimer's, the clinical disease manifestation may reflect different biochemistries of different cell types and tissues (which stem from genetics and the protein). Such findings suggest that AD may not be solely a neurological disorder but may also be a physiological disorder, hence requiring alternative therapeutic strategies which may be targeted to other tissues or organs or generally in addition or separately from neuronal or brain tissues.

The identification of these mutations are related to Alzheimer disease pathology. With the identification and sequencing of the gene and the gene product, probes and antibodies raised to the gene product can be used in a variety of hybridization and immunological assays to screen for and detect the presence of either a normal or mutated gene or gene product.

Patient therapy through removal or blocking of the mutant gene product, as well as supplementation with the normal gene product by amplification, by genetic and recombinant techniques or by immunotherapy can now be achieved. Correction or modification of the defective gene product by protein treatment immunotherapy (using antibodies to the defective protein) or knock-out of the mutated gene is now also possible. Familial Alzheimer's Disease could also be controlled by gene therapy in which the gene defect is corrected insitu or by the use of recombinant or other vehicles to deliver a DNA sequence capable of expressing the normal gene product, or a deliberately mutated version of the gene product whose effect counter balances the deleterious consequences of the disease mutation to the affected cells of the patient.

Isolating the Human ARMP Gene Genetic Mapping of the AD3 Locus

After the initial regional mapping of the AD3 gene locus to 14q24.3 near the anonymous microsatellite markers D14S43 and D14S53 (Schellenberg, G D at al., 1992; St George-Hyslop, P at al., 1992; Van Broeckhoven, C et al., 1992), we used twenty one pedigrees segregating AD as a putative autosomal dominant trait (St George-Hyslop, P et al., 1992) to investigate the segregation of 18 additional genetic markers from the 14q24.3 region which had been organized into a high density genetic linkage map (FIG. 1) (Weissenbach et al., 1992; Gyapay et al., 1994). Pairwise maximum likelihood analyses previously published confirmed substantial cumulative evidence for linkage between FAD and all of these markers (Table 1). However, much of the genetic data supporting linkage to these markers were derived from six large early onset pedigrees FAD1 (Nee et al., 1983), FAD2 (Frommelt et al., 1991), FAD3 (Goudsmit et al., 1981; Pollen, 1993), FAD4 (Foncin et al., 1985), TOR1.1 (Bergamini, 1991) and 603 (Pericak-Vance et al., 1988) each of which provide at least one anonymous genetic marker from 14q24.3 (St. George-Hyslop, P. et al 1992).

In order to more precisely define the location of the AD3 gene relative to the known locations of the genetic markers from 14q24.3, we initially sought recombinational landmarks by direct inspection of the raw haplotype data only from genotyped affected members of the six pedigrees showing definitive linkage to chromosome 14. This selective strategy in this particular instance necessarily discards data from the reconstructed genotypes of deceased affected members as well as from elderly asymptomatic members of the large pedigrees, and takes no account of the smaller pedigrees of uncertain linkage status. However, this strategy is very sound because it also avoids the acquisition of potentially misleading genotype data acquired either through errors in the reconstructed genotypes of deceased affected members arising from non-paternity or sampling errors or from the inclusion of unlinked pedigrees.

Upon inspection of the haplotype data for affected subjects, members of the six large pedigrees whose genotypes were directly determined revealed obligate recombinants at D14S48 and D14S53, and at D14S258 and D14S56. The single recombinant at D14S53, which depicts a telomeric boundary for the FAD region, occurred in the same AD affected subject of the FAD1 pedigree who had previously been found to be recombinant at several other markers located telomeric to D14S53 including D14S48 (St George-Hyslop, P et al., 1992). Conversely, the single recombinant at D14S258, which marks a centromeric boundary of the FAD region, occurred in an affected member of the FAD3 pedigree who was also recombinant at several other markers centromeric to D14S258 including D14S63. Both recombinant subjects had unequivocal evidence of Alzheimer's disease confirmed through standard clinical tests for the illness in other affected members of their families, and the genotype of both recombinant subjects was informative and co-segregating at multiple loci within the interval centromeric to D14S53 and telomeric to D14S258.

When the haplotype analyses were enlarged to include the reconstructed genotypes of deceased affected members of the six large pedigrees as well as data from the remaining fifteen pedigrees with probabilities for linkage of less than 0.95, several additional recombinants were detected at one or more marker loci within the interval between D14S53 and D14S258. Thus, one additional recombinant was detected in the reconstructed genotype of a deceased affected member of each of three of the larger FAD pedigrees (FAD1, FAD2 and other related families), and eight additional recombinants were detected in affected members of five smaller FAD pedigrees. However, while some of these recombinants might have correctly placed the AD3 gene within a more defined target region, we were forced to regarded these potentially closer "internal recombinants" as unreliable not only for the reasons discussed earlier, but also because they provided mutually inconsistent locations for the AD3 gene within the D14S53-D14S258 interval.

Construction of a Physical Contig Spanning the AD3 Region

As an initial step toward cloning the AD3 gene we next constructed a contig of overlapping genomic DNA fragments cloned into yeast artificial chromosome vectors, phage artificial chromosome vectors and cosmid vectors (FIG. 1). FISH mapping studies using cosmids derived from the YAC clones 932c7 and 964f5 suggested that the interval most likely to carry the AD3 gene was at least five megabases in size. Because the large size of this minimal co-segregating region would make positional cloning strategies intractable, we sought additional genetic pointers which might focus the search for the AD3 gene to one or more subregions within the interval flanked by D14S53 and D14S258. Haplotype analyses at the markers between D14S53 and D14S258 failed to detect statistically significant evidence for linkage disequilibrium and/or allelic association between the FAD trait and alleles at any of these markers, irrespective of whether the analyses were restricted to those pedigrees with early onset forms of FAD, or were generalized to include all pedigrees. This result was not unexpected given the diverse ethnic origins of our pedigrees. However, when pedigrees of similar ethnic descent were collated, direct inspection of the haplotype observed on the disease bearing chromosome segregating in different pedigrees of similar ethnic origin revealed two clusters of marker loci (one located centromeric to D14S77 (D14S268, D14S277 and RSCAT6), and the other telomeric to D24S77 (D14S43, D14S273, and D14S76), at which identical alleles were observed in at least two pedigrees from the same ethnic origin (Table 2). As part of our strategy, we reasoned that the presence of shared alleles at one of these groups of physically clustered marker loci might reflect the co-inheritance of a small physical region surrounding the ARMP gene on the original founder chromosome in each ethnic population.

Transcription Mapping and Preliminary Analysis of Candidate Genes

In order to recover expressed sequences encoded within the interval between D14S53 and D14S258, we employed direct hybridization selection strategies using cloned genomic fragments from the contig and concentrating upon clones covering the two regions highlighted by the genetic studies (Canadian Patent application publication number 2,092,455; Rommens at al., 1993; Church et al., 1994). Both methods produced short putatively transcribed sequences which ware subsequently used to screen conventional cDNA libraries for longer clones. Reiterative application of these methods led to the development of a partial, transcription map of the AD3 region (FIG. 1). In total, evidence for at least 20–900 transcription units were identified from the smaller fragments.

Recovery of Potential Candidate Genes

Each of the open reading frame portions of the candidate genes were recovered by RT-PCR from mRNA isolated from post-mortem brain tissue of normal control subjects and from either post-mortem brain tissue or cultured fibroblast cell lines of affected members of six pedigrees definitively linked to chromosome 14. The RT-PCR products were then screened for mutations using chemical cleavage and REF-SSCP methods (Saleeba and Cotton, 1993; Liu and Sommer, 1995), and by direct nucleotide sequencing. With one exception, all of the genes examined, although of interest, were not unique to affected subjects, and did not co-segregated with the disease. The single exception was the candidate gene represented by clone S182.

The remaining sequences a subset of which are mapped in FIG. 1 together with additional putative transcriptional sequences not identified in FIG. 1 are identified in the sequence listings as 14 through 43. The Sequence ID Nos: 14 to 43 represent neighbouring genes or fragments of neighbouring genes adjacent the hARMP gene or possibly additional coding fragment arising from alternative splicing of the hARMP. Such sequences are useful for creating primers, for creating diagnostic tests, creating altered regulatory sequences and use of adjacent genomic sequences to create better animal models.

Characterization of the hARMP Gene

The S182 clone identified a transcript expressed widely in many areas of brain and peripheral tissues as a major 3.0 kb transcript and a minor transcript of 7.0 kb. The nucleotide sequence of the major transcript was determined from the consensus of eight additional overlapping clines recovered either from cDNA libraries or by 5'RACE, and bears no significant homology to other human genes. The cDNA of the sequenced transcript is provided in Sequence ID No: 1 and the predicted amino acid sequence is provided in Sequence ID No: 2. Analysis of the 5' end of multiple cDNA clones and RT-PCR products as well as corresponding genomic clones indicates that transcription begins from two different start sites. The longest predicted open reading frame containing 467 amino acids (SEQ ID No: 2) with a small alternatively spliced exon of 4 amino acids at 25 codons from the putative start codon (SEQ ID NO:5) (Table 3). This putative start codon is the first in phase ATG revealing that the 5' untranslated region is contained within at least two exons (Rogaer et al, in preparation). Comparison of the nucleic acid and predicted amino acid sequences with available databases using the BLAST alignment paradigms revealed modest amino acid similarity with the *C. elegans* sperm integral membrane protein spe-4 (p=1.5e−25, 24−37% identity over three groups of at least fifty residues) and weaker similarity to several other membrane spanning proteins including mammalian chromogranin A and alpha subunit of mammalian voltage dependent calcium channels (Altschul et al., 1990). This clearly established that they are not the same gene.

Further investigation of the hARMP has revealed a host of sequence fragments which form the hARMP gene and include intron sequence information, 5' end untranslated sequence information and 3' end untranslated sequence information. Such sequence fragments are identified in sequence ID Nos. 6 to 13 and 44 to 125.

Mutations in the S182 Transcript

Direct sequencing of overlapping RT-PCR products spanning the 3.0 kb S182 transcript isolated from affected members of the six large pedigrees linked to chromosome 14 led to the discovery of missense mutations in each of the six pedigrees (Table 2, FIG. 2). Each of these mutations co-segregated with the disease in the respective pedigrees, and were absent from 142 unrelated neurologically normal subjects drawn from the same ethnic origins as the FAD pedigrees. (284 unrelated chromosomes).

The location of the gene within the physical interval segregating with AD3 trait, the presence of five different missense mutations which co-segregate with the disease trait in six pedigrees definitively linked to chromosome 14, and the absence of these mutations in 284 independent normal chromosomes cumulatively confirms that the hARMP gene is the AD3 locus. Further biologic support for this hypothesis arises both from the fact that the residues mutated in FAD kindreds are conserved in evolution (Table 3) and occur in domains of the protein which are also highly conserved, and from the fact that the S182 gene product in expressed at high levels in most regions of the brain including the most severely affected with AD.

The DNA sequence for the hARMP gene as cloned has been incorporated into a plasmid Bluscript. This stable vector has been deposited at ATCC under accession number 97124 on Apr. 28, 1995.

We have recognized several mutations in the hARMP gene which cause a severe type of familial Alzheimer's Disease. One, or a combination of these mutations may be responsible for this form of Alzheimer's Disease as well as several other neurological disorders. The mutations may be any form of amino acid alteration or substitution. Specific disease causing mutations in the form of amino acid substitutions have been located, although we anticipate additional mutations will be found in other families, are as follows. The mutations are listed in respect of their nucleotide locations in Sequence ID No: 1 and amino acid locations in Sequence ID No: 2.

| | |
|---|---|
| i) 685, A→C | Met 146 Leu |
| ii) 737, A→G | His 163 Arg |
| iii) 986, C→A | Ala 246 Glu |
| iv) 1105, C→G | Leu 286 Val |
| v) 1478, G→A | Cys 410 Tyr |

The Met146Leu, Ala246Glu and Cys410Tyr mutations have not been detected in the genomic DNA of affected members of the eight remaining small early onset autosomal dominant FAD pedigrees or six additional families in our collection which express late FAD onset. We predict that such mutations would not commonly occur in late onset FAD which has been excluded by genetic linkage studies from the more aggressive form of AD linked to chromosome 14q24.3 (St George-Hyslop, P et al., 1992; Schellenberg et al., 1993). The His163Arg mutation has been found in the genomic DNA or affected members of one additional FAD pedigree for which positive but significant satistical evidence for linkage to 14 becomes established. Age of onset of affected members was consistent with affected individuals from families linked to chromosome 14.

ARMP Protein

With respect to DNA SEQ ID NO.1, analysis of the sequence of overlapping cDNA clones predicted an ORF protein of 467 amino acids when read from the first in phase ATG start codon and a molecular mass of approximately 52.6 kDa as later described, due to either polymorphisms in the protein or alternate splicing of the transcript the molecular weight of the protein can vary due to possible substitutions or deletions of amino acids.

The analysis of predicted amino acid sequence using the Hopp and Woods algorithm suggest that the protein product is a multispanning membrane protein. The N-terminal is characterized by a highly hydrophylic basic charged domain with several potential phosphorylation domains, followed sequentially by a hydrophobia membrane spanning domain of 19 residues; a charged hydrophyllic loop, then six additional hydrophobic membrane spanning domains interspersed with short (5–20 residue) hydrophyllic domains; an additional charged loop, and then at least one and possibly two other hydrophobic potentially membrane spanning domains culminating in a basic, hydrophyllic domain at the C-terminus (Table 4). The presence of seven membrane spanning domains is characteristic of several classes of G-coupled receptor proteins but is also observed with other proteins including channel proteins.

Comparison of the nucleic acid and predicted, amino acid sequences with available databases using the BLAST alignment paradigms revealed amino acid similarity with the *C. elegans* sperm integral membrane protein spe-4 and a similarity to several other membrane spanning proteins including mammalian chromogranin A and the α-subunit of mammalian voltage dependent calcium channels.

An mentioned purified normal ARMP protein is characterized by a molecular weight of 52.6 kDa. The normal ARMP protein, substantially free of other proteins, is encoded by the aforementioned SEQ. ID No. 1. As will be later discussed, the ARMP protein and fragments thereof may be made by a variety of methods. Purified mutant ARMP protein is characterized by FAD—associated phenotype (necretic death, apoptic death, granulorascular degeneration, neurofibrillary degeneration, abnormalities or changes in the metabolism of APP, and $Ca^{2+}$, $K^+$, and glucose, and mitochondrial function and energy metabolism neurotransmitter metabolism, all of which have been found to be abnormal in human brain, and/or peripheral tissue cells in subjects with Alzheimer's Disease) in a variety of cells. The mutant ARMP, free of other proteins, is encoded by the mutant DNA sequence.

Function of the ARMP Protein

The amino acid sequence analysis suggest that this protein is intimately associated with cellular membranes. The presence of multiple membrane spanning domains argues that this protein is likely to be an integral membrane protein such as a receptor or a channel protein, although they do not preclude a structural membrane protein. It is also conceivable that the protein be a cellular protein with a highly compact three dimensional structure in which respect is may be similar to APOE which is also related to Alzheimer's Disease. In light of this putative functional role, we propose that this gene might be labelled as the Alzheimer Related Membrane Protein (ARMP). The protein also contains a number of potential phosphorylation sites, one of which is the consenses site for MPPkinase which is also involved in the hyperphosphorylation of tau during the conversion of normal tau to neurofibrillary tangles. This consenses sequence may provide a common putative pathway linking this protein and other known biochemical aspects of Alzheimer's Disease and would represent a likely therapeutic target. Review of the protein structure reveals two sequences YTPF (residues 115–119) and STPE (residues 353–356) which represent the 5/T-P motif which is the MAP kinase consensus sequence.

Isolation and Purification of the ARMP Protein

The ARMP protein may be isolated and purified by methods selected on the basis of properties revealed by its sequence. Since the protein possesses properties of a membrane-spanning protein, a membrane fraction of cells in which the protein is highly expressed (eg. central nervous system cells or cells from other tissues) would be isolated and the proteins removed by extraction and the proteins solubilized using a detergent.

Purification can be achieved using protein purification procedures such as chromatography methods (gel-filtration, ion-exchange and inmunoaffinity), by high-performance liquid chromatography (RP-HPLC, ion-exchange HPLC, size-exclusion HPLC, high-performance is chromatofocusing and hydrophobic interaction chromatography) or by precipitation (immunoprecipitation). Polyacrylamide gel electrophoresis can also be used to isolate the ARMP protein based on its molecular weight, charge properties and hydrophobicity.

Similar procedures to those just mentioned could be used to purify the protein from cells transfected with vectors containing the ARMP gene.

Purified protein can be used in further biochemical analyses to establish secondary and tertiary structure which may aid in the design of pharmaceuticals to interact with the protein, alter protein charge configuration or charge interaction with other proteins, lipid or saccharide moities, alter its function in membranes as a transporter channel or receptor and/or in cells an an enzyme or structural protein and treat the disease.

Isolating Mouse ARMP Gene

In order to characterize the physiological significance of the normal and mutant hARMP gene and gene products in a transgenic mouse model it was necessary to recover a mouse homologue of the hARMP gene. We recovered a marine homologue for the A gene by screening a mouse cDNA library with a labelled human DNA probe and in this manner recovered a 2 kb partial transcript. Sequencing of the a 2 kb partial cDNA transcript of the murine homologue revealed substantial amino acid identity. The sequence cDNA is identified is Sequence ID No. 3 and the predicted amino acid Sequence is provided in Sequence ID No. 4. More importantly, all four amino acids that were mutated in the FAD pedigrees were conserved between the murine homologue (SEQ ID NO:4) and the normal human variant (SEQ ID NO:2) (Table 3). This conservation of the ARMP gene as is shown in table 3, indicates that an orthologous gene exists in the mouse (mARMP), and it is now be possible to clone mouse genomic libraries using human ARMP probes. This will also make it possible to identify and characterize the ARMP gene in other species. This also provides evidence of animals with various disease states or disorders currently known or yet to be elucidated.

Transgenic Mouse Model

The creation of a mouse model for Alzheimer's Disease is important to the understanding of the disease and for the tasting of possible therapies. Currently no unambiguous viable animal model for Alzheimer's Disease exists.

There are several ways in which to create an animal model for Alzheimer's Disease. Generation of a specific mutation in the mouse gene such as the identified hARMP gene mutations is one strategy. Secondly, we could insert a wild type human gene and/or humanize the murine gene by homologous recombination. It is also possible to insert a mutant (single or multiple) human gene as genomic or minigene constructs using wild type or mutant or artificial promoter elements. More commonly, knock-out of the endogenous murine genes may be accomplished by the insertion of artificially modified fragments of the endogaenous gene by homologous recombination. The modifications include insertion of mutant stop codons, the deletion of DNA sequences, or the inclusion of recombination elements (lcx p sites) recognized by enzymes such as Cre recombinase.

To inactivate the mARMP gene chemical or x-ray mutagenesis of mouse gametes, followed by fertilization, can be applied. Heterozygous offspring can then be identified by southern blotting to demonstrate lose of one allele by dosage, or failure to inherit one parental allele using RFLP markers.

To create a transgenic mouse a mutant version of hARMP or mARMP can be inserted into a mouse germ line using standard techniques of oocyte microinjection or transfection or microinjection into stem cells. Alternatively, if it is desired to inactivate or replace the endogenous mARMP gene, homologous recombination using embryonic stem cells may be applied.

For oocyte injection, one or more copies of the mutant ARMP gene can be inserted into the pronucleus of a just-fertilized mouse oocyte. This oocyte is then reimplanted into a pseudo-pregnant foster mother. The liveborn mice can then be screened for integrants using analysis of tail DNA for the presence of human ARMP gene sequences. The transgene can be either a complete genomic sequence injected as a YAC or chromosome fragment, a cDNA with either the natural promoter or a heterologous promoter, or a minigene containing all of the coding region and other elements found to be necessary for optimum expression.

Retroviral infection of early embryos can also be done to insert the mutant hARMP. In this method, the mutant hARMP is inserted into a retroviral vector which is used to directly infect mouse embryos during the early stages of development to generate a chimera, some of which will lead to germline transmission.

Homologous recombination using stem cells allows for the screening of gene transfer cells to identify the rare homologous recombination events. Once identified, these can be used to generate chimeras by injection of mouse blastocysts, and a proportion of the resulting mice will show germline transmission from the recombinant line. This methodology is especially useful if inactivation of the mARMP gene is desired. For example, inactivation of the mARMP gene can be done by designing a DNA fragment which contains sequences from a mARMP exon flanking a selectable marker. Homologous recombination leads to the insertion of the marker sequences in the middle of an exon, inactivating the mARMP gene. DNA analysis of individual clones can then be used to recognize the homologous recombination events.

It is also possible to create mutations in the mouse germline by injecting oligonucleotides containing the mutation of interest and screening the resulting cells by PCR.

This embodiment of the invention has the most significant commercial value as a mouse model for Alzheimer's Disease. Because of the high percentage of sequence conservation between human and mouse it is contemplated that an orthologous gene will exist also in many other species. It is thus contemplated that it will be possible to generate other animal models using similar technology.

Screening and Diagnosis for Alzheimer's Disease

Screening for Alzheimer's Disease as linked to chromosome 14 may now be readily carried out because of the knowledge of the mutations in the gene.

People with a high risk for Alzheimer's Disease (present in family pedigree) or, individuals not previously known to be at risk, or people in general may be screened routinely using probes to detect the presence of a mutant ARMP gene by a variety of techniques. Genomic DNA used for the diagnosis may be obtained from body cells, such as those present in the blood, tissue biopsy, surgical specimen, or autopsy material. The DNA may be isolated and used directly for detection of a specific sequence or may be PCR amplified prior to analysis. RNA or aDNA may also be used. To detect a specific DNA sequence hybridization using specific oligonucleotides, direct DNA sequencing, restriction enzyme digest, RNase protection, chemical cleavage, and ligase-mediated detection are all methods which can be utilized. Oligonucleotides specific to mutant sequences can be chemically synthesized and labelled radioactively with isotopes, or non-radioactively using biotin tags, and hybridized to individual DNA samples immobilized on membranes or other solid-supports by dot-blot or transfer from gels after electrophoresis. The presence or absence of these mutant sequences are then visualized using methods such as autoradiography, fluorometry, or colorimetric reaction. Examples of suitable PCR primers which are useful for example in amplifying portions of the subject sequence containing the aforementioned mutations are set out in Table 5. This table also sets out the change in enzyme site to provide a useful diagnostic tool as defined herein.

Direct DNA sequencing reveals sequence differences between normal and mutant ARMP DNA. Cloned DNA segments may be used as probes to detect specific DNA segments. PCR can be used to enhance the sensitivity of this method. PCR is an enzymatic amplification directed by sequence-specific primers, and involves repeated cycles of heat denaturation of the DNA, annealing of the complementary primers and extension of the annealed primer with a DNA polymerase. This results in an exponential increase of the target DNA.

Other nucleotide sequence amplification techniques may be used, such as ligation-mediated PCR, anchored PCR and enzymatic amplification as would be understood by those skilled in the art.

Sequence alterations may also generate fortuitous restriction enzyme recognition sites which are revealed by the use of appropriate enzyme digestion followed by gel-blot hybridization. DNA fragments carrying the site (normal or mutant) are detected by their increase or reduction in size, or by the increase or decrease of corresponding restriction fragment numbers. Genomic DNA samples may also be amplified by PCR prior to treatment with the appropriate restriction enzyme and the fragments of different sizes are visualized under UV light in the presence of ethidium bromide after gel electrophoresis.

Genetic testing based on DNA sequence differences may be achieved by detection of alteration in electrophoretic mobility of DNA fragments in gels. Small sequence deletions and insertions can be visualized by high resolution gel electrophoresis. Small deletions may also be detected as changes in the migration pattern of DNA heteroduplexes in non-denaturing gel electrophoresis. Alternatively, a single base substitution mutation may be detected based on differential primer length in PCR. The PCR products of the normal and mutant gene could be differentially detected in acrylamide gels.

Nuclease protection assays (Si or ligase-mediated) also reveal sequence changes at specific locations.

Alternatively, to confirm or detect a polymorphism restriction mapping changes ligated PCR, ASO, REF-SSCP and SSCP may be used. Both REF-SSCP and SSCP are mobility shift assays which are based upon the change in conformation due to mutations.

DNA fragments may also be visualized by methods in which the individual DNA samples are not immobilized on membranes. The probe and target sequences may be in solution or the probe sequence may be immobilized. Autoradiography, radioactive decay, spectrophotometry, and fluorometry may also be used to identify specific individual genotypes.

According to an embodiment of the invention, the portion of the DNA segment that is informative for a mutation, can be amplified using PCR. For example, the DNA segment immediately surrounding the C 410 Y mutation acquired from peripheral blood samples from an individual can be screened using the oligonucleotide primers 885 (tggagactggaacacaac) SEQ ID NO: 127 and 893 (gtgtggccagggtagagaact) SEQ ID NO: 128. This region would then be amplied by PCR, the products separated by electrophoresis, and transferred to membrane. Labelled probes are then hybridized to the DNA fragments and autoradiography performed.

ARMP Expression

Expression of the ARMP gene in heterologous cell systems can be used to demonstrate structure-function relationships. Ligating the ARMP DNA sequence into a plasmid expression vector to transfect cells is a useful method to test the proteins influence on various cellular biochemical parameters. Plasmid expression vectors containing either the entire, or portions thereof, normal or mutant human or mouse ARMP sequence can be used in in vitro mutagenesis experiments which will identify portions of the protein crucial for regulatory function.

The DNA sequence can be manipulated in studies to understand the expression of the gene and its product, to achieve production of large quantities of the protein for functional analysis, for antibody production, and for patient therapy. The changes in the sequence may or may not alter the expression pattern in terms of relative quantities, tissue-specificity and functional properties. Partial or full-length DNA sequences which encode for the ARMP protein, modified or unmodified, may be ligated to bacterial expression vectors. *E. coli* can be used using the T7 RNA polymerase/promoter system using two plasmids or by labeling of plasmid-encoded proteins, or by expression by infection with M13 Phage mGPI-2. *E. coli* vectors can also be used with Phage lamba regulatory sequences, by fusion protein vectors (eg. lacz and trpE), by maltose-binding protein fusions, and by glutathione-S-transferase fusion proteins.

Alternatively, the ARMP protein can be expressed in insect cells using baculoviral vectors, or in mammalian cells using vaccinia virus. For expression in mammalian cells, the cDNA sequence may be ligated to heterologous promoters, such as the simian virus (SV40) promoter in the pSV2 vector and introduced into cells, such as COS cells to achieve transient or long-term expression. The stable integration of the chimeric gene construct may be maintained in mammalian cells by biochemical selection, such as neomycin and mycophoenolic acid.

The ARMP DNA sequence can be altered using procedures such as restriction enzyme digestion, fill-in with DNA polymerase, deletion by exonuclease, extension by terminal deoxynucleotide transferase, ligation of synthetic or cloned DNA sequences, site-directed sequence alteration with the use of specific oligonucleotides together with PCR.

The cDNA sequence or portions thereof, or a mini gene consisting of a cDNA with an intron and its own promoter, is introduced into eukaryotic expression vectors by conventional techniques. These vectors permit the transcription of the cDNA in eukaryotic cells by providing regulatory sequences that initiate and enhance the transcription of the cDNA and ensure its proper splicing and polyadenylation. The endogenous ARMP gene promoter can also be used. Different promoters within vectors have different activities which alters the level of expression of the cDNA. In addition, certain promoters can also modulate function such as the glucocorticoid-responsive promoter from the mouse mammary tumor virus.

Some of the vectors listed contain selectable markers or neo bacterial genes that permit isolation of cells by chemical selection. Stable long-term vectors can be maintained in cells as episomal, freely replicating entities by using regulatory elements of viruses. Cell lines can also be produced which have integrated the vector into the genomic DNA. In this manner, the gene product is produced on a continuous basis.

Vectors are introduced into recipient cells by various methods including calcium phosphate, strontium phosphate, electroporation, lipofection, DEAE dextran, microinjection, or by protoplast fusion. Alternatively, the cDNA can be introduced by infection using viral vectors.

Eukaryotic expression systems can be used for many studies of the ARMP gene and gene product including determination of proper expression and post-translational modifications for full biological activity, identifying regulatory elements located in the 5' region of the ARMP gene and their role in tissue regulation of protein expression, production of large amounts of the normal and mutant protein for isolation and purification, to use cells expressing the ARMP protein as a functional assay system for antibodies generated against the protein or to test effectiveness of pharmacological agents, or as a component of a signal transduction system, to study the function of the normal complete protein, specific portions of the protein, or of naturally occurring and artificially produced mutant proteins.

Using the techniques mentioned, the expression vectors containing the ARMP gene or portions thereof can be introduced into a variety of mammalian cells from other species or into non-mammalian cells.

The recombinant cloning vector, according to this invention, comprises the selected DNA of the DNA sequences of this invention for expression in a suitable host. The DNA is operatively linked in the vector to an expression control sequence in the recombinant DNA molecule so that normal and mutant ARMP protein can be expressed. The expression control sequence may be selected from the group consisting of sequences that control the expression of genes of prokaryotic or eukaryotic cells and their viruses and combinations thereof. The expression control sequence may be selected from the group consisting of the lac system, the trp system, the tac system, the trc system, major operator and promoter regions of phage lambda, the control region of the fd coat protein, early and late promoters of SV40, promoters derived from polyoma, adenovirus, retrovirus, baculovirus, simian virus, 3-phosphoglycerate kinase promoter, yeast acid phosphatase promoters, yeast alpha-mating factors and combinations thereof.

The host cell which may be transfected with the vector of this invention may be selected from the group consisting of *E.coli, pseudomonas, bacillus subtillus, bacillus stearothermophilus,* or other bacili; other bacteria, yeast, fungi, insect, mouse or other animal, plant hosts, or human tissue cells.

For the mutant ARMP DNA sequence similar systems are employed to express and the produce the mutant protein.

Antibodies to Detect ARMP

Antibodies to epitopes with the ARMP protein can be raised to provide information on the characteristics of the proteins. Generation of antibodies would enable the visualization of the protein in cells and tissues using Western blotting. In this technique, proteins are run on polyacrylamide gel and then transferred onto nitrocellulose membranes. These membranes are then incubated in the presence of the antibody (primary), then following washing are incubated to a secondary antibody which is used for detection of the protein-primary antibody complex. Following repeated washing, the entire complex is visualized using colourimetric or chemiluminescent methods.

Antibodies to the ARMP protein also allow for the use of immunocytochemistry and immunofluorescence techniques in which the proteins can be visualized directly in cells and tissues. This is most helpful in order to establish the subcellular location of the protein and the tissue specificity of the protein.

In order to prepare polyclonal antibodies, fusion proteins containing defined portions or all of the ARMP protein can be synthesized in bacteria by expression of corresponding DNA sequences in a suitable cloning vehicle. The protein can then be purified, coupled to a carrier protein and mixed with Freund's adjuvant (to help stimulate the antigenic response by the rabbits) and injected into rabbits or other laboratory animals. Alternatively, protein can be isolated from cultured cells expressing the protein. Following booster injections at bi-weekly intervals, the rabbits or other laboratory animals are then bled and the sera isolated. The sera can be used directly or purified prior to use, by affinity chromatography. The sera can then be used to probe protein extracts run on a polyacrylamide gel to identify the ARMP protein. Alternatively, synthetic peptides can be made to the antigenic portions of the protein and used to innoculate the animals.

To produce monoclonal ARMP antibodies, cells actively expressing the protein are cultured or isolated from tissues and the cell membranes isolated. The membranes, extracts, or recombinant protein extracts, containing the ARMP protein, are injected in Freund's adjuvant into mice. After being injected 9 times over a three week period, the mice spleens are removed and resuspended in phosphate buffered saline (PBS). The spleen cells serve as a source of lymphocytes, some of which are producing antibody of the appropriate specificity. These are then, fused with a permanently growing myeloma partner cell, and the products of the fusion are plated into a number of tissue culture wells in the presence of a selective agent such as HAT. The wells are then screened to identify those containing cells making useful antibody by ELISA. These are then freshly plated. After a period of growth, these wells are again screened to identify antibody-producing cells. Several cloning procedures are carried out until over 90% of the wells contain single clones which are positive for antibody production. From this procedure a stable line of clones is established which produce the antibody. The monoclonal antibody can then be purified by affinity chromatography using Protein A Sepharose.

In situ hybridization is another method used to detect the expression of ARMP protein. In situ hybridization relies upon the hybridization of a specifically labelled nucleic acid probe to the cellular RNA in individual cells or tissues. Therefore, it allows the identification of mRNA within intact tissues, such as the brain. In this method, oligonucleotides corresponding to unique portions of the ARMP gene are used to detect specific mRNA species in the brain.

In this method a rat is anesthetized and transcardially perfused with cold PBS, followed by perfusion with a formaldehyde solution. The brain or, other tissues is then removed, frozen in liquid nitrogen, and cut into thin micron sections. The sections are placed on slides and incubated in proteinase K. Following rinsing in DEP, water and ethanol, the slides are placed in prehybridization buffer. A radioactive probe corresponding to the primer is made by nick translation and incubated with the sectioned brain tissue. After incubation and air drying, the labeled areas are visualized by autoradiography. Dark spots on the tissue sample indicate hybridization of the probe with brain mRNA which demonstrates the expression of the protein.

Therapies

An important aspect of the biochemical studies using the genetic information of this invention is the development of therapies to circumvent or overcome the ARMP gene defect, and thus prevent, treat, control serious symptoms or cure the disease. In view of expression of the ARMP gene in a variety of tissues, one has to recognize that Alzheimer's Disease may not be restricted to the brain. Alzheimer's Disease manifests itself as a neurological disorder which in one of its forms is caused by a mutation in the ARMP gene, but such manifest may be caused by the mutations in other organ tissues, such as the liver, releasing factors which affect the brain activity and ultimately cause Alzheimer's Disease. Hence, in considering various therapies, it in understood that such therapies may be targeted at tissue other than the brain, such as heart, placenta, lung, liver, skeletal muscle, kidney and pancreas, where ARMP is also expressed.

Protein Therapy

Treatment of Alzheimer's Disease can be performed by replacing the mutant protein with normal protein, or by modulating the function of the mutant protein. Once the biological pathway of the ARMP protein has been completely understood, it may also be possible to modify the pathophysiologic pathway (eg. a signal transduction pathway) in which the protein participates in order to correct the physiological defect.

To replace the mutant protein with normal protein, or with a protein bearing a deliberate counterbalancing mutation it is necessary to obtain large amounts of pure ARMP protein from cultured cell systems which can express the protein. Delivery of the protein to the affected brain areas or other tissues can then be accomplished using appropriate packaging or administrating systems.

Gene Therapy

Gene therapy is another potential therapeutic approach in which normal copies of the ARMP gene are introduced into patients to successfully code for normal protein in several different affected cell types. The gene must be delivered to those cells in a form in which it can be taken up and code for sufficient protein to provide effective function. Alternatively, in some neurologic mutants it has been possible to prevent disease by introducing another copy of the homologous gene bearing a second mutation in that gene or to alter the mutation, or use another gene to block its effect.

Retroviral vectors can be used for somatic cell gene therapy especially because of their high efficiency of infection and stable integration and expression. The targeted cells however must be able to divide and the expression of the levels of normal protein should be high because the disease is a dominant one. The full length ARMP gene can be cloned into a retroviral vector and driven from its endogenous promoter or from the retroviral long terminal repeat or from a promoter specific for the target cell type of interest (such as neurons).

Other viral vectors which can be used include adeno-associated virus, vaccinia virus, bovine papilloma virus, or a herpesvirus such as Epstein-Barr virus.

Gene transfer could also be achieved using non-viral means requiring infection in vitro. This would include calcium phosphate, DEAE dextran, electroporation, and protoplast fusion. Liposomes may also be potentially beneficial for delivery of DNA into a cell. Although these methods are available, many of these are lower efficiency.

Transplantation of normal genes into the affected area of the patient can also be useful therapy for Alzheimer's Disease. In this procedure, a normal hARMP protein is transferred into a cultivatable cell type much as glial cells, either exogenously or endogenously to the patient. These cells are then injected serotologically into the disease affected tissue(s). This is a known treatment for Parkinson's disease.

Immunotherapy is also possible for Alzheimer's Disease. Antibodies can be raised to a mutant ARMP protein (or portion thereof) and then be administered to bind or block the mutant protein and its deleterious effects. Simultaneously, expression of the normal protein product could be encouraged. Administration could be in the form of a one time immunogenic preparation or vaccine immunization. An immunogenic composition may be prepared as injectables, as liquid solutions or emulsions. The ARMP protein may be mixed with pharmaceutically acceptable excipients compatible with the protein. Such excipients may include water, saline, dextrose, glycerol, ethanol and combinations thereof. The immunogenic composition and vaccine may further contain auxiliary substances such as emulsifying agents or adjuvants to enhance effectiveness. Immunogenic compositions and vaccines may be administered parenterally by injection subcataneously or intramuscularly.

The immunogenic preparations and vaccines are administered in such amount as will be therapeutically effective, protective and immunogenic. Dosage depends on the route of administration and will vary according to the size of the host.

The above disclosure generally describes the present invention. A more complete understanding can be obtained by reference to the following specific examples. These examples are described solely for purposes of illustration and are not intended to limit the scope of the invention. Changes in the form and substitution of equivalents are contemplated as circumstances may suggest or render expedient. Although specific terms have been employed herein, such terms are intended in a descriptive sense and not for purposes of limitations.

The microorganism described herein was deposited with the American Type Culture Collection located at 10801 University Boulevard, Manassas, Va. 20110-2209 on Apr. 28, 1995, and assigned accession number ATCC 97124.

Procedure 1. Development of the Genetic, physical "contig" and transcriptional map of the minimal co-segregating region The CEPH MegaYAC and the RPCI PAC human total genomic DNA libraries were searched for clones containing genomic DNA fragments from the AD3 region of chromosome 14q24.3 using oligonucleotide probes for each of the ## SSR marker loci used in the genetic linkage studies as well as ## additional markers depicted in FIG. 1 (Albertsen et al., 1990; Chumakov et al., 1992; Ioannu et al., 1994). The genetic map distances between each marker are depicted above the contig, and are derived from published data (NIH/CEPH Collaborative Mapping Group, 1992; Wang, 1992; Weissenbach, J et al., 1992; Gyapay, G et al., 1994). Clones recovered for each of the initial marker loci were arranged into an ordered series of partially overlapping clones ("contig") using four independent methods. First, sequences representing the ends of the YAC insert were isolated by inverse PCR (Riley at al., 1990), and hybridized to Southern blot panels containing restriction digests of DNA from all of the YAC clones recovered for all of the initial loci in order to identify other YAC clones bearing overlapping sequences. Second, inter-Alu PCR was performed on each YAC, and the resultant band patterns were compared across the pool of recovered YAC clones in order to identify other clones bearing overlapping sequences (Bellamne-Chartelot et al., 1992; Chumakov et al., 1992). Third, to improve the specificity of the Alu-PCR fingerprinting, we restricted the YAC DNA with HaeIII or RsaI, amplified the restriction products with both Alu and L1H consensus primers, and resolved the products by polyacrylamide gel electrophoresis. Finally, as additional STSs were generated during the search for transcribed sequences, these STSs were also used to identify overlaps.

The resultant contig was complete except for a single discontinuity between YAC932C7 bearing D14S53 and YAC746B4 containing D14S61. The physical map order of the STSs within the contig was largely in accordance with the genetic linkage map for this region (NIH/CEPH Collaborative Mapping Group, 1992; Wang, Z, Weber, J. L., 1992; Weissenbach, J et al., 1992; Gyapay, G et al., 1994). However, as with the genetic maps, we ware unable to unambiguously resolve the relative order of the loci within the D14S43/D14S71 cluster and the D14S76/D14S273 cluster. PAC1 clones suggest that D14S277 is telomeric to D14S268, whereas genetic maps have suggested the reverse order. Furthermore, a few STS probes failed to detect hybridization patterns in at least one YAC clone which, on the basis of the most parsimonious consensus physical map and from the genetic map, would have been predicted to contain that STS. For instance, the D14S268 (AFM265) and RSCAT7 STSs are absent from YAC788H12. Because these results were reproducible, and occurred with several different STS markers, these results most likely reflect the presence of small interstitial deletions within one of the YAC clones.

Procedure 2. Cumulative two-point lod scores for chromosome 14q24.3 markers.

Genotypes at each polymorphic microsatellite marker locus were determined by PCR from 100 ng of genomic DNA of all available affected and unaffected pedigree members as previously described (St George-Hyslop, P at al., 1992) using primer sequences specific for each microsatellite locus (Weissenbach, J et al., 1992; Gyapay, G et al., 1994). The normal population frequency of each allele was determined using spouses and other neurologically normal subjects from the same ethnic groups, but did not differ significantly from those established for mixed Caucasian populations (Weissenbach, J et al., 1992; Gyapay, G et al., 1994). The maximum likelihood calculations assumed an age of onset correction, marker allele frequencies derived from published series of mixed Caucasian subjects, and an estimated allele frequency for the AD3 mutation of 1:1000 as previously described (St George-Hyslop, P et al., 1992). The analyses were repeated using equal marker allele frequencies, and using phenotype information only from affected pedigree members as previously described to ensure that inaccuracies in the estimated parameters used in the maximum likelihood calculations did not misdirect the analyses (St George-Hyslop, P et al., 1992). These supplemental analyses did not significantly alter either the evidence supporting linkage, or the discovery of recombination events.

Procedure 3. Haplotypes between flanking markers segregated with AD3 in FAD pedigrees Extended haplotypes between the centro meric and telomeric flanking markers on the parental copy of chromosome 14 segregating with AD3 in fourteen early onset FAD pedigrees (pedigrees NIH2, MGH1, Torl.1, FAD4, FAD1, MEX1, and FAD2 show pedigree specific lod scores≧+3.00 with at least one marker between D14S258 and D14S53). Identical partial haplotypes (boxed) are observed in two regions of the disease bearing chromosome segregating in several pedigrees of similar ethnic origin. In region A, shared alleles are seen at D14S268 ("B": allele size=126 bp, alleles frequency in normal Caucasians=0.04; "C": size=124 bp, frequency=0.38);, D14S277, ("B": size=156 bp, frequency=0.19; "C"; size=154 bp, frequency=0.33); and RSCAT6 ("D": size=111 bp, frequency 0.25; "E": size=109 bp, frequency=0.20; "F": size=107 bp, frequency=0.47). In region B, alleles of identical size are observed at D14S43 ("A": size=193 bp, frequency=0.01; "D": size=187 bp, frequency=0.12; "E": size=185 bp, frequency=0.26; "I": size=160 bp, frequency=0.38); D14S273 ("3": size=193 bp, frequency=0.38; "4" size=191 bp, frequency=0.16; "5": size=189 bp, frequency=0.34; "6": size=187 bp, frequency=0.02) and D14S76 ("1": size=bp, frequency=0.01; "5": size=bp, frequency=0.38; "6": size=bp, frequency=0.07; "9": size=bp, frequency=0.38). The ethnic origins of each pedigree are abbreviated as: Ashk=Ashkenazi Jewish; Ital=Southern Italian; Angl=Anglo-Saxon-Celt; FrCan=French Canadian; Jpn=Japanese; Mex=Mexican Caucasian; Ger= German; Am=American Caucasian. The type of mutation detected is depicted by the amino acid substitution and putative codon number or by ND where no mutation has been detected because a comprehensive survey has not been undertaken due to the absence of a source of mRNA for RT-PCR studies.

Procedure 4. Recovery of transcribed sequences from the AD3 interval.

Putative transcribed sequences encoded in the AD3 interval were recovered using either a direct hybridization method in which short cDNA fragments generated from human brain mRNA were hybridized to immobilized cloned genomic DNA fragments (Rommens, J M et al., 1993). The resultant short putatively transcribed sequences were used as probes to recover longer transcripts from human brain cDNA libraries (Stratagene, La Jolla). The physical location of the original short clone and of the subsequently acquired longer cDNA clones were established by analysis of the hybridization pattern generated by hybridizing the probe to Southern blots containing a panel of EcoRI digested total DNA samples isolated from individual YAC clones within the contig. The nucleotide sequence of each of the longer cDNA clones was determined by automated cycle sequencing (Applied Biosystems Inc., CA), and compared to other sequences in nucleotide and protein databases using the blast algorithm (Altschul, S F et al., 1990). Accession numbers for the transcribed sequences in this report are: L40391, L40392, L40393, L40394, L40395, L40396, L40397, L40398, L40399, L40400, L40401, L40402, and L40403.

Procedure 5. Locating mutations in the ARMP gene using restriction enzymes.

The presence of Ala 246 Glu mutation which creates a DdeI restriction site was assayed in genomic DNA by PCR using the end labelled primer 849 (5'-atctacggcaggcatatct-3') SEQ ID No: 129 and the unlabelled primer 892 (5'-tgaaatcacagccaagatgag-3') SEQ ID No: 130 to amplify an 84 bp genomic exon fragment using 100 ng of genomic DNA template, 2 mM $MgCl_2$, 10 pMoles of each primer, 0.5 U Taq polymerase, 250 uM dNTPs for 30 cycles of 95° C.×20 seconds, 60° C.×20 seconds, 72° C.×5 seconds. The products were incubated with an excess of DdeI for 2 hours according to the manufacturers protocol, and the resulting restriction fragments were resolved on a 6% nondenaturing polyacrylamide gel and visualized by autoradiography. The presence of the mutation was inferred from the cleavage of the 84 bp fragment to due to the presence of a DdeI restriction site. All affected members of the FAD1 pedigree (filled symbols) and several at-risk members ("R") carried the DdeI site. None of the obligate escapees (those individuals who do not get the disease, age >70 years), and none of the normal controls carried the DdeI mutation.

Procedure 6. Locating mutation in the ARMP gene using allele specific oligonucleotides.

The presence of the Cys 410 Tyr mutation was assayed using allele specific oligonucleotides. 100 ng of genomic DNA was amplified with the exonic sequence primer 885 (5'-tggagactggaacacaac-3') SEQ ID NO: 127 and the opposing intronic sequence primer 893 (5'-gtgtggccagggtagagaact-3') SEQ ID: 128 using the above reaction conditions except 2.5 mM $MgCl_2$, and cycle conditions of 94° C.×20 seconds, 58° C.×20 seconds, and 72° C. for 10 seconds). The resultant 216 bp genomic fragment was denatured by 10-fold dilution in 0.4M NaOH, 25 mM EDTA, and was vacuum slot-botted to duplicate nylon membranes. The end-labelled "wild type" primer 890 (5'-ccatagcctGtttcgtagc-3') Seq ID No: 131 and the end-labelled "mutant" primer 891 (5'-ccatagectAtttcgtagc-3') SEQ ID No: 132 were hybridized to separate copies of the slot-blot filters in 5×SSC, 5×Denhardt's, 0.5% SDS for 1 hour at 48° C., and then washed successively in 2×SSC at 23° C. and 2×SSC, 0.1% SDS at 50° C. and then exposed to X-ray film. All testable affected members an wall an some at-risk members of the AD3 (shown) and NIH2 pedigrees (not shown) possessed the Cys 410 Tyr mutation. Attempts to detect the Cys 410 Tyr mutation by SSCP revealed that a common intronic sequence polymorphism migrated with the same SSCP pattern.

Procedure 7. Northern hybridization demonstrating the expression of ARMP protein mRNA in a variety of tissues.

Total cytoplasmic RNA was isolated from various tissue samples (including heart, brain and different regions of, placenta, lung, liver, skeletal muscle, kidney and pancreas) obtained from surgical pathology using standard procedures such as CsCl purification. The RNA was then electrophoresed on a formaldehyde gel to permit size fractionation. The nitrocellulose membrane was prepared and the RNA was then transferred onto the membrane. $^{32}$P-labelled cDNA probes were prepared and added to the membrane in order for hybridization between the probe the RNA to occur. After washing, the membrane was wrapped in plastic film and placed into imaging cassettes containing X-ray film. The autoradiographs were then allowed to develop for one to several days. The positions of the 28S and 18S rRNA bands are indicated. Sizing was established by comparison to standard RNA markers. Analysis of the autoradiographs revealed a prominent band at 3.0 kb in size. These northern blots demonstrated the ARMP gene is expressed in all of the tissues examined.

Although preferred embodiments of the invention have been described herein in detail, it will be understood by those skilled in the art that variations may be made thereto without departing from the spirit of the invention or the scope of the appended claims.

Albertsen H M, Abderrahim H, Cann H M, Dausset J, Le Paslier D Cohen D (1990) Construction and characterization of a yeast artificial chromosome library containing seven haploid human genome equivalents. *Proc.Natl.Acad.Sci.USA* 97: 4256–4260.

Altschul S F, Gish W, Miller W, Myers E W Lipman D (1990) Basic local alignment search tool. *J.Mol.Biol.* 215: 403–410.

Bellamne-Chartelot C, Lacroix R, Ougen P, Billault A, Beaufile S, Bertrand S, Georges I, Glibert F, Gros I, Lucotte G et al (1992) Mapping the whole human genome by fingerprinting YACs. *Cell* 70: 1059–1068.

Bergamini L Pineesi L., Rainero, I., Brunetti, E., Cerratta, P., Consentino, L., Vaula, G., Bruni, A. C., Ermio, C., Gei, G. (1991) Familial Alzheimers Disease: evidence for clincal and genetic heterogeneity. *Acta Neurol.* 13: 534–538.

Chartier-Harlin M-C, Crawford F, Holden H, Warren A, Hughes D, Fidani L, Goate A, Rossor M, Hardy J Mullan M (1991) Early onset Alzheimer's Disease caused by mutations at codon 717 of the B-amyloid gene. *Nature* 353: 844–846.

Chumakov I, Regault P, Guillou S, Ougen P,. Billault A, Guasconi G, Gervy P, Le Gall I, Soularue P Grinas L (1992) Continuum of overlapping clones spanning the entire human chromosome 21. *Nature* 359: 380–387.

Chumakov I M, Le Gall I, Billault A, Ougen P, Soularue P, Guillou S, Regault P, Bui H, De Tand M F, Barrillot E et al (1992) Isolation of chromosome 21 specific yeast artificial chromosomes from a total human genome library. *Nature Genet.* 1: 222–225.

Church D M, Stotler C J, Rutter J L, Murrell J R, Trofatter J A Buckler A J (1994) Isolation of genes from complex sources of mammalian genomic DNA using exon amplification. *Nature Genetics* 6: 98–105.

Foncin J-F, Salmon D, Supino-Viterbo V, Feldman R G, Macchi G, Mariotti P, Scopetta C, Caruso G Bruni A C (1985) Alzheimer's Presenile dementia transmitted in an extended kindred. *Rev. Neurol.* (Paris) 141: 194–202.

Frommelt P, Schnabel R, Kuhne W, Nee L E Polinsky R J (1991) Familial Alzheimer Disease: a large multigenerational German kindred. *Alzheimer Dis. Assoc. Disorders* 5: 36–43.

Goate A M, Chartier-Harlin M-C, Mullan M, Brown J, Crawford F, Fidani L, Guiffra L, Haynes A Hardy J A (1991) Segregation of a missense mutation in the amyloid precursor protein gene with Familial Alzheimer Disease. *Nature* 349: 704–706.

Goudsmit J, White B J, Weitkamp L R, Keats B J, Morrow C H Gadjusek D C (1981) Familial Alzheimer's Disease in two kindreds of the same geographic origin: a clinical and genetic study. *J. Neurol. Sci.* 49: 79–89

Gyapay G, Morissette J, Vignal A, Dib C, Fizames C, Millasseau P, Marc S, Bernardi G, Lathrop M Weissenbach J (1994) The 1993–94 Genethon human linkage map *Nature Genetics* 7: 246–339.

Ioannu P A, Amemiya C T, Garnes J, Kroisel P M, Shizuya H, Chen C, Batzer M A de Jong P J (1994) A new bacteriophage P1-derived vector for the propagation of large human DNA fragments. *Nature Genetics* 6: 84–89.

Karlinsky H, Vaula G, Haines J L, Ridgley J, Bergeron C, Mortilla M, Tupler R, Percy M, Robitaille Y, Crapper MacLachlan D R St George-Hyslop P (1992) Molecular and prospective phenotypic characterization of a pedigree with Familial Alzheimer Disease and a missense mutation in codon 717 of the B-Amyloid Precursor Protein (APP) gene. *Neurology* 42: 1445–1453.

Katzman R (1986) Alzheimer's Disease *N. Eng.J.Med.* 314:(15) 964–973.

Liu Q Sommer S S (1995) Restriction endonuclease fingerprinting (REF): A sensitive method for screening mutations in long contiguous segments of DNA. *BioTechniques* in the press:

Mullan M J, Crawford F, Axelman K al e (1992) A pathogenic mutation for probable Alzheimer's Disease in the APP gene at the N-terminus of B-amyloid. *Nature Genetics* 1: 345–347.

Murrell J, Farlow M, Ghetti B Benson M D (1991) A mutation in the amyloid precursor protein associated with hereditary Alzheimer's Disease. *Science* 254: 97–99.

Nee L, Polinsky R J, Eldridge R, Weingartner H, Smallberg S Ebert M (1983) A family with histologically confirmed Alzheimer Disease. *Arc. Neurol.* 40: 203–208.

NIH/CEPH Collaborative Mapping Group (1992) A comprehensive Genetic Linkage Map of the Human Genome. *Science* 258: 67–86.

Pericak-vance M A, Yamoaka L H Haynes C S (1988) Genetic Linkage Studies in Alzheimer's Disease Families *Exp.Neurol.* 102: 271–279.

Pollen D (1993). Hannah's Heirs: the quest for the genetic origins of Alzheimer's disease. Oxford, Oxford University Press.

Riley J, Ogilvie D, Finnear R, Jenner D, Powell B, Anand R, Smith J C Markham A F (1990) A novel, rapid method for the isolation of terminal sequences from yeast artificial chromosome clones. *Nucl. Acid Res.* 18: 2887–2890.

Rogaev E I, Lukiw W J, Vaula G, Haines J L, Rogaeva E A, Tsuda T, Alexandrova N St George-Hyslop P (1993) Analysis of the cFOS gene on chr 14 and the 5' promoter of the Amyloid Precursor Protein gene in Familial Alzheimer's Disease. *Neurology* 43: 2275–2279.

Rommens J M, Lin B, Hutchinson G B, Andrew S E, Goldberg Y P, Glaves M L, Graham R, Lai V, McArthur J, Nasir J, Thellman J, McDonald H, Kalchman M, Clarke L A, Schappert K Hayden M R (1993) A transcription map of the region containing the Huntington Disease gene. *Hum. Molec. Genet.* 2: 901–907.

Saleeba J A Cotton R G (1993) Chemical Cleavage of mismatch to detect mutations. *Methods in Enzymology* 217: 285–295.

Saunders A, Strittmatter W J, Schmechel S, St George-Hyslop P, Pericak-Vance M, Joo S H, Rosi B L, Gusella J F, Crapper-McLachlan D, Growden J, Alberts M J, Hulette C, Crain B, Goldgaber D Roses A D (1993) Association of Apoliprotein E allele e4 with the late-onset familial and sporadic Alzheimer Disease. *Neurology* 43: 1467–1472.

Schellenberg G D, Bird T D, Wijsman E M, Orr H T, Anderson L, Nemens E, White J A Bonnycastle L (1992) Genetic Linkage evidence for a familial Alzheimer's Disease locus on chr 14. *Science* 258: 668–670.

Schellenberg G D, Payami H, Wijeman E M, Orr H T, Goddard K A, Anderson L, Nemen E, White J A, Alonso M E Ball M J (1993) Chromosome 14 and late onset FAD. *Am.J.Hum.Genet.* 53: 619–628.

George-Hyslop P, Haines J, Rogaev E, Mortilla M, Vaula G, Pericak-Vance M, Foncin J-F, Montesi M, Bruni A, Sorbi S, Rainero I, Pinessi I, Pollen D, Polinsky R, Nee L, Kennedy J, Macciardi F, Rogeava E, Liang Y, Alexandrova N, Lukiw W, Schlumpf K, Tsuda T, Farrer L, Cantu J-M, Duara R, Amaducci L, Bergamini L, Gusella J, Roses A Crapper MacLachlan D (1992) Genetic Evidence for a novel Familial Alzheimer Disease gene on chromosome 14. *Nature Genetics* 2: 330–334.

St George-Hyslop P H, Haines J L, Farrer L A, van Broeckhoven C, Goate A M, Crapper-McLachlan D R al. e (1991) Genetic Linkage studies suggest that Alzheimer's Disease is not a single homogeneous disorder. *Nature* 347: 194–197.

Strittmatter W J, Saunders A M, Schmechel D, Goldgaber D, Roses A D al. e (1993) Apolipoprotein E: high affinity binding to B/A4 amyloid and increased frequency of type 4 allele in Familial Alzheimers Disease. *Proc.Natl.Acad..Sci.USA* 90: 1977–1981.

Van Broeckhoven C, Backhovens H, Cruts M, De Winter G, Bruyland M, Cras P Martin J-J (1992) Mapping of a gene predisposing to early-onset Alzheimer's Disease to chromosome 14q24.3 *Nature Genetics* 2: 335–339.

Wang Z Weber, J. L. (1992) Continuous Linkage Map of human chromosome 14 short tandem repeat polymorphisms Genomics 13: 532–536.

Weissenbach J, Gyapay G, Dib C, Vignal A, Morisette J, Millasseau P, G. V Lathrop M (1992) A second generation linkage map of the human genome. *Nature* 359: 794–798.

Wong L, Liang Y, Tsuda T, Fong Q, Galway G, Alexandrova N, Rogeava E, Lukiw W, Smith J, Rogaev E, Crapper MacLachlan D St George-Hyslop P (1993) Mutation of the gene for the human lysosomal serine protease Cathepsin G is not the cause of aberrant APP processing in Familial Alzheimer Disease. *Neorosci. Lett.* 152: 96–98.

TABLE 1

| LOCUS | \multicolumn{7}{c}{RECOMBINATION FRACTION (θ)} |
|---|---|---|---|---|---|---|---|
|  | 0.00 | 0.05 | 0.10 | 0.15 | 0.20 | 0.30 | 0.40 |
| D14S63 | -∞ | 1.54 | 3.90 | 4.38 | 4.13 | 2.71 | 1.08 |
| D14S258 | -∞ | 21.60 | 19.64 | 17.19 | 14.50 | 8.97 | 3.81 |
| D14S77 | -∞ | 15.18 | 15.53 | 14.35 | 12.50 | 7.82 | 2.92 |
| D14S71 | -∞ | 15.63 | 14.14 | 12.19 | 10.10 | 5.98 | 2.39 |
| D14S43 | -∞ | 19.36 | 17.51 | 15.27 | 12.84 | 7.80 | 3.11 |
| D14S273 | -∞ | 12.30 | 11.52 | 10.12 | 8.48 | 5.04 | 1.91 |
| D14S61 | -∞ | 26.90 | 24.9Z | 22.14 | 18.98 | 12.05 | 5.07 |
| D14S53 | -∞ | 11.52 | 11.41 | 10.39 | 8.99 | 5.73 | 2.51 |
| D14S48 | -∞ | 0.50 | 1.05 | 1.14 | 1.04 | 0.60 | 0.18 |

TABLE 2

| LOCUS | \multicolumn{13}{c}{PEDIGREE ID} |
|---|---|---|---|---|---|---|---|---|---|---|---|---|---|
|  | NIH2 | MGH1 | TOR1.1 | FAD4 | RB | FAD1 | MG12 | BOW | COOK | Tor42 | QUE | MEX1 | GER 603 |
| D14S63 | 1 | 4 | 7 | 4 |  | 5 |  |  |  |  | 9 | 2 |  |
| D14S258 | 6 | 6 | 8 | 7 | 4 | 5 | 5 | 6 | 6 | 7 | 6 | 7 | 6 |
| D14S268 | C | C | B | B | C | C | C | C | C | C | B | C | C |
| D14S277 | C | C | C | C | C | C | C | C | C | A | C | B | B |
| RSCAT6 | D | D | E | E | F | E | E | D/F | E | B | E | F | D |
| D14S77 | Y | Y | K | S |  | P | P | K | H | C | U | F | A |
| D14S71 | 7 | 7 | 1 | 5 | 7 | 7 |  | 6 | 7 | 3 | 7 | 2 | 6 |
| D14S43 | C | C | I | I | I | E | D | I | I | C | I | D | C |
| D14S273 | 6 | 6 | 5 | 5 | 5 | 4 | 4 | 4 | 6 | 6 | 6 | 5 | 3 |
| D14S76 | 5 | 5 | 5 | 5 | 5 | 6 | 9 | 9 |  | 9 | 1 | 5 | 5 |
| D14S61 | E | E | G | F |  | I |  |  |  | D |  | L | F |
| D14S53 | F | F | C | F | F | J | C | F | E | J | D | F | F |
| ETHNIC ORIGIN | Ashk | Ashk | Ital | Ital | Ital | Angl | Angl | Angl | Angl | FrCan | FrCan | Mex | Ger Ar |
| MUTATION | C4/0Y | C4/0Y | M/462 | M/462 | ND | A2465 | ND | ND | ND | ND | ND | ND | ND |

```
                              DNASIS
              Simple Homology Region [armp.con [Frame 1]]

NO. Target File              Key   Target  Overlap  Match   Percentage
  1  marmp.con/long [Frame 1]  1      1       467     465      99.57%

1        10        20        30        40        50        60        70
 N- MTELPAPLSYFQNAQMSEDNHLSNTVRSQNDNRERQEHNDRRSLGHPEPLSNGRPQGNSRQVVEQDEEED
    **********************************************************************
 N- MTEIPAPLSYFQNAQMSEDSHSSSAIRSQNDSQERQQQHDRQRLDNPEPISNGRPQSNSRQVVEQDEEED
       1        10        20        30        40        50        60        70

71        80        90       100       110       120       130       140
    EELTLKYGAKHVIMLFVPVTLCMVVVVATIKSVSFYTRKDGQLIYTPFTEDTETVGQRALHSILNAAIMI
    **********************************************************************
      71        80        90       100       110       120       130       140

141       150       160       170       180       190       200       210
    SVIVVMTILLVVLYKYRCYKVIHAWLIISSLLLLFFFSFIYLGEVFKTYNVAVDYITVALLIWNLGVVGM
    **********************************************************************
     141       150       160       170       180       190       200       210

211       220       230       240       250       260       270       280
    ISIHWKGPLRLQQAYLIMISALMALVFIKYLPEWTAWLILAVISVYDLVAVLCPKGPLRMLVETAQERNE
    **********************************************************************
    ISIHWKGPLRLQQAYLIMISALMALVFIKYLPEWTAWLILAVISVYDLVAVLCPKGPLRMLVETAQERNE
     211       220       230       240       250       260       270       280
```

-continued

```
                            DNASIS
            Simple Homology Region [armp.con [Frame 1]]

NO.  Target File            Key   Target   Overlap   Match   Percentage
 1   marmp.con/long [Frame 1]  1      1       467     465      99.57%

281        290       300       310       320       330       340       350
   TLFPALITSSTMVWLVNMAEGDPEAQRRVSKNSKYNAESTERESQDTVAENDDGGFSEEWEAQRDSHLGP
   ******************************************************************
   TLFPALITSSTMVWLVNMAEGDPEAQRRVPKNPKYNTQRAERETQDSGSGNDDGGFSEEWEAQRDSHLGP
   281        290       300       310       320       330       340       350

351        360       370       380       390       400       410       420
   HRSTPESRAAVQELSSSILAGEDPEERGVKLGLGDFIFYSVLVGKASATASGDWNTTIACFVAILIGLCL
   ******************************************************************
   HRSTPESRAAVQELSSSILTSEDPEERGVKLGLGDFIFYSVLVGKASATASGDWNTTIACXVAILIGLCL
   351        360       370       380       390       400       410       420

421        430       440       450       460
   TLLLLAIFKKALPALPISITFQLVFYPATDYLVQPFMDQLAFHQFYI -C
   *********************************************
   XLLLLAIYKKGXPAXPISITFGFVFXFATDYLVQPFMDQLAFHQFYI -C
   421        430       440       450       460
```

TABLE 4

| DOMAINS (AMINO ACID RESIDUE) | FUNCTIONAL CHARACTERISTICS |
|---|---|
| 82–100 AA | HYDROPHOBIC |
| 132–154 AA | " |
| 160–183 AA | " |
| 195–213 AA | " |
| 221–238 AA | " |
| 244–256 AA | " |
| 281–299 AA | " |
| 404–428 AA | " |
| 431–449 AA | " |
| 115–119 AA (YTPF) | Phosphorylation Site |
| 353–356 AA (STPC) | " |
| 300–385 AA | ACID RICH DOMAIN POSSIBLE METAL BINDING DOMAIN. |

TABLE 4-continued

| ANTIGENIC SITES INCLUDING AMINO ACID RESIDUE |
|---|
| 7–44 |
| 46–48 |
| 50–60 |
| 66–67 |
| 107–111 |
| 120–121 |
| 125–126 |
| 155–160 |
| 185–189 |
| 214–223 |
| 220–230 |
| 240–245 |
| 267–269 |
| 273–282 |
| 300–370 |
| 400–420 |

TABLE 5

| MUTATION | ENZYME (effect of mutation) | AMPLIFICATION 0440 #1 | AMPLIFICATION 0440 #2 | ALLELE SPECIFIC 0440 |
|---|---|---|---|---|
| M146LEU | Bsphl (destroy) | 910 (170-S182 F) TCACAGAAGATA CCGAGACT (SEQ ID NO: 133) | 911 (170-S182) R CCCAACCATAAGA AGAACAG (SEQ ID NO:139) | |
| MIS 163 Ary | NIa III (destroy) | 927 (intronic) TCTGTACITTTT AAGGGTTGTG (SEQ ID NO:134) | 928 ACTTCAGAGTAATT CATCANCA (SEQ ID NO:140) | |
| Ala 246 | DIc I (create) | 849* GACTCCAGCAGG CATATCT (SEQ ID NO:135) | 892 TGAAATCACAGCC AAGATGAG (SEQ ID NO:141) | |
| Leu 286 Val | (Pvu II) (create) | 952 GATGAGACAAGT NCCNTGAA (SEQ ID NO:136) | 951 CACCCATTTACAAG TTTAGC (SEQ ID NO:142) | |

TABLE 5-continued

| MUTATION | ENZYME (effect of mutation) | AMPLIFICATION 0440 #1 | AMPLIFICATION 0440 #2 | ALLELE SPECIFIC 0440 |
|---|---|---|---|---|
| Cys 410 Tys | Allele specific iligo | 945 TTAGTGGCTGIT TNGTGTCC (SEQ ID NO:137) 893 GTGTGGCCAGGG TAGAGAACT (SEQ ID NO:138) | 885 TGGAGACTGGAAC ACAAC (SEQ ID NO:143) | CCATAGCCTGTTTCGT AGC (SEQ ID NO:144) 890 = WT CCATAGCCTATTTCGT AGC (SEQ ID NO:145) 891 = MUT |

What is claimed is:

1. An isolated polynucleotide encoding a mammalian Alzheimer's Related Membrane Protein (ARMP) having greater than 95% homology with SEQ ID NO:2 or SEQ ID NO:4.

2. The isolated polynucleotide of claim 1, wherein the polynucleotide is a polydeoxyribonucleotide.

3. The isolated polynucleotide of claim 1, wherein the polynucleotide is a polyribonucleotide.

4. The isolated polynucleotide of claim 1, wherein the ARMP is a human ARMP.

5. The isolated polynucleotide of claim 4, wherein the ARMP comprises the amino acid sequence of SEQ ID NO:2 or the complement of said polynucleotide.

6. The isolated polynucleotide of claim 5, wherein the polynucleotide is a polydeoxyribonucleotide.

7. The isolated polynucleotide of claim 5, wherein the polynucleotide is a polyribonucleotide.

8. The isolated polynucleotide of claim 5, comprising the nucleic acid sequence of SEQ ID NO:1.

9. The isolated polynucleotide of claim 4, wherein the polynucleotide differs from SEQ ID NO:1 by one or more nucleic acid substitutions at a position selected from the group consisting of 685, 747, 986, 1105, and 1478 of SEQ ID NO:1 or wherein the ARMP differs from SEQ ID NO:2 by one or more amino acid substitutions at a position selected from the group consisting of 146, 163, 246, 286, and 410 of SEQ ID NO:2.

10. The isolated polynucleotide of claim 9, wherein the substitution is a C at position 685 of SEQ ID NO:1.

11. The isolated polynucleotide of claim 9, wherein the substitution is a G at position 747 of SEQ ID NO:1.

12. The isolated polynucleotide of claim 9, wherein the substitution is an A at position 986 of SEQ ID NO:1.

13. The isolated polynucleotide of claim 9, wherein the substitution is a G at position 1105 of SEQ ID NO:1.

14. The isolated polynucleotide of claim 9, wherein the substitution is an A at position 1478 of SEQ ID NO:1.

15. The isolated polynucleotide of claim 9, wherein the ARMP has a substitution at position 146 of SEQ ID NO:2.

16. The isolated polynucleotide of claim 15, wherein the substitution is a Leu at position 146 of SEQ ID NO:2.

17. The isolated polynucleotide of claim 9, wherein the ARMP has a substitution at position 163 of SEQ ID NO:2.

18. The isolated polynucleotide of claim 17, wherein the substitution is an Arg at position 163 of SEQ ID NO:2.

19. The isolated polynucleotide of claim 9, wherein the ARMP has a substitution at position 246 of SEQ ID NO:2.

20. The isolated polynucleotide of claim 19, wherein the substitution is a Glu at position 246 of SEQ ID NO:2.

21. The isolated polynucleotide of claim 9, wherein the ARMP has a substitution at position 286 of SEQ ID NO:2.

22. The isolated polynucleotide of claim 21, wherein the substitution is a Val at position 286 of SEQ ID NO:2.

23. The isolated polynucleotide of claim 9, wherein the ARMP has a substitution at position 410 of SEQ ID NO:2.

24. The isolated polynucleotide of claim 23, wherein the substitution is a Tyr at position 410 of SEQ ID NO:2.

25. The isolated polynucleotide of claim 9, wherein the polynucleotide is a polydeoxyribonucleotide.

26. The isolated polynucleotide of claim 9, wherein the polynucleotide is a polyribonucleotide.

27. The isolated polynucleotide of claim 1, wherein the ARMP is a mouse ARMP.

28. The isolated polynucleotide of claim 27, wherein the ARMP comprises the amino acid sequence of SEQ ID NO:4 or the complement of said polynucleotide.

29. The isolated polynucleotide of claim 28, wherein the polynucleotide is a polydeoxyribonucleotide.

30. The isolated polynucleotide of claim 28, wherein the polynucleotide is a polyribonucleotide.

31. The isolated polynucleotide of claim 28, wherein the polynucleotide comprises the nucleic acid sequence of SEQ ID NO:3.

32. A vector comprising an isolated polynucleotide encoding a mammalian Alzheimer's Related Membrane Protein (ARMP) having greater than 95% homology with SEQ ID NO:2 or SEQ ID NO:4.

33. A host cell comprising the vector of claim 32.

34. A method of producing ARMP comprising culturing the host cell of claim 33 under conditions such that the polynucleotide encoding ARMP is expressed to detectable levels.

35. The vector of claim 32, wherein the mammalian ARMP is a mutant ARMP.

36. A host cell comprising the vector of claim 35.

37. The vector of claim 35, wherein the ARMP differs from SEQ ID NO:2 by one or more amino acid substitutions at a position selected from the group consisting of 146, 163, 246, 286, and 410 of SEQ ID NO:2.

38. A host cell comprising the vector of claim 37.

39. A method of producing ARMP comprising culturing the host cell of claim 38 under conditions such that the polynucleotide encoding ARMP is expressed to detectable levels.

40. The vector of claim 37, wherein the substitution is a Leu at position 146 of SEQ ID NO:2, an Arg at position 163 of SEQ ID NO:2, a Glu at position 246 of SEQ ID NO:2, a Val at position 286 of SEQ ID NO:2, or a Tyr at position 410 of SEQ ID NO:2.

41. A host cell comprising the vector of claim 40.

42. The vector of claim 32, wherein the polynucleotide encodes the amino acid sequence of SEQ ID NO:2.

43. A host cell comprising the vector of claim 42.

44. The vector of claim 32, wherein the polynucleotide encodes the amino acid sequence of SEQ ID NO:4.

45. A host cell comprising the vector of claim 44.

46. An isolated polynucleotide sequence encoding the human ARMP encoded by the polynucleotide sequence contained in ATCC Accession No. 97124.

* * * * *

UNITED STATES PATENT AND TRADEMARK OFFICE
CERTIFICATE OF CORRECTION

PATENT NO. : 6,531,586 B1
DATED : March 11, 2003
INVENTOR(S) : Peter H. St. George-Hyslop et al.

It is certified that error appears in the above-identified patent and that said Letters Patent is hereby corrected as shown below:

<u>Title page,</u>
Item [73], Assignee, delete "The Hospital for Sick Children"

Signed and Sealed this

Thirtieth Day of December, 2003

JAMES E. ROGAN
*Director of the United States Patent and Trademark Office*

SEQUENCE LISTING (1) GENERAL INFORMATION:

(iii) NUMBER OF SEQUENCES: 155

(2) INFORMATION FOR SEQ ID NO: 1:

(i) SEQUENCE CHARACTERISTICS:
      (A) LENGTH: 2791 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

```
TGGGACAGGC AGCTCCGGGG TCCGCGGTTT CACATCGGAA ACAAAACAGC GGCTGGTCTG      60

GAAGGAACCT GAGCTACGAG CCGCGGCGGC AGCGGGGCGG CGGGGNAAGC GTATACCTAA     120

TCTGGGAGCC TGCAAGTGAC AACAGCCTTT GCGGTCCTTA GACAGCTTGG CCTGGAGGAG     180

AACACATGAA AGAAAGAACC TCAAGAGGCT TTGTTTTCTG TGAAACAGTA TTTCTATACA     240

GTTGCTCCAA TGACAGAGTT ACCTGCACCG TTGTCCTACT TCCAGAATGC ACAGATGTCT     300

GAGGACAACC ACCTGAGCAA TACTGTACGT AGCCAGAATG ACAATAGAGA ACGGCAGGAG     360

CACAACGACA GACGGAGCCT TGGCCACCCT GAGCCATTAT CTAATGGACG ACCCCAGGGT     420

AACTCCCGGC AGGTGGTGGA GCAAGATGAG GAAGAAGATG AGGAGCTGAC ATTGAAATAT     480

GGCGCCAAGC ATGTGATCAT GCTCTTTGTC CCTGTGACTC TCTGCATGGT GGTGGTCGTG     540

GCTACCATTA AGTCAGTCAG CTTTTATACC CGGAAGGATG GGCAGCTAAT CTATACCCCA     600

TTCACAGAAG ATACCGAGAC TGTGGGCCAG AGAGCCCTGC ACTCAATTCT GAATGCTGCC     660

ATCATGATCA GTGTCATTGT TGTCATGACT ATCCTCCTGG TGGTTCTGTA TAAATACAGG     720

TGCTATAAGG TCATCCATGC CTGGCTTATT ATATCATCTC TATTGTTGCT GTTCTTTTTT     780

TCATTCATTT ACTTGGGGGA AGTGTTTAAA ACCTATAACG TTGCTGTGGA CTACATTACT     840

GTTGCACTCC TGATCTGGAA TTTGGGTGTG GTGGAATGA TTTCCATTCA CTGGAAAGGT     900

CCACTTCGAC TCCAGCAGGC ATATCTCATT ATGATTAGTG CCCTCATGGC CCTGGTGTTT     960

ATCAAGTACC TCCCTGAATG GACTGCGTGG CTCATCTTGG CTGTGATTTC AGTATATGAT    1020

TTAGTGGCTG TTTTGTGTCC GAAAGGTCCA CTTCGTATGC TGGTTGAAAC AGCTCAGGAG    1080

AGAAATGAAA CGCTTTTTCC AGCTCTCATT TACTCCTCAA CAATGGTGTG GTTGGTGAAT    1140

ATGGCAGAAG GAGACCCGGA AGCTCAAAGG AGAGTATCCA AAAATTCCAA GTATAATGCA    1200
```

-continued

```
GAAAGCACAG AAAGGGAGTC ACAAGACACT GTTGCAGAGA ATGATGATGG CGGGTTCAGT      1260

GAGGAATGGG AAGCCCAGAG GGACAGTCAT CTAGGGCCTC ATCGCTCTAC ACCTGAGTCA      1320

CGAGCTGCTG TCCAGGAACT TTCCAGCAGT ATCCTCGCTG GTGAAGACCC AGAGGAAAGG      1380

GGAGTAAAAC TTGGATTGGG AGATTTCATT TTCTACAGTG TTCTGGTTGG TAAAGCCTCA      1440

GCAACAGCCA GTGGAGACTG GAACACAACC ATAGCCTGTT TCGTAGCCAT ATTAATTGGT      1500

TTGTGCCTTA CATTATTACT CCTTGCCATT TCAAGAAAG CATTGCCAGC TCTTCCAATC       1560

TCCATCACCT TTGGGCTTGT TTTCTACTTT GCCACAGATT ATCTTGTACA GCCTTTTATG      1620

GACCAATTAG CATTCCATCA ATTTTATATC TAGCATATTT GCGGTTAGAA TCCCATGGAT      1680

GTTTCTTCTT TGACTATAAC CAAATCTGGG GAGGACAAAG GTGATTTTCC TGTGTCCACA      1740

TCTAACAAAG TCAAGATTCC CGGCTGGACT TTTGCAGCTT CCTTCCAAGT CTTCCTGACC      1800

ACCTTGCACT ATTGGACTTT GGAAGGAGGT GCCTATAGAA AACGATTTTG AACATACTTC      1860

ATCGCAGTGG ACTGTGTCCT CGGTGCAGAA ACTACCAGAT TTGAGGGACG AGGTCAAGGA      1920

GATATGATAG GCCCGGAAGT TGCTGTGCCC CATCAGCAGC TTGACGCGTG GTCACAGGAC      1980

GATTTCACTG ACACTGCGAA CTCTCAGGAC TACCGGTTAC CAAGAGGTTA GGTGAAGTGG      2040

TTTAAACCAA ACGGAACTCT TCATCTTAAA CTACACGTTG AAAATCAACC CAATAATTCT      2100

GTATTAACTG AATTCTGAAC TTTTCAGGAG GTACTGTGAG GAAGAGCAGG CACCAGCAGC      2160

AGAATGGGA ATGGAGAGGT GGGCAGGGGT TCCAGCTTCC CTTTGATTTT TTGCTGCAGA       2220

CTCATCCTTT TTAAATGAGA CTTGTTTTCC CCTCTCTTTG AGTCAAGTCA AATATGTAGA      2280

TGCCTTTGGC AATTCTTCTT CTCAAGCACT GACACTCATT ACCGTCTGTG ATTGCCATTT      2340

CTTCCCAAGG CCAGTCTGAA CCTGAGGTTG CTTTATCCTA AAAGTTTTAA CCTCAGGTTC      2400

CAAATTCAGT AAATTTTGGA AACAGTACAG CTATTTCTCA TCAATTCTCT ATCATGTTGA      2460

AGTCAAATTT GGATTTTCCA CCAAATTCTG AATTTGTAGA CATACTTGTA CGCTCACTTG      2520

CCCCAGATGC CTCCTCTGTC CTCATTCTTC TCTCCCACAC AAGCAGTCTT TTTCTACAGC      2580

CAGTAAGGCA GCTCTGTCGT GGTAGCAGAT GGTCCCACTT ATTCTAGGGT CTTACTCTTT      2640

GTATGATGAA AAGAATGTGT TATGAATCGG TGCTGTCAGC CCTGCTGTCA GACCTTCTTC      2700

CACAGCAAAT GAGATGTATG CCCAAAGCGG TAGAATTAAA GAAGAGTAAA ATGGCTGTTG      2760

AAGCAAAAAA AAAAAAAAAA AAAAAAAAAA A                                    2791
```

(2) INFORMATION FOR SEQ ID NO: 2:

(i) SEQUENCE CHARACTERISTICS:
        (A) LENGTH: 467 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

```
Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60
```

```
Gln Asp Glu Glu Asp Glu Glu Leu Thr Leu Lys Tyr Gly Ala Lys
 65                  70                  75                  80

His Val Ile Met Leu Phe Val Pro Val Thr Leu Cys Met Val Val
                 85                  90                  95

Val Ala Thr Ile Lys Ser Val Ser Phe Tyr Thr Arg Lys Asp Gly Gln
                100                 105                 110

Leu Ile Tyr Thr Pro Phe Thr Glu Asp Thr Glu Thr Val Gly Gln Arg
            115                 120                 125

Ala Leu His Ser Ile Leu Asn Ala Ala Ile Met Ile Ser Val Ile Val
        130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
                180                 185                 190

Val Asp Tyr Ile Thr Val Ala Leu Leu Ile Trp Asn Leu Gly Val Val
            195                 200                 205

Gly Met Ile Ser Ile His Trp Lys Gly Pro Leu Arg Leu Gln Gln Ala
        210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
        290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
                340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
        370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
                420                 425                 430

Pro Ala Leu Pro Ile Ser Ile Thr Phe Gly Leu Val Phe Tyr Phe Ala
            435                 440                 445

Thr Asp Tyr Leu Val Gln Pro Phe Met Asp Gln Leu Ala Phe His Gln
        450                 455                 460

Phe Tyr Ile
465
```

(2) INFORMATION FOR SEQ ID NO: 3:

(i) SEQUENCE CHARACTERISTICS:
        (A) LENGTH: 1929 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

```
ACCANACANC GGCAGCTGAG GCGGAAACCT AGGCTGCGAG CCGGCCGCCC GGGCGCGGAG      60
AGAGAAGGAA CCAACACAAG ACAGCAGCCC TTCGAGGTCT TTAGGCAGCT TGGAGGAGAA     120
CACATGAGAG AAAGAATCCC AAGAGGTTTT GTTTTCTTTG AGAAGGTATT TCTGTCCAGC     180
TGCTCCAATG ACAGAGATAC CTGCACCTTT GTCCTACTTC CAGAATGCCC AGATGTCTGA     240
GGACAGCCAC TCCAGCAGCG CCATCCGGAG CCAGAATGAC AGCCAAGAAC GGCAGCAGCA     300
GCATGACAGG CAGAGACTTG ACAACCCTGA GCCAATATCT AATGGGCGGC CCCAGAGTAA     360
CTCAAGACAG GTGGTGGAAC AAGATGAGGA GGAAGACGAA GAGCTGACAT TGAAATATGG     420
AGCCAAGCAT GTCATCATGC TCTTTGTCCC CGTGACCCTC TGCATGGTCG TCGTCGTGGC     480
CACCATCAAA TCAGTCAGCT TCTATACCCG GAAGGACGGT CAGCTAATCT ACACCCCATT     540
CACAGAAGAC ACTGAGACTG TAGGCCAAAG AGCCCTGCAC TCGATCCTGA ATGCGGCCAT     600
CATGATCAGT GTCATTGTCA TTATGACCAT CCTCCTGGTG GTCCTGTATA AATACAGGTG     660
CTACAAGGTC ATCCACGCCT GGCTTATTAT TTCATCTCTG TTGTTGCTGT TCTTTTTTTC     720
GTTCATTTAC TTAGGGGAAG TATTTAAGAC CTACAATGTC KCCGTGGACT ACGTTACAGT     780
AGCACTCCTA ATCTGGAATT GGGGTGTGGT CGGGATGATT GCCATCCACT GGAAAGGCCC     840
CCTTCGACTG CAGCAGGCGT ATCTCATTAT GATCAGTGCC CTCATGGCCC TGGTATTTAT     900
CAAGTACCTC CCCGAATGGA CCGCATGGCT CATCTTGGCT GTGATTTCAG TATATGATTT     960
GGTGGCTGTT TTATGTCCCA AAGGCCCACT TCGTATGCTG GTTGAAACAG CTCAGGAAAG    1020
AAATGAGACT CTCTTTCCAG CTCTTATCTA TTCCTCAACA ATGGTGTGGT TGGTGAATAT    1080
GGCTGAAGGA GACCCAGAAG CCCAAAGGAG GGTACCCAAG AACCCCAAGT ATAACACACA    1140
AAGAGCGGAG AGAGAGACAC AGGACAGTGG TTCTGGGAAC GATGATGGTG GCTTCAGTGA    1200
GGAGTGGGAG GCCCAAAGAG ACAGTCACCT GGGGCCTCAT CGCTCCACTC CCGAGTCAAG    1260
AGCTGCTGTC CAGGAACTTT CTGGGAGCAT TCTAACGAGT GAAGACCCGG AGGAAAGAGG    1320
AGTAAAACTT GGACTGGGAG ATTTCATTTT CTACAGTGTT CTGGTTGGTA AGGCCTCAGC    1380
AACCGCCAGT GGAGACTGGA ACACAACCAT AGCCTGCTTK GTAGCCATAC TGATCGGCCT    1440
GTGCCTTANA TTACTCCTGC TCGCCATTTA CAAGAAAGGG TNGCCAGCCC NCCCCATCTC    1500
CATCACCTTC GGGTTCGTGT TCTNCTTCGC CACGGATTAC CTTGTGCAGC CCTTCATGGA    1560
CCAACTTGCA TTCCATCAGT TTTATATCTA GCCTTTCTGC AGTTAGAACA TGGATGTTTC    1620
TTCTTTGATT ATCAAAAACA CAAAAACAGA GAGCAAGCCC GAGGAGGAGA CTGGTGACTT    1680
TCCTGTGTCC TCAGCTAACA AAGGCAGGAC TCCAGCTGGA CTTCTGCAGC TTCCTTCCGA    1740
GTCTCCCTAG CCACCCGCAC TACTGGACTG TGGAAGGAAG CGTCTACAGA GGAACGGTTT    1800
CCAACATCCA TCGCTGCAGC AGACGGTGTC CCTCAGTGAC TTGAGAGACA AGGACAAGGA    1860
AATGTGCTGG GCCAAGGAGC TGCCGTGCTC TGCTAGCTTT GGMCCGTGGG CATGGAGATT    1920
TACCCGCAC                                                            1929
```

-continued (2) INFORMATION FOR SEQ ID NO: 4:

(i) SEQUENCE CHARACTERISTICS:
        (A) LENGTH: 467 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Met Thr Glu Ile Pro Ala Pro Leu Ser Tyr Phe Gln Asn Ala Gln Met
1               5                   10                  15

Ser Glu Asp Ser His Ser Ser Ala Ile Arg Ser Gln Asn Asp Ser
            20                  25                  30

Gln Glu Arg Gln Gln Gln His Asp Arg Gln Arg Leu Asp Asn Pro Glu
        35                  40                  45

Pro Ile Ser Asn Gly Arg Pro Gln Ser Asn Ser Arg Gln Val Val Glu
    50                  55                  60

Gln Asp Glu Glu Asp Glu Glu Leu Thr Leu Lys Tyr Gly Ala Lys
65                  70                  75                  80

His Val Ile Met Leu Phe Val Pro Val Thr Leu Cys Met Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Ile Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Xaa
            180                 185                 190

Val Asp Tyr Val Thr Val Ala Leu Leu Ile Trp Asn Trp Gly Val Val
        195                 200                 205

Gly Met Ile Ala Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
    290                 295                 300

Ala Gln Arg Arg Val Pro Lys Asn Pro Lys Tyr Asn Thr Gln Arg Ala
305                 310                 315                 320

Glu Arg Glu Thr Gln Asp Ser Gly Ser Gly Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Gly Ser Ile
```

```
                355                  360                   365
Leu Thr Ser Glu Asp Pro Glu Glu Arg Gly Val Lys Leu Gly Leu Gly
            370                  375                  380

Asp Phe Ile Phe Tyr Ser Val Leu Val Gly Lys Ala Ser Ala Thr Ala
385                  390                  395                  400

Ser Gly Asp Trp Asn Thr Thr Ile Ala Cys Xaa Val Ala Ile Leu Ile
                405                  410                  415

Gly Leu Cys Leu Xaa Leu Leu Leu Ala Ile Tyr Lys Lys Gly Xaa
                420                  425                  430

Pro Ala Xaa Pro Ile Ser Ile Thr Phe Gly Phe Val Phe Xaa Phe Ala
            435                  440                  445

Thr Asp Tyr Leu Val Gln Pro Phe Met Asp Gln Leu Ala Phe His Gln
    450                  455                  460

Phe Tyr Ile
465

(2) INFORMATION FOR SEQ ID NO: 5:

(i) SEQUENCE CHARACTERISTICS:
        (A) LENGTH: 3087 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

GAATTCGGCA CGAGGGAAAT GCTGTTTGCT CGAAGACGTC TCAGGGCGCA GGTGCCTTGG      60

GCCGGGATTA GTAGCCGTCT GAACTGGAGT GGAGTAGGAG AAAGAGGAAG CGTCTTGGGC    120

TGGGTCTGCT TGAGCAACTG GTGAAACTCC GCGCCTCACG CCCCGGGTGT GTCCTTGTCC    180

AGGGGCGACG AGCATTCTGG GCGAAGTCCG CACSCCTCTT GTTCGAGGCG GAAGACGGGG    240

TCTGATSCTT TCTCCTTGGT CGGGMCTGTC TCGAGGCATG CATGTCCAGT GACTCTTGTG    300

TTTGCTGCTG CTTCCCTCTC AGATTCTTCT CACCGTTGTG GTCAGCTCTG CTTTAGGCAN    360

TATTAATCCA TAGTGGAGGC TGGGATGGGT GAGAGAATTG AGGTGACTTT TCCATAATTC    420

AGACCTAATC TGGGAGCCTG CAAGTGACAA CAGCCTTTGC GGTCCTTAGA CAGCTTGGCC    480

TGGAGGAGAA CACATGAAAG AAAGAACCTC AAGAGGCTTT GTTTTCTGTG AAACAGTATT    540

TCTATACAGT TGCTCCAATG ACAGAGTTAC CTGCACCGTT GTCCTACTTC AGAATGCAC     600

AGATGTCTGA GGACAACCAC CTGAGCAATA CTAATGACAA TAGAGAACGG CAGGAGCACA    660

ACGACAGACG GAGCCTTGGC CACCCTGAGC CATTATCTAA TGGACGACCC CAGGGTAACT    720

CCCGGCAGGT GGTGGAGCAA GATGAGGAAG AAGATGAGGA GCTGACATTG AAATATGGCG    780

CCAAGCATGT GATCATGCTC TTTGTCCCTG TGACTCTCTG CATGGTGGTG GTCGTGGCTA    840

CCATTAAGTC AGTCAGCTTT TATACCCGGA AGGATGGGCA GCTAATCTAT ACCCCATTCA    900

CAGAAGATAC CGAGACTGTG GGCCAGAGAG CCCTGCACTC AATTCTGAAT GCTGCCATCA    960

TGATCAGTGT CATTGTTGTC ATGACTATCC TCCTGGTGGT TCTGTATAAA TACAGGTGCT   1020

ATAAGGTCAT CCATGCCTGG CTTATTATAT CATCTCTATT GTTGCTGTTC TTTTTTTCAT   1080

TCATTTACTT GGGGGAAGTG TTTAAAACCT ATAACGTTGC TGTGGACTAC ATTACTGTTG   1140

CACTCCTGAT CTGGAATTTG GGTGTGGTGG GAATGATTTC CATTCACTGG AAAGGTCCAC   1200

TTCGACTCCA GCAGGCATAT CTCATTATGA TTAGTGCCCT CATGGCCCTG GTGTTTATCA   1260

AGTACCTCCC TGAATGGACT GCGTGGCTCA TCTTGGCTGT GATTTCAGTA TATGATTTAG   1320
```

-continued

```
TGGCTGTTTT GTGTCCGAAA GGTCCACTTC GTATGCTGGT TGAAACAGCT CAGGAGAGAA    1380

ATGAAACGCT TTTTCCAGCT CTCATTTACT CCTCAACAAT GGTGTGGTTG GTGAATATGG    1440

CAGAAGGAGA CCCGGAAGCT CAAAGGAGAG TATCCAAAAA TTCCAAGTAT AATGCAGAAA    1500

GCACAGAAAG GGAGTCACAA GACACTGTTG CAGAGAATGA TGATGGCGGG TTCAGTGAGG    1560

AATGGGAAGC CCAGAGGGAC AGTCATCTAG GGCCTCATCG CTCTACACCT GAGTCACGAG    1620

CTGCTGTCCA GGAACTTTCC AGCAGTATCC TCGCTGGTGA AGACCCAGAG GAAAGGGGAG    1680

TAAAACTTGG ATTGGGAGAT TTCATTTTCT ACAGTGTTCT GGTTGGTAAA GCCTCAGCAA    1740

CAGCCAGTGG AGACTGGAAC ACAACCATAG CCTGTTTCGT AGCCATATTA ATTGGTTTGT    1800

GCCTTACATT ATTACTCCTT GCCATTTTCA AGAAAGCATT GCCAGCTCTT CCAATCTCCA    1860

TCACCTTTGG GCTTGTTTTC TACTTTGCCA CAGATTATCT TGTACAGCCT TTTATGGACC    1920

AATTAGCATT CCATCAATTT TATATCTAGC ATATTTGCGG TTAGAATCCC ATGGATGTTT    1980

CTTCTTTGAC TATAACCAAA TCTGGGGAGG ACAAAGGTGA TTTTCCTGTG TCCACATCTA    2040

ACAAAGTCAA GATTCCCGGC TGGACTTTTG CAGCTTCCTT CCAAGTCTTC CTGACCACCT    2100

TGCACTATTG GACTTTGGAA GGAGGTGCCT ATAGAAAACG ATTTTGAACA TACTTCATCG    2160

CAGTGGACTG TGTCCTCGGT GCAGAAACTA CCAGATTTGA GGGACGAGGT CAAGGAGATA    2220

TGATAGGCCC GGAAGTTGCT GTGCCCCATC AGCAGCTTGA CGCGTGGTCA CAGGACGATT    2280

TCACTGACAC TGCGAACTCT CAGGACTACC GGTTACCAAG AGGTTAGGTG AAGTGGTTTA    2340

AACCAAACGG AACTCTTCAT CTTAAACTAC ACGTTGAAAA TCAACCCAAT AATTCTGTAT    2400

TAACTGAATT CTGAACTTTT CAGGAGGTAC TGTGAGGAAG AGCAGGCACC AGCAGCAGAA    2460

TGGGGAATGG AGAGGTGGGC AGGGGTTCCA GCTTCCCTTT GATTTTTTGC TGCAGACTCA    2520

TCCTTTTTAA ATGAGACTTG TTTTCCCCTC TCTTTGAGTC AAGTCAAATA TGTAGATGCC    2580

TTTGGCAATT CTTCTTCTCA AGCACTGACA CTCATTACCG TCTGTGATTG CCATTTCTTC    2640

CCAAGGCCAG TCTGAACCTG AGGTTGCTTT ATCCTAAAAG TTTTAACCTC AGGTTCCAAA    2700

TTCAGTAAAT TTTGGAAACA GTACAGCTAT TTCTCATCAA TTCTCTATCA TGTTGAAGTC    2760

AAATTTGGAT TTTCCACCAA ATTCTGAATT TGTAGACATA CTTGTACGCT CACTTGCCCC    2820

AGATGCCTCC TCTGTCCTCA TTCTTCTCTC CCACACAAGC AGTCTTTTTC TACAGCCAGT    2880

AAGGCAGCTC TGTCGTGGTA GCAGATGGTC CCACTTATTC TAGGGTCTTA CTCTTTGTAT    2940

GATGAAAAGA ATGTGTTATG AATCGGTGCT GTCAGCCCTG CTGTCAGACC TTCTTCCACA    3000

GCAAATGAGA TGTATGCCCA AAGCGGTAGA ATTAAAGAAG AGTAAAATGG CTGTTGAAGC    3060

AAAAAAAAAA AAAAAAAAA AAAAAA                                         3087
```

(2) INFORMATION FOR SEQ ID NO: 6:

(i) SEQUENCE CHARACTERISTICS:
        (A) LENGTH: 945 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
GTTNTCCNAA CCAACTTAGG AGNTTGGACC TGGGRAAGAC CNACNTGATC TCCGGGAGGN     60

AAAGACTNCA GTTGAGCCGT GATTGCACCC ACTTTACTCC AAGCCTGGGC AACCAAAATG    120

AGACACTGGC TCCAAACACA AAAACAAAAA CAAAAAAAGA GTAAATTAAT TTANAGGGAA    180
```

```
GNATTAAATA AATAATAGCA CAGTTGATAT AGGTTATGGT AAAATTATAA AGGTGGGANA      240

TTAATATCTA ATGTTTGGGA GCCATCACAT TATTCTAAAT AATGTTTTGG TGGAAATTAT      300

TGTACATCTT TTAAAATCTG TGTAATTTTT TTTCAGGGAA GTGTTTAAAA CCTATAACGT      360

TGCTGTGGAC TACATTACTG TTNCACTCCT GATCTGGAAT TTTGGTGTGG TGGGAATGAT      420

TTCCATTCAC TGGAAAGGTC CACTTCGACT CCAGCAGGCA TATCTCATTA TGATTAGTGC      480

CCTCATGNCC CTGKTGTTTA TCAAGTACCT CCCTGAATGG ACTGNGTGGC TCATCTTGGC      540

TGTGATTTCA GTATATGGTA AAACCCAAGA CTGATAATTT GTTTGTCACA GGAATGCCCC      600

ACTGGAGTGT TTTCTTTCCT CATCTCTTTA TCTTGATTTA GAGAAAATGG TAACGTGTAC      660

ATCCCATAAC TCTTCAGTAA ATCATTAATT AGCTATAGTA ACTTTTTCAT TTGAAGATTT      720

CGGCTGGGCA TGGTAGCTCA TGCCTGTAAT CTTAGCACTT TGGGAGGCTG AGGCGGGCAG      780

ATCACCTAAG CCCAGAGTTC AAGACCAGCC TGGGCAACAT GGCAAAACCT CGTATCTACA      840

GAAAATACAA AAATTAGCCG GGCATGGTGG TGCACACCTG TAGTTCCAGC TACTTAGGAG      900

GCTGAGGTGG GAGGATCGAT TGATCCCAGG AGGTCAAGNC TGCAG                     945

(2) INFORMATION FOR SEQ ID NO: 7:

(i) SEQUENCE CHARACTERISTICS:
          (A) LENGTH: 450 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 7:

GTTGCAAAGT CATGGATTCC TTTAGGTAGC TACATTATCA ACCTTTTTGA GAATAAAATG       60

AATTGAGAGT GTTACAGTCT AATTCTATAT CACATGTAAC TTTTATTTGG ATATATCAGT      120

AATAGTGCTT TTTTTTTTTT TTTTTTTTTT TTTTTTTTTT TTTGGGGANA GAGTCTCGCT      180

CTGTCGCCAG GTTGGAGTGC AATGGTGCGA TCTTGGCTCA CTGAAAGCTC CACCNCCCGG      240

GTTCAAGTGA TTCTCCTGCC TCAGCCNCCC AAGTAGNTGG GACTACAGGG GTGCGCCACC      300

ACGCCTGGGA TAATTTTGGG NTTTTTAGTA GAGATGGCGT TTCACCANCT TGGNGCAGGC      360

TGGTCTTGGA ACTCCTGANA TCATGATCTG CCTGCCTTAG CCTCCCCAAA GTGCTGGGAT      420

TNCAGGGGTG AGCCACTGTT CCTGGGCCTC                                      450

(2) INFORMATION FOR SEQ ID NO: 8:

(i) SEQUENCE CHARACTERISTICS:
          (A) LENGTH: 516 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 8:

GCTCATCATG CTTCACGGGG GAGGCTGTGC GGGAAGAATG CTCCCACACA GNATAAAGAA       60

TGCTCCCGCA CAGGATAGAG AATGCCCCCG CACAGCATAG AGAAGCCCCC GCACAGCATA      120

GAGAATGCCC CCNCACAGCA TAGAGAAGCC CCCGCACAGC ATAGAGAATG CTCTTCACCT      180

CTGGGTTTTT AACCAGCCAA ACTAAAAATCA CAGAGGSCMA CACATCATTT AAGATAGAAA     240

TTTCTGTATC TTTTAATTTY TTTCMAAGTA GTTTTACTTA TTTTCAGATT CTATTTCTTT      300
```

```
ACTAGAATTA AGGGATAAAA TAACAATGTG TGCATAATGA ACCCTATGAA ACMAACMMAA    360

GCTAGGTTTT TTTCATAGST CTTCTTCCAG ATTGAATGAA CGTCTGTTCT AAAATTTAAC    420

CCCCCAGGGA AATATTCAGT TAACTATGTT AAAAACCCAG ACTTGTGATT GAGTTTTGCC    480

TGAAAATGCT TTCATAATTA TGTGTGAATG TGTGTC                              516
```

(2) INFORMATION FOR SEQ ID NO: 9:

(i) SEQUENCE CHARACTERISTICS:
        (A) LENGTH: 1726 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

```
GGATCCCTCC CCTTTTTAGA CCATACAAGG TAACTTCCGG ACGTTGCCAT GGCATCTGTA     60

AACTGTCATG GTGTTGGCGG GGAGTGTCTT TTAGCATGCT AATGTATTAT AATTAGCGTA    120

TAGTGAGCAG TGAGGATAAC CAGAGGTCAC TCTCCTCACC ATCTTGGTTT TGGTGGGTTT    180

TGGCCAGCTT CTTTATTGCA ACCAGTTTTA TCAGCAAGAT CTTTATGAGC TGTATCTTGT    240

GCTGACTTCC TATCTCATCC CGNAACTAAG AGTACCTAAC CTCCTGCAAA TTGMAGNCCA    300

GNAGGTCTTG GNCTTATTTN ACCCAGCCCC TATTCAARAT AGAGTNGYTC TTGGNCCAAA    360

CGCCYCTGAC ACAAGGATTT TAAAGTCTTA TTAATTAAGG TAAGATAGKT CCTTGSATAT    420

GTGGTCTGAA ATCACAGAAA GCTGAATTTG GAAAAAGGTG CTTGGASCTG CAGCCAGTAA    480

ACAAGTTTTC ATGCAGGTGT CAGTATTTAA GGTACATCTC AAAGGATAAG TACAATTGTG    540

TATGTTGGGA TGAACAGAGA GAATGGAGCA ANCCAAGACC CAGGTAAAAG AGAGGACCTG    600

AATGCCTTCA GTGAACAATG ATAGATAATC TAGACTTTTA AACTGCATAC TTCCTGTACA    660

TTGTTTTTTC TTGCTTCAGG TTTTTAGAAC TCATAGTGAC GGGTCTGTTG TTAATCCCAG    720

GTCTAACCGT TACCTTGATT CTGCTGAGAA TCTGATTTAC TGAAAATGTT TTTCTTGTGC    780

TTATAGAATG ACAATAGAGA ACGGCAGGAG CACAACGACA GACGGAGCCT TGGCCACCCT    840

GANCCATTAT CTAATGGACG ACCCAGGGTA ACTCCCGGCA GGTGGTGGAN CAAGATGAGG    900

AAGAAGATGA GGANCTGACA TTGAAATATG NCGSCAAGCA TGTGATCATG CTCTTTGKCC    960

CTGTGACTCT CTGCATGGTG GTGGTCGTGG NTACCATTAA GTCAGTCAGC TTTTATACCC   1020

GGAAGGATGG GCAGCTGTAC GTATGAGTTT KGTTTTATTA TTCTCAAASC CAGTGTGGCT   1080

TTTCTTTACA GCATGTCATC ATCACCTTGA AGGCCTCTNC ATTGAAGGGG CATGACTTAG   1140

CTGGAGAGCC CATCCTCTGT GATGGTCAGG AGCAGTTGAG AGANCGAGGG GTTATTACTT   1200

CATGTTTTAA GTGGAGAAAA GGAACACTGC AGAAGTATGT TTCCTGTATG GTATTACTGG   1260

ATAGGGCTGA AGTTATGCTG AATTGAACAC ATAAATTCTT TTCCACCTCA GGGNCATTGG   1320

GCGCCCATTG NTCTTCTGCC TAGAATATTC TTTCCTTTNC TNACTTKGGN GGATTAAATT   1380

CCTGTCATCC CCCTCCTCTT GGTGTTATAT ATAAAGTNTT GGTGCCGCAA AAGAAGTAGC   1440

ACTCGAATAT AAAATTTTCC TTTTAATTCT CAGCAAGGNA AGTTACTTCT ATATAGAAGG   1500

GTGCACCCNT ACAGATGGAA CAATGGCAAG CGCACATTTG GGACAAGGGA GGGGAAAGGG   1560

TTCTTATCCC TGACACACGT GGTCCCNGCT GNTGTGTNCT NCCCCACTG ANTAGGGTTA   1620

GACTGGACAG GCTTAAACTA ATTCCAATTG GNTAATTTAA AGAGAATNAT GGGGTGAATG   1680

CTTTGGGAGG AGTCAAGGAA GAGNAGGTAG NAGGTAACTT GAATGA                 1726
```

(2) INFORMATION FOR SEQ ID NO: 10:

(i) SEQUENCE CHARACTERISTICS:
        (A) LENGTH: 1883 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

```
CNCGTATAAA AGACCAACAT TGCCANCNAC AACCACAGGC AAGATCTTCT CCTACCTTCC      60
CCCNNGGTGT AATACCAAGT ATTCNCCAAT TTGTGATAAA CTTTCATTGG AAAGTGACCA     120
CCCTCCTTGG TTAATACATT GTCTGTGCCT GCTTTCACAC TACAGTAGCA CAGTTGAGTG     180
TTTGCCCTGG AGACCATATG ACCCATAGAG CTTAAAATAT TCAGTCTGGC TTTTTACAGA     240
GATGTTTCTG ACTTTGTTAA TAGAAAATCA ACCCAACTGG TTTAAATAAT GCACATACTT     300
TCTCTCTCAT AGAGTAGTGC AGAGGTAGNC AGTCCAGATT AGTASGGTGG CTTCACGTTC     360
ATCCAAGGAC TCAATCTCCT TCTTTCTTCT TTAGCTTCTA ACCTCTAGCT TACTTCAGGG     420
TCCAGGCTGG AGCCCTASCC TTCATTTCTG ACAGTAGGAA GGAGTAGGGG AGAAAAGAAC     480
ATAGGACATG TCAGCAGAAT TCTCTCCTTA GAAGTTCCAT ACACAACACA TCTCCCTAGA     540
AGTCATTGCC CTTACTTGTT CTCATAGCCA TCCTAAATAT AAGGGAGTCA GAAGTAAAGT     600
CTKKNTGGCT GGGAATATTG GCACCTGGAA TAAAAATGTT TTTCTGTGAA TGAGAAACAA     660
GGGGAAGATG GATATGTGAC ATTATCTTAA GACAACTCCA GTTGCAATTA CTCTGCAGAT     720
GAGAGGCACT AATTATAAGC CATATTACCT TTCTTCTGAC AACCACTTGT CAGCCCNCGT     780
GGTTTCTGTG GCAGAATCTG GTTCYATAMC AAGTTCCTAA TAANCTGTAS CCNAAAAAAT     840
TTGATGAGGT ATTATAATTA TTTCAATATA AAGCACCCAC TAGATGGAGC CAGTGTCTGC     900
TTCACATGTT AAGTCCTTCT TTCCATATGT TAGACATTTT CTTTGAAGCA ATTTTAGAGT     960
GTAGCTGTTT TTCTCAGGTT AAAAATTCTT AGCTAGGATT GGTGAGTTGG GGAAAAGTGA    1020
CTTATAAGAT NCGAATTGAA TTAAGAAAAA GAAAATTCTG TGTTGGAGGT GGTAATGTGG    1080
KTGGTGATCT YCATTAACAC TGANCTAGGG CTTTKGKGTT TGKTTTATTG TAGAATCTAT    1140
ACCCCATTCA NAGAAGATAC CGAGACTGTG GGCCAGAGAG CCCTGCACTC AATTCTGAAT    1200
GCTGCCATCA TGATCAGNGT CATTGTWGTC ATGACTANNC TCCTGGTGGT TCWGTATAAA    1260
TACAGGTGCT ATAAGGTGAG CATGAGACAC AGATCTTTGN TTTCCACCCT GTTCTTCTTA    1320
TGGTTGGGTA TTCTTGTCAC AGTAACTTAA CTGATCTAGG AAAGAAAAAA TGTTTTGTCT    1380
TCTAGAGATA AGTTAATTTT TAGTTTTCTT CCTCCTCACT GTGGAACATT CAAAAAATAC    1440
AAAAAGGAAG CCAGGTGCAT GTGTAATGCC AGGCTCAGAG GCTGAGGCAG GAGGATCGCT    1500
TGGGCCCAGG AGTTCACAAG CAGCTTGGGC AACGTAGCAA GACCCTGCCT CTATTAAAGA    1560
AAACAAAAAA CAAATATTGG AAGTATTTTA TATGCATGGA ATCTATATGT CATGAAAAAA    1620
TTAGTGTAAA ATATATATAT TATGATTAGN TATCAAGATT TAGTGATAAT TTATGTTATT    1680
TTGGGATTTC AATGCCTTTT TAGGCCATTG TCTCAAMAAA TAAAAGCAGA AACAAAAAA     1740
AGTTGTAACT GAAAAATAAA CATTTCCATA TAATAGCACA ATCTAAGTGG GTTTTTGNTT    1800
GTTTGTTTGN TTGTTGAAGC AGGGCCTTGC CCTNYCACCC AGGNTGGAGT GAAGTGCAGT    1860
GGCACGATTT TGGCTCACTG CAG                                            1883
```

(2) INFORMATION FOR SEQ ID NO: 11:

```
    (i) SEQUENCE CHARACTERISTICS:
        (A) LENGTH: 823 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

CAGGAGTGGA CTAGGTAAAT GNAAGNTGTT TTAAAGAGAG ATGNGGNCNG GGACATAGTG      60

GTACACANCT GTAATGCTCA NCACTKATGG GGAGTACTGA AGGNGGNSGG ATCACTTGNG     120

GGTCNGGAAT NTGAGANCAG CCTGGGCAAN ATGGCGAAAC CCTGTCTCTA CTAAAAATAG    180

CCANAAWNWA GCCTAGCGTG GTGGCGCRCA CGCGTGGTTC CACCTACTCA GGAGGCNTAA    240

GCACGAGNAN TNCTTGAACC CAGGAGGCAG AGGNTGTGGT GARCTGAGAT CGTGCCACTG    300

CACTCCAGTC TGGGCGACMA AGTGAGACCC TGTCTCCNNN AAGAAAAAAA AAATCTGTAC    360

TTTTTAAGGG TTGTGGGACC TGTTAATTAT ATTGAAATGC TTCTYTTCTA GGTCATCCAT    420

GCCTGGCTTA TTATATCATC TCTATTGTTG CTGCTCTTTT TTACATTCAT TTACTTGGGG    480

TAAGTTGTGA AATTTGGGGT CTGTCTTTCA GAATTAACTA CCTNNGTGCT GTGTAGCTAT    540

CATTTAAAGC CATGTACTTT GNTGATGAAT TACTCTGAAG TTTTAATTGT NTCCACATAT    600

AGGTCATACT TGGTATATAA AAGACTAGNC AGTATTACTA ATTGAGACAT TCTTCTGTNG    660

CTCCTNGCTT ATAATAAGTA GAACTGAAAG NAACTTAAGA CTACAGTTAA TTCTAAGCCT    720

TTGGGGAAGG ATTATATAGC CTTCTAGTAG GAAGTCTTGT GCNATCAGAA TGTTTNTAAA    780

GAAAGGGTNT CAAGGAATNG TATAAANACC AAAAATAATT GAT                       823

(2) INFORMATION FOR SEQ ID NO: 12:

(i) SEQUENCE CHARACTERISTICS:
        (A) LENGTH: 736 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

GTCTTTCCCA TCTTCTCCAC AGAGTTTGTG CCTTACATTA TTACTCCTTG CCATTTTCAA     60

GAAAGCATTG TCAGCTCTTC CAATCTCCAT CACCTTTGGG CTTGTTTTCT ACTTTGCCAC    120

AGATTATCTT GTACAGCCTT TTATGGACCA ATTAGCATTC CATCAATTTT ATATCTAGCA    180

TATTTGCGGT TAGAATCCCA TGGATGTTTC TTCTTTGACT ATAACAAAAT CTGGGGAGGA    240

CAAAGGTGAT TTCCTGTGTC CACATCTAAC AAATCAAGAT CCCCGGCTGG ACTTTTGGAG    300

GTTCCTTCCA AGTCTTCCTG ACCACCTTGC ACTATTGGAC TTTGGAAGGA GGTGCCTATA    360

GAAAACGATT TGAACATAC TTCATCGCAG TGGACTGTGT CCTCGGTGCA GAAACTACCA    420

GATTTGAGGG ACGAGGTCAA GGAGATATGA TAGGCCCGGA AGTTGCTGTG CCCCATCAGC    480

AGCTTGACGC GTGGTCACAG GACGATTTTC ACTGACACTG CGAACTCTCA GGACTACCGT    540

TACCAAGAGG TTAGGTGAAG TGGTTTAAAC CAAACGGAAC TCTTCATCTT AAACTACACG    600

TTGAAAATCA ACCCAATAAT TCTGTATTAA CTGAATTCTG AACTTTTCAG GAGGTACTGT    660

GAGGAAGAGC AGGCACCACC AGCAGAATGG GGAATGGAGA GGTGGGCAGG GGTTCCAGCT    720

TCCCTTTGAT TTTTTG                                                    736
```

(2) INFORMATION FOR SEQ ID NO: 13:

(i) SEQUENCE CHARACTERISTICS:
        (A) LENGTH: 893 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

```
GGATCCGCCC GCCTTGGCCT CCCAAAGTGC TGGGATTACA GGCATGAGCC ACCGCTCCTG    60

GCTGAGTCTG CGATTTCTTG CCAGCTCTAC CCAGTTGTGT CATCTTAAGC AAGTCACTGA   120

ACTTCTCTGG ATTCCCTTCT CCTNNWGTAA AATAAGNATG TTATCTGNCC NNCCTGCCTT   180

GGGCATTGTG ATAAGGATAA GATGACATTA TAGAATNTNG CAAAATTAAA AGCGCTAGAC   240

AAATGATTTT ATGAAAATAT AAAGATTAGN TTGAGTTTGG GCCAGCATAG AAAAAGGAAT   300

GTTGAGAACA TTCCNTTAAG GATTACTCAA GCYCCCCTTT TGSTGKNWAA TCAGANNGTC   360

ATNNAMNTAT CNTNTGTGGG YTGAAAATGT TTGGTTGTCT CAGGCGGTTC CTACTTATTG   420

CTAAAGAGTC CTACCTTGAG CTTATAGTAA ATTTGTCAGT TAGTTGAAAG TCGTGACAAA   480

TTAATACATT CCTGGTTTAC AAATTGGTCT TATAAGTATT TGATTGGTNT AAATGNATTT   540

ACTAGGATTT AACTAACAAT GGATGACCTG GTGAAATCCT ATTTCAGACC TAATCTGGGA   600

GCCTGCAAGT GACAACAGCC TTTGCGGTCC TTAGACAGCT TGGCCTGGAG GAGAACACAT   660

GAAAGAAAGG TTTGTTTCTG CTTAATGTAA TCTATGGAAG TGTTTTTTAT AACAGTATAA   720

TTGTAGTGCA CAAAGTTCTG TTTTTCTTTC CCTTTTCAGA ACCTCAAGAG GCTTTGTTTT   780

CTGTGAAACA GTATTTCTAT ACAGTNTGCT CCAANTGNAC AGAGTTACCT GCACNNCGTT   840

GTCCNTACTT CCAGAATGCA CAGATGTCTG AGGACAACCA CCTGAGCAAT ACT          893
```

(2) INFORMATION FOR SEQ ID NO: 14:

(i) SEQUENCE CHARACTERISTICS:
        (A) LENGTH: 475 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

```
TCAGAAAATA CTTTNGGGCA CATGAGAATC ACATGAGAAC AAGCTGATGC ATAATTCCTC    60

CTGTGATGGA ATGTAATAGT AATTTAACAG TGTCCTTTCT TTTTAACTGC CTCAAGGATA   120

CAGCAAAATA AAACAAAAGC AATATGAAGG CTGAGAATAG GTATCAGATT ATCATAAAAA   180

GTATAGATCA AAAGGAATCT GGTKCTNAGG TTGGCGCAGC AGCCTCTAGA AGCGACNAGG   240

GAGACTTTTA GAACTACCAT TCTCCTCTAT AAGTGGATCC NANGCCCAGG RAAACTTGAT   300

ATTGAGNACA ATGGCCTTAC TGAAATAACC TGTGATCCAC TCGGNCTCAT CATCTCCACC   360

ACCACCATAA ATTTGATGAG TNCCTATAAT ATTCCANCCA GNGGAAATAC CTGGRAGGTT   420

ACTGAAAGGC NACNATCAGA CNAAAATAAA GNATACCGTA GGTAAATTCT ACAGT        475
```

(2) INFORMATION FOR SEQ ID NO: 15:

(i) SEQUENCE CHARACTERISTICS:
        (A) LENGTH: 180 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

| GTTCTCNAGA | TCTCTTCAAA | ATTCATTNTG | CGCTATAGGA | GCTGGGATTA | CCGCGGGTGC | 60 |
| TGGAACCAGA | CTTGCNCTCC | AATGGATCCT | CCANACNGGA | NGGGGGGTGG | ACTCACACCA | 120 |
| TTTACAGGGG | GCTCGTAAAG | AATCCTGTTT | TGANTATTNT | NCCGTCAATT | ACCNCCCCAA | 180 |

(2) INFORMATION FOR SEQ ID NO: 16:

(i) SEQUENCE CHARACTERISTICS:
            (A) LENGTH: 457 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 16:

| AATGTAACMA | CMAAACCYCA | AACTCCTGNA | AGAANATGGT | TACTTATNGA | TNCCATTTNC | 60 |
| TTTTTNCACT | CTCAGACATA | AATATAAACM | MANTTTCTAC | TGTGGRAAAA | CATCTNCAGG | 120 |
| GGNCNTTTAN | CCATGATCTC | TAGNACNANG | GGCTNGTGGN | TNGTTTTAAT | GTCTCTAAGC | 180 |
| NACTNGACTA | GTTTCTCTTN | CACTGAGNAA | ACTGCNACAA | GTNNTTNCTN | CTGNATCTGN | 240 |
| ACTGNAATGC | TAAGTTNCAA | GTNCCAATGA | GCTNGTGANT | TANYCTTTAT | TTNAMCNAAA | 300 |
| GTNNTTAATC | ANCCNCAGTG | TTACTTTGNA | AAGCTNCTCC | CTGGACAGGC | GGCCCNACTT | 360 |
| CTAATGTTAT | GAATGGGCTG | GAGNANCCTC | NACNTGAGTT | TNNWAAGGNT | CAACANCCAA | 420 |
| TRGNAANTGT | AMCCGACTCT | AAATTCCAAC | CNATAAT | | | 457 |

(2) INFORMATION FOR SEQ ID NO: 17:

(i) SEQUENCE CHARACTERISTICS:
            (A) LENGTH: 373 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 17:

| ATCTGTGCTA | GGTAGTGTAC | TAATCATTCA | GTTTATCTCA | TTTAATCTNN | ATGNAACTCT | 60 |
| AAGTCATTCG | CTNTGANCNA | CACATAACAG | ATCTCGCAAC | TGNAGTTTAG | CGAGGCCAGT | 120 |
| TAATTTKCCA | AAGNTCATAA | TNCTAAGNAG | TTCTAGNATG | GAGATTCMAA | GTCCNACTGT | 180 |
| TTAGTCAAGA | GACCCTACTG | TTAACTAGTA | CCTTTACACT | ACTAACTGGG | TAANCCATAA | 240 |
| NCAATTAATG | ATAAAGATTG | AGATTACTKC | CACATTCTCA | CTGGTTATAA | ATTAAAACNT | 300 |
| CAAATAAAAA | NTCTTGGCAC | TTCTATGGTA | ATATTTTTAT | TAGGATAAAC | TTTCAAGNAG | 360 |
| TGGATNCTAG | GTG | | | | | 373 |

(2) INFORMATION FOR SEQ ID NO: 18:

(i) SEQUENCE CHARACTERISTICS:
            (A) LENGTH: 422 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 18:

```
CCCACACTGN TGGGCCATGG AAGCCATGAG TGTACCACAT GGCCCTGTCC CACTGGCCAC      60

AGTNGATTGG TTGGNTCGGG AGTAGTCACC TGATTCAAGN TGGGCCAATC AGATCCTACC     120

TCCANGGGGT TNGGAATTAG AAAACAGTGA CCCTAGYTAG TNTAGGCNAC TTGAACTGGA     180

GGGCCCATAC ATTCAGGAGC CTTATGGGGC CATGTACACA TGGAAGCAGG AAGANTGAAG     240

GAGGGAGAAG TAGAGGCCAG AAACCCACCT GGGTTCCTGT TTCCCAATGN TAAGTCCCTG     300

CCATGTYCCT GCTCTTCCTG TGGTTNGGAT CTTCAAAGGT TGCTCAAATT NGGGCAGTG     360

GCCCTGGCAG CTTTTCAAAT CCTYCCCATT TTTATTGAAG CTGAAAGACC CTTGACTAGA    420

AC                                                                     422

(2) INFORMATION FOR SEQ ID NO: 19:

(i) SEQUENCE CHARACTERISTICS:
        (A) LENGTH: 395 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

ATTGTTATTT TTCGTCACTA CCTCCCCGGG TCGGGAGTGG GTAATTTGCG CGCCTGCTGC      60

CTTCCTTGGA TGTGGTAGCC GTTTCTCAGG CTCCCTCTCC GGAATCGAAC CCTGATTCCC     120

CGTCACCCGT GGTCACCATG GTTAGGCACG GCGACTACCA TCGAAAGTTA ATAGGGCAGA     180

TCTCGAGAAT TCTCGAGATC TCCNTCMAAT TATTACTTCA NTTKCGGTAG TGATCAGNAC     240

NAGGCAGTTC TATTGATTTC TCTCCTTTCA TTCTGAGTTT CTCCATAAAT TAATTGGACC     300

TAATCATGTT TKNAATCCTG TCTTTTAGGG GGNANTTGNA CTNTCAAGTG TTTAAAGGGA     360

GGGNCGGAGN ATGATTNTGG ATTGGAGTGA GAGCA                                395

(2) INFORMATION FOR SEQ ID NO: 20:

(i) SEQUENCE CHARACTERISTICS:
        (A) LENGTH: 487 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

CAGANTTTCT GGGTNAAAAG GACCTNANAC ATAATATAGT GGACTTNCAA TAAACACTTA      60

CCAAATGGAN AAATGAACCC CTGGTCACCC CGATCTCACT AGTNCCTNCC CTGAAACCCG     120

ANANATCTGA GTCCTTTTCT CCTTTACTAA CCCTTNCTCC AATCCTGCTC ATGGGAATTA     180

ANGNTGTAAA ATANGCCTGG GGNACCTCGG RCCTCTNCCC TGGGNTCTGT GGGTGGGAGN     240

ACTGTGGAAG CCGTWTCAAT CGCCCCCACC TATGAGAGCC TTTCTNCAGG GCCAGCCATG     300

AACGTCCCCC ATGTNATCAG NATCTNCAGG CTACTGCTGT CCTTCYTGGA TWTTTAACCT     360

GGRGGCGGGC CAGGGACAGA AAARGGAGGT GGCAAGATCC TTGAACAAAA GGAGCTATAA     420

AAGGGCGTTG GGGGAAGCAA GGCAAACGGC AGATTAAACA AGCAGGCACC TCAAGGAAAC     480

GTGACGC                                                                487

(2) INFORMATION FOR SEQ ID NO: 21:

(i) SEQUENCE CHARACTERISTICS:
```

(A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

CTCGAGATCT GGCCCATCAT TTAGTTTTAT NGCTTGNAGT NTNTAGNAGA TAAAACATCC    60

ACGTGGATCT NCTCTTAGAG AAATCAANTA CTTTAGGNAT NTGATAGTCA GAGANTGGNT   120

ATCAAATNGA AAGGNATNTN GGTNGANCAG TTAGTTNGYN CCNTTNGNNG AGACCACTGG   180

GNTGTNGASA CCAGATTCMK GGGTNCNAAT CTTANGGTAA TCTNAGAGCC AACACATGGG   240

TCATNTTATS CCCCAAACTT AGCCACATCT BGTGGGGYTA TGGNGTCACC CCAAGAGCAG   300

GAGGAGCATG GNTGGATGGA AATCCATCTC CACCACTGGA ACCCCAAWTT CTGAATGNAT   360

CACCTGTTAG AGTTTCTTGT YCATAAAATA GCAGGGAATT TAGGAATTTA GTTTTTTTTT   420

AATAGTTTGG GCCTTTTATC CACACTCTCA GGAGCTTAGG ATACTTTTCT CCTTCAGCTC   480

ACTCTGAAAC TCCCTCTGGA                                              500

(2) INFORMATION FOR SEQ ID NO: 22:

(i) SEQUENCE CHARACTERISTICS:
        (A) LENGTH: 406 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

TCGAGATCTG TGGTAGTNAC ATGATATTCT GGCAMCTACT TTCATTATCA CCTTTATTAA    60

AATAAATTTA AGAAAAATG GCAGTATGTT TCTGTGRAGN CCACGAGTAC TCATTTTAAA   120

GGACTCMAGA GTTNCAGRNA AGTAAAAAGR AAAGAGTAAA ATCATTTTCT AANTYTYWYY   180

TTCCAGAAAT AACGATGTTG AGCATTAAGT GGACTTCATT TCATACTCTT TCMMAGNTTA   240

TGTAGGCATA WAWATGTGTG TGTATATACA TATATATGGG TACATCCTTA GAGAAGTTGG   300

CTGGCTAGAT AGACACACNT NAAAAATGGR ATCATACTCT AATKCCATTT NNANTTTANA   360

AAATACATAT TCAGANCCNC TGTNCTTATA NACAGAGTAA NTGAAA                 406

(2) INFORMATION FOR SEQ ID NO: 23:

(i) SEQUENCE CHARACTERISTICS:
        (A) LENGTH: 289 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

GACCCAGTAA AACTTATCTC ATGAGCATAA GGCTGAATGG GATTGACAGC CTACAGAACC    60

CGGATTTTAT CATGAGGGCA TTAGTGGGGG TTGGGGGTTA GGTACTGAAA GTTTAAGGAG   120

GTGAAAGGAA AGCAACTTGT GCCTTACAGG GTCAAGCTAG GTCAAGGAAA TTCCCAGGAG   180

CGTGTGGAAG CTCTCTACCT GATAGGTGAG CTCAAGCTTA TGACCGCCCA AGCTTCTCCC   240

CAAGCTTCCC TTCCACTGCT TCCTCTTGAT TGACTTCCAC AGCAAGGTC              289

(2) INFORMATION FOR SEQ ID NO: 24:

(i) SEQUENCE CHARACTERISTICS:
    (A) LENGTH: 367 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 24:

| | | | | | |
|---|---|---|---|---|---|
| CCATCAGGAT | TTACTGAGTA | AAAATCTCAG | GTNTTAACCA | TGCCCCTAAA | ATGTGCTATN | 60 |
| CCAAAGAGGA | ACAGGTTACT | TGGGAGGAAA | AAAGCTGCCT | GGGNAACTCC | CCNCAAATGT | 120 |
| TTATTTTAAA | TAAAAATGGT | NGATGGAAAT | ATTTTNTAAA | AGAACTTGGG | GTNTAATATG | 180 |
| GNATACTGCC | CATCAAACAA | AAAAGGAAAT | AAAACTTCNT | TCCCATTTAT | AATAAGTTNC | 240 |
| CCACCCTTTA | CTATCAAGAT | TACAACTTAT | TGACCTTTTA | TGCTNGCTNG | GTTTTTTTGG | 300 |
| GACTGCCTAA | TCCAATGTTT | AAATTTTCTA | NGTCTGNATT | TCAATGTGGG | TAGGAGTNAT | 360 |
| TTTTCAA | | | | | | 367 |

(2) INFORMATION FOR SEQ ID NO: 25:

(i) SEQUENCE CHARACTERISTICS:
    (A) LENGTH: 425 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 25:

| | | | | | |
|---|---|---|---|---|---|
| GAGTATCTGA | CAGGTAAGAT | TGCTTTTTAA | AGTTGTTTTA | AATGCATTAC | ATGACTGAGA | 60 |
| AAAGAAAAAT | GCACATTTTA | TTGTTGCAGT | TTAAAATTTC | ATTTNGNGTG | AAACTAAACG | 120 |
| TGAAACAAAA | GGGATAAATG | TGTTTTGNTT | TTGTTTTGGT | TTTACCTGTT | TGGGGTATTT | 180 |
| TTTTCTGAGT | TTGTGTAGAA | ACCCGTGTGG | NTACACTGGG | TAATCTTGTC | AGGGNTACMA | 240 |
| AMCTTGGGTC | TTGANTTTGG | TTANTTGGNT | TTANTTGGTG | NACCCATGTA | CTTGCTCTTC | 300 |
| CNTCCCAGAA | ACATAGCTTG | GTAGGCNAGG | GTTAACCCAG | TGTCGGCGAN | CCCATGTCCC | 360 |
| TANCACAGCA | TCTTGTAAGT | TTAATGCACA | ATCGTTCCNT | CCCAGGATGG | ANTTATCATT | 420 |
| ATAAA | | | | | | 425 |

(2) INFORMATION FOR SEQ ID NO: 26:

(i) SEQUENCE CHARACTERISTICS:
    (A) LENGTH: 2377 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 26:

| | | | | | |
|---|---|---|---|---|---|
| GAGAGGCGCA | GGAGCCACAA | ATAAAGCAAG | AGCCAGAATC | AGAAGNGGAG | GAAGAAGAAA | 60 |
| AGCAAGAAAA | AGRAGRAANA | CGAGAAGAAC | CCATGGRAGA | GGAAGAGGAN | CCAGANCMAA | 120 |
| AGCCTTGTCT | GAAACCTACT | CTGAGGCCCA | TCAGCTCTGC | TCCATCTGTT | TCCTCTGCCA | 180 |
| GTGGNAATGC | NACACCTAAC | ACTCCTGGGG | ATGAGTCTCC | CTGTGGTATT | ATTATTCCTC | 240 |
| ATGRAAACTC | ACCAGATCAA | CAGCAACCTG | AGGAGCATAG | GCCMAAAATA | GGACTAAGTC | 300 |
| TTAAACTGGG | TGCTTCCAAT | AGTCCTGGTC | AGCCTAATTC | TGTGAAGAGA | AAGAAACTAC | 360 |

```
CTGTAGATAG TGTCTTTAAC AAATTTGAGG ATGAAGACAG TGATGACGTA CCCCGAAAAA      420

GGAAACTGGT TCCCTTGGAT TATGGTGAAG ATGATAAAAA TNCAACCAAA GGCACTGTAA      480

ACACTGAAGA AAAGCGTAAA CACATTAAGA GTCTCATTGA GAAATCCCT ACAGCCAAAC       540

CTGAGCTCTT CGCTTATCCC CTGGATTGGT CTATTGTGGA TTCTATACTG ATGGAACGTC     600

GAATTAGACC ATGGATTAAT AAGAAAATCA TAGAATATAT AGGTGAAGAA GAAGCTACAT     660

TAGTTGATTT NGTTTGTTCT AAGGTTATGG CTCATAGTNC ACCCCAGAGC ATTTTAGATG     720

ATGTTGCCAT GGTACTTGAT GAAGAAGCAG AAGTTTTTAT AGTCAAAATG TGGAGATTAT     780

TGATATATGA AACAGAAGCC AAGAAAATTG GTCTTGTGAA GTAAAACTTT TTATATTTAG     840

AGTTCCATTT CAGATTTCTT CTTTGCCACC CTTTTAAGGA CTTKGAATTT TTCTTTGTCT     900

TKGAAGACAT TGTGAGATCT GTAATTTTTT TTTTTGTAG AAAATGTGAA TTTTTTGGTC      960

CTCTAATTTG TTGTTGCCCT GTGTACTCCC TTGGTTGTAA AGTCATCTGA ATCCTTGGTT    1020

CTCTTTATAC TCACCAGGTA CAAATTACTG GTATGTTTTA TAAGCCGCAG CTACTGTACA    1080

CAGCCTATCT GATATAATCT TGTTCTGCTG ATTTGTTTCT TGTAAATATT AAAACGACTC    1140

CCCAATTATT TTGCAGAATT GCACTTAATA TTGAAATGTA CTGTATAGGA ACCAACATGA    1200

ACAATTTTAA TTGAAAACAC CAGTCATCAA CTATTACCAC CCCCACTCTC TTTTCATCAG    1260

AAATGGCAAG CCCTTGTGAA GGCATGGAGT TTAAAATTGG AATGCAAAAA TTAGCAGACA    1320

ATCCATTCCT ACTGTATTTC TGTATGAATG TGTTTGTGAA TGTATGTGTA AAAGTCTTTC    1380

TTTTCCCTAA TTTGCTTTGG TGGGGTCCTT AAAACATTTC CCAACTAAAG AATAGAATTG    1440

TAAAGGAAAA GTGGTACTGT TCCAACCTGA AATGTCTGTT ATAATTAGGT TATTAGTTTC    1500

CCAGAGCATG GTGTTCTCGT GTCGTGAGCA ATGTGGGTTG CTAACTGTAT GGGGTTTTCT    1560

TATTAATAAG ATGGCTGCTT CAGCTTCTCT TTTAAAGGAA TGTGGATCAT AGTGATTTTT    1620

CCTTTTAATT TTATTGCTCA GAAATGAGGC ATATCCCTAA AAATCTCGGA GAGCTGTATT    1680

TAATGCATTT TTGCACTAAT TGGTCCTTAG TTTAATTCTA TTGTATCTGT TTATTTAACA    1740

AAAAATTCAT CATATCAAAA AGTGTAAGTG AAAACCCCCT TTAAAACAAA ACAAAAAAAT    1800

GAAATAAAAT TAGGCAAATT GACAGACAGT GAGAGTTTTA CAAACATGAT AGGTATTCTG    1860

CTCGGCAATT TGTAAGTTTA CATGTTATTT AAGGATAAAG GTAAATCATT CAAGGCAGTT    1920

ACCAACCACT AACTATTTGT TTTCATTTTT GTCTTGTAGA AGGTTATAT CTTGTTTTAC     1980

CTTGGCTCAT TAGTGTTTAA AAATGTACTG ATGATGTGCT TAGAGAAATT CCTGGGGCTT    2040

TCTTCGTTGT AGATCAGAAT TTCACCAGGG AGTAAAATTA CCTGAAAACG TAAGAAGTTT    2100

TAAACAGCTT TCCACACAAA TTAGATGCAA CTGTTCCCAT GTCTGAGGTA CTTATTTAAA    2160

AGAAAGGTAA AGATTGGCCT GTTAGAAAAA GCATAATGTG AGCTTTGGAT TACTGGATTT    2220

TTTTTTTTTT TAAACACACC TGGAGAGGAC ATTTGAAAAC ACTGTTCTTA CCCTCGAACC    2280

CTGATGTGGT TCCATTATGT AAATATTTCA AATATTAAAA ATGTATATAT TTGAAAAAA     2340

AAAAAAAAAA AAAATTCCTG CGGCCGCAAG GGAATTC                             2377
```

(2) INFORMATION FOR SEQ ID NO: 27:

(i) SEQUENCE CHARACTERISTICS:
        (A) LENGTH: 489 base pairs
        (B) TYPE: nucleic acid
        (C) STRANDEDNESS: single
        (D) TOPOLOGY: linear (ii) MOLECULE TYPE: DNA (genomic)

-continued (xi) SEQUENCE DESCRIPTION: SEQ ID NO: 27:

```
ATTGGAGCTC CACCGCGGTG GCGGCCGCTC TAGNAACTAG TGGATCCCCC GGGCTGCAGG        60
AATTCTCGAG ATCTCCCCCA AGTAAATGAA TGAAAAAAAG AACAGCAACA ATAGAGATGA       120
TATAATAAGC CAGGCATGGA TGACCTTATA GCACCCTGTA TTTATACAGA ACCACCAGGA       180
GGATAGTCAT GACAACNATG ACACTGATCA TGATNCCAGC ATTCAGAATT GAGTNCAGGG       240
CTCTCTGGCC CACAGTCTCG GTATCTTCTG TGNATGGGGT ATAGATTARC TGTCCATCCT       300
TCCGGGNATA AAANCTGACT GACTTAATGG TANCCACGAC CACCACCCAT KCAGAGAGTC       360
ACAGGGACMA AAGAGCATGA TCAACATGCT TGGCNCCATA TTTCAATNTC ANCTCCTCAT       420
CTTCTTCCTC ATCTTNCTCC ACCACCTNCC GGGAGTTAAC CCTGGGGTCG TCCATTAGAT       480
AATGGCTCA                                                               489
```

(2) INFORMATION FOR SEQ ID NO: 28:

(i) SEQUENCE CHARACTERISTICS:
        (A) LENGTH: 2307 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

```
AGGGTGCTTC AGTGTGGCTG ACACAGCAGC ATGGTCTTGA CAAGTTTTCT TCATCCTACC        60
ACAAAATCCC AGTTGGTAAT AGAGACTTTA CTCCTACCTA TCAAAACCAC AAAATGTCCC       120
ATTAGGGGGG GACATGTTGT ACATGTTAGG ATCATTCAAA TAACCAAGAT TATAAGGTGA       180
GGAAAGATGC CCCTAACTGA TTCTTTTGTC TCTCATCTTG TTGGTTCCAG GGACCGAGTG       240
GGGTCAATCT TCTGGTSSTG CCTCTCCAGG TCTCTTCCAG GCCGGTCATA GACGTACTCC       300
CTCTGAGGCC GACCGATGGT TAGAAGAGGT GTCTAAGAGC GTCCGGGCTC AGCAGCCCCA       360
GGCCTCAGCT GCTCCTCTGC AGCCAGTTCT CCAGCCTCCT CCACCCACTG CCATCTCCCA       420
GCCAGCATCA CCTTTCCAAG GGAATGCATT CCTCACCTCT CAGCCTGTGC CAGTGGGTGT       480
GGTCCCAGCC CTGCAACCAG CCTTTGTCCC TGCCCAGTCC TATCCTGTGG CCAATGGAAT       540
GCCCTATCCA GCCCCTAATG TGCCTGTGGT GGGCATCACT CCCTCCCAGA TGGTGGCCAA       600
CGTWTTTGGC ACTGCAGGCC ACCCTCAGGC TGCCCATCCC CATCAGTCAC CCAGCCTGGT       660
CAGGCAGCAG ACATTCCCTC ACTACGAGGC AAGCAGTGCT ACCACCAGTC CCTTCTTTAA       720
GCCTCCTGCT CAGCACCTCA ACGGTTCTGC AGCTTTCAAT GGTGTAGATG ATGGCAGGTT       780
GGCCTCAGCA GACAGGCATA CAGAGGTTCC TACAGGCACC TGCCCAGTGG ATCCTTTTGA       840
AGCCCAGTGG GCTGCATTAG AAAATAAGTC CAAGCAGCGT ACTAATCCCT CCCCTACCAA       900
CCCTTTCTCC AGTGACTTAC AGAAGACGTT TGAAATTGAA CTTTAAGCAA TCATTATGGC       960
TATGTATCTT GTCCATACCA GACAGGGAGC AGGGGGTAGC GGTCAAAGGA GCMAAACAGA      1020
YTTTGTCTCC TGATTAGTAC TCTTTTCACT AATCCCAAAG GTCCCAAGGA ACAAGTCCAG      1080
GCCCAGAGTA CTGTGAGGGG TGATTTTGAA AGACATGGGA AAAAGCATTC CTAGAGAAAA      1140
GCTGCCTTGC AATTAGGCTA AAGAAGTCAA GGAAATGTTG CTTTCTGTAC TCCCTCTTCC      1200
CTTACCCCCT TACAAATCTC TGGCAACAGA GAGGCAAAGT ATCTGAACAA GAATCTATAT      1260
TCCAAGCACA TTTACTGAAA TGTAAAACAC AACAGGAAGC AAAGCAATGT CCCTTTGTTT      1320
TTCAGGCCAT TCACCTGCCT CCTGTCAGTA GTGGCCTGTA TTAGAGATCA AGAAGAGTGG      1380
```

```
TTTGTGCTCA GGCTGGGAAC AGAGAGGCAC GCTATGCTGC CAGAATTCCC AGGAGGGCAT    1440

ATCAGCAACT GCCCAGCAGA GCTATATTTT GGGGGAGAAG TTGAGCTTCC ATTTTGAGTA    1500

ACAGAATAAA TATTATATAT ATCAAAAGCC AAAATCTTTA TTTTTATGCA TTTAGAATAT    1560

TTTAAATAGT TCTCAGATAT TAAGAAGTTG TATGAGTTGT AAGTAATCTT GCCAAAGGTA    1620

AAGGGGCTAG TTGTAAGAAA TTGTACATRA GATTGATTTA TCATTGATGC CTACTGAAAT    1680

AAAAAGAGGA AAGGCTGGAA GCATGCAGAC AGGATCCCTA GCTTGTTTTC TGTCAGTCAT    1740

TCATTGTAAG TAGCACATTG CAACAACAAT CATGCTTATG ACCAATACAG TCACTAGGTT    1800

GTAGTTTTTT TTAAATAAAG GAAAAGCAGT ATTGTCCTGG TTTTAAACCT ATGATGGAAT    1860

TCTAATGTCA TTATTTTAAT GGAATCAATC GAAATATGCT CTATAGAGAA TATATCTTTT    1920

ATATATTGCT GCAGTTTCCT TATGTTAATC CTTTAACACT AAGGTAACAT GACATAATCA    1980

TACCATAGAA GGGAACACAG GTTACCATAT TGGTTTGTAA TATGGGTCTT GGTGGGTTTT    2040

GTTTTATCCT TTAAATTTTG TTCCCATGAG TTTTGTGGGG ATGGGATTC TGGTTTTATT     2100

AGCTTTGTGT GTGTCCTCTT CCCCCAAACC CCCTTTTGGT GAGAACATCC CCTTGACAGT    2160

TGCAGCCTCT TGACCTCGGA TAACAATAAG AGAGCTCATC TCATTTTTAC TTTTGAACGT    2220

TGGCGCTTAC AATCAAATGT AAGTTATATA TATTTGTACT GATGAAAATT TATAATCTGC    2280

TTTAACAAAA ATAAATGTTC ATGGTAG                                       2307

(2) INFORMATION FOR SEQ ID NO: 29:

(i) SEQUENCE CHARACTERISTICS:
        (A) LENGTH: 343 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 29:

GGCAGCTATT TACATGGCCT CACAGGCATC AGCTGAAAAG AGGACCCMAA AAGAAATTGG     60

AGATATTGCT GGTGTTGCTG ATGTTACAAT CAGRCAGTTC TATAGACTGA TCTATCCTCG    120

AGCCCCAGAT CTGTTCCTTA CAGACTTCMA ATTKGACACC CCAGTGGACA AACTACCACA    180

GCTATAAATT GAGGCAGYTA ACGTCMAATT CTTGANNACM AAACTTKNCC TGTTGTACAT    240

AGCCTATACM AAATGCTGGG TTGAGCCTTT CATAAGGNAA AACMNAAGAC ATGGNTACGC    300

ATTCCAGGGC TKGANTACTT ATTGCTTGGC ATTCTTGTAT GTA                     343

(2) INFORMATION FOR SEQ ID NO: 30:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

AAAGGGCTAA CCAGCCACTG CACCAAAATT AGTCCTTACA TTATAATACT CTGGCCATTG     60

GAAGAGAAAA ATGGGAAAAT TCAACAATTT GAAAGACTAT GATCCCTCTG GCTCATGATC    120

TACTGACCAG AATGAAGTCC TGAAGGATTT CCTTCTGTTA TGTTATCTAC CCAGCTAATC    180

TCAAACAAGA GGAGCTGGAA AGAACAAAGC CCCATGAAGC TACCCCTAGA CCCAGAAAGC    240

CAAGAACAGG GCCAAGAAAA TGAACAGCAG ACAAGCCTGA AATAGAAGTG GNACAGACAT    300
```

```
GTGGNAAGAC CAAGTACACC CAGTTNGGTG GTAAAGATTC CGATATCAAG CTTATCGATA      360

CCG                                                                   363
```

(2) INFORMATION FOR SEQ ID NO: 31:

(i) SEQUENCE CHARACTERISTICS:
        (A) LENGTH: 362 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:

```
AGTACATGGT TTCTTGNCCA CCCCASCCAC CTTTCCCCAT CTCTACCGGY TGATAGTCTC       60

TCAGNTAGTA GACCTTTTCT NGTTTAGRCA GGGCCACNTT TTTAAAAACT CCAGACGGGT      120

ACCCTCCATG TKGMAGGCGA CGTGGCCCTG GATCACTCAA CTGANTGTCA TNKGANTGGT      180

GCCCCCAGAG TGAGGACAAT GGTGNAGCCC TCCTAAGGCC CTNCCTGAGT GTCCCTCCTT      240

CATGAAGATG ATTCTGAGGN TTCCCAGGCC TNCACCCTTC TTKGAAARCC CATAGNAGTT      300

CATATGNACT NCTCTNCTAT GCTCACCAAA CTCTNCCTTC ATCATACTTG GGGATGTGT       360

GT                                                                    362
```

(2) INFORMATION FOR SEQ ID NO: 32:

(i) SEQUENCE CHARACTERISTICS:
        (A) LENGTH: 475 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

```
GTGCATGTAA TTACAGTTAC GATATATGAA ACGTACAAAA TATTATGAGT ATATAATATG       60

GGGAGACTTA ATCTAGTTTG GGGGATCAGG GCACATTTCT CTAAGAAAGT GACATTTGAA      120

TTGAGCTCTG AAGGATAAAT AGACATTACC CAGAAGAATA AAATGATGGG GAAGAAGGAG      180

GACATTTTCC GTAGATTTCC AGTGGCCCCN CTTGATCCCT TATCCACTCA TCACTNAGGA      240

GGATATTAAA TKCTATAGAA ATGGRAGRAA GACMMAAAGA GACCCTNATA TCTCGAGAGG      300

ATCCAGCMAA ATTCCAAGAG ACACAACAWT AAGAAACTNG GAAGGAAGAG AAAAGGCMMN      360

NNAGGNAAAA GAAAGACAAG GAAATTNWNN NAGNACGGAG AGAAAGAGAG AGGGAGCGTN      420

NAAGGGNACG AGAAAGGCGA GNACGGGGAC GAGAAAGGGN AAGAGNACGT AAACG           475
```

(2) INFORMATION FOR SEQ ID NO: 33:

(i) SEQUENCE CHARACTERISTICS:
        (A) LENGTH: 346 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 33:

```
GGAAATAAAT GAGATCTCAG TGGTGGTATG GATTGGACTG ATCTCTGTAA CTGTGTNTGG       60

AAAAAGGACC GGAAAATGAA AGCCAGATCC CAGTAAGGGG TAGAGAGGGG CCAAGAGAAC      120

TGAACATCTG GGCTGCCGGA GAAATCAAAG TCTAGGAAGT AAGAGGTAAG AGTGTACTAC      180
```

```
AGGGGACATA CCCCAATCTC TTGGTTCCCT CCCTCTNCCT TCCTCTCCCA GAGACCCAGG      240

TCCCTGGGAC TATNTTGGAT CTGTCTCTGA AGCTGAAAAA CAAAAGGCAG AGGAGACAGT      300

CGGNTCTAAG TGACCAATCT CAAGCCAGCT TGGTCAGAAN TCCTAA                     346
```

(2) INFORMATION FOR SEQ ID NO: 34:

(i) SEQUENCE CHARACTERISTICS:
        (A) LENGTH: 433 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 34:

```
AAATCCAGTG CAGGCAACAT TATGTGGAAA TAGAAACAGG GCTCCTGCTA GGAGATTGAN       60

ATTCTGGCTT TCCTTTGGAA CCCCTCACTG ACTCATCGCC CCTGAANCAG GANCCANCAG      120

GTNCCAAGGC TCCCCTGCTC CTNTCCCTNC CCCAGGGCGA GATAGGAARC CGGAARCCTG      180

GGCAGGCTGA RCCCANCCGA CTGGAACCAG GGNAGANCCT GTGGGTGGGT GGNAGGGAGG      240

GAAGGAGGCC AGATTCCTCC AGAACTGGGG RAGAGAACAG GTTTTGGAAG TTGGGGGAGG      300

GTTTGGGTTT CACAGTGATG GTTTCATGAN ACCCTGGAGG GTTNCACACT CCTGGTKCAN      360

TTTTGNTANT CGTNCTTTGA ANACARNCCG CTTCCTTTCA ACCCTCCNCN TAAAAAGTTT      420

TGATNTTTTA AGG                                                        433
```

(2) INFORMATION FOR SEQ ID NO: 35:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 35:

```
ACCAAGAGCC CCCAGTTTAT GNTAACTCTC ATGACAAACA CAATTTTAGT ACCTCTCACT       60

ACCAACTATC CAGGAACCAG GANTCACCTA TTACTACGGT TCCAGCAGAA TGGGAATCCC      120

ATTCTCGGAT ATCCAGGGTA AATCCCTGAC CATGTGAGAG GAATCCTAGT GCCCCAACAA      180

CCTCACCCCC TGACTCCTCC TCAANGGCTC TGCCAAGTCA ACAAAAAAAT CCTCTACATT      240

TACACTATCT GTAAAGCCAA AGACCAGCGT CAACCTAAAT GTCCATCAAT AAGGGAATGG      300

TTGGATAAGT AAAAATTATG CAGCTGTAGG AAGGAATGAA GAATGTCTAT                 350
```

(2) INFORMATION FOR SEQ ID NO: 36:

(i) SEQUENCE CHARACTERISTICS:
        (A) LENGTH: 512 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 36:

```
AAAGGGAACA AAAGCTGGTA CCGGGCCCCC CCTCGAGGTC GACGGTATCG ATAAGCTGGA       60

TATCGAATCC TCGAGATCTA CCTAAAAAAA AAAAATTAAC TTCCCAAATG TGGGAGTCTA      120

CTCTGTTCCC TCCTNGTNTT TATTNCTGTN TACTTTYCTA ANATGGTTAA AATGTGTAAN      180
```

```
CAATATGTGT CCTTTNACTN KGGKGTGAAC ATTTTTYCTA TTATAAATYC TWAGAAAATA      240

TTNCTATGGN TATGAGATAT TKGATTCCAA GTGCCTKGTA ATTTACTYCT CAAATGTCCC      300

TGATGTKGGA NATTKGTTNC TAGTGTTYCA CTATTTAAAA AAACAGNAAT ATCTGTCTNT      360

ATGCTNAGAG CTTNTYCAGT TTYCAAATTA TTNCCTTAGG GTAAAATCCT AGAAGTAGAA      420

TTTTTGGGGC AAATTATCTA CATATTTATA ATTGTCTTGG TATTCCAAAT CTCGTTTTCC      480

AAAAGCTTAT ATCAATTTGT ACTTAACACC AG                                   512

(2) INFORMATION FOR SEQ ID NO: 37:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 37:

ATTTAAGATG ACTGGGGGTC TCTNCCTAAT CCCATACTCC ACTGGAGAGG ANAAGTGGGA       60

AAGGTTGGTC TAGTTARGGT NGNTGGGGAC CCTCCCAAGA GCTGNAGAAG CAGAGATAAG      120

NAGAGCCTNC TNCTAAATCC ACATGGNCCT YCCAAGGNTC TCATCCTCTA GGACCTACCA      180

CTNCTCAGTC TACTTACTTG TCTYCTGANA TGCTTTCTNG AGGGGNAGAA AACAAAGGAA      240

GAGTAATAAC AAGCAGNAGA AACTGCAGAG AATGNAAAAT AAGTCCATAG GAGAATGTTG      300

NAAATAGAAT CATCCNCCTT TACATATTGT CACTCCAGGA AAACTGCCAA GAACCACTCA      360

TTCCTCTAGA TACAMTTCCT GTAGGATCCY CCCAGACTTC CTCCCTTAAG CACGTCAGTA      420

TTCTCCTTAT TCTCCCTTCA TTTCAACCCT                                      450

(2) INFORMATION FOR SEQ ID NO: 38:

(i) SEQUENCE CHARACTERISTICS:
        (A) LENGTH: 766 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 38:

CGAGATCTGC CCCAGCCCAC ATTTCCTTTG TTGAATGAGT AGAGAAGACT GAGAAGTATC       60

ACTCACCCGT GATGTGGTTT GTCCCTTTTC CAGCCAGTGT GTTGGTAATA AAAGTCACCT      120

TTCAGAGCTT TGGTCCCCGT AATGCCCGTC TTTCCTGTGT CCAGGAATAA CCTTTGNTAC      180

TAGGCAGTCC TCTGAAAGAT TTGTAGAAGG TTAAAGTGGA AAGGGACTTG AAGCTCATA       240

GAATCCATGC CTCTTCTTTT AGCATCAAGG AATTAGAAGT CCTGAGAGAT GAAGAATGTT      300

GTCTTCCCAA CTCAAACCCA TTTCTTGAAG CCATTTCCCT GGTTACTGNA TTGGCCACAA      360

CCCTTCCCCC TTGNTATCCT CATCCTGCTA ATGCTGTTTT TAATGGCCTG CCAGTCTGGA      420

TTTGTCTTTG GCAACCAAAC AATTTTGCTT CACAAGATTC CTACTTAAGG GAAGAGAGGG      480

GCTCCTCATT TNTCACTTGT ACAAGAGCAG GGCTGGTCAG CTTTACACAG GTGTCAGATG      540

AACCGTCACA ANCCAGANTT NCATGTTGGC CTCAGGAGGG CTTCNAGGTC CAACATCTCG      600

ACGTAAGGAG CGTTCCCAGT TCTTTCATGC TCAGATAACA GTNCTAACTN CAGCTGTTTC      660

ATCCCNAATC CCTANTTGAG GTCTTAACAT CTATTCCATT TTKCCNACMA GGGTTATNCT      720
```

```
GTTAACCCTC TNCACCAGAN TTAGANCTGA CTGATNCACT TCCTAG                   766
```

(2) INFORMATION FOR SEQ ID NO: 39:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 39:

```
TCATACTTGT ATAGTTCKNT AAGATAATCA CTCTCTCACT CAGACATNNG GNGRARNGCC     60
CNTCGATCAC TTGGGANAGG NGACTTGCMA TGTTTAATGA TTGTCANCCM NANAANTAAG    120
CTNACAGGGC AAAAACAGCC TYANGTCAGT TCTNTCTCCC TAATCCTCTA GRAKNAAATC    180
NNAWRNTRNN ACTCTGNNTC TGTGCCATNA NANATNTTNC ANTTGTATTT ATGNACTCCA    240
CATNGAGTAC ACCTCACTAA WTNTNCTNCT GGGNAACNCC CSCMCCANTT TTTNNTTGNT    300
GANANACARC AATGCTGGCA TACNGTG                                       327
```

(2) INFORMATION FOR SEQ ID NO: 40:

(i) SEQUENCE CHARACTERISTICS:
        (A) LENGTH: 431 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 40:

```
CCAGACTTTC ATAACTNGTG TTATTATGAA GATTAGAGTN CTGAAGCTTA CTGGATTAGA     60
AGAGNACGAG GGGGTAGCTG CCCCAATATA TTCTAATTTC TCTKGAGGAC CACCAAATNG    120
GMAGAGTGTC TCTGATAGGG AAAAGGAAGA GTTGGAAGGN ATCTTAGCCT CTAGGANAAA    180
AGAACCATTT TTATTGGCCA CCAAAGTTAC ATCTAGTKGC CTACAAATTT ATNTCCAAAC    240
TCCTTATCCT GCCAATTCAG GGTCCTGNAA ACTGATGCCA AACTATAGTT TAGTCTNCTA    300
TCACATGACT GCATTATACA TACCCAATTA TCTGGGMAAA CAGACCTGAT CCAAACACAG    360
TTKGGTNCTT TCCTTNCCTT NCCTTKGTTT AGCCTGTYCC GTCTACTNGG GGTGTCTTKG    420
ATTTGCTCCA G                                                        431
```

(2) INFORMATION FOR SEQ ID NO: 41:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 41:

```
TTTTTTTCCA CCAGACTTAC CAAATTTTAG ATGNATGGAA GAACTGTAAA TNCCCATAAA     60
GNTAATCTAT NCATNGACCC CCACCATTAT GATAGAGATC ATNTGGTGAN TAATGAAAGA    120
TGAAACTCTC AGCTGGGAAA GTAANAAGGA ATAGGATGTA AGTATGAGCT CCTGTTTTTT    180
ATTATNTTTA TGGATGCCCC CTCAGAAAAA TATGNAANGG GGTAACTGAC TNGGAAATGG    240
GTNTTTTATG NATAGTAAGT CCCACTCACG AGGTTT                             276
```

(2) INFORMATION FOR SEQ ID NO: 42:

(i) SEQUENCE CHARACTERISTICS:
        (A) LENGTH: 270 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 42:

```
TCGAGATCTA AAGCAGATGN AGACTTTNCA CNAAATAAAT TTACTGCTTT TTTYCTGTGA      60
NATAAGTTNC GAGAAGGAAA GCTTTKGATT NCTRNATGAG TYCAGTGGAT TATYCTNAGN     120
ACTAGAGTKG NKGTKGAAGN CATGGNACAT TTATATAGWT YWTTCAGTTC TACACTAAAT     180
GATGGAAGAA TGAGAAATCC TATATGACAA ATAGAAAAGT YCATYCTYCA TAATTGAGAA     240
CATTGAGCAG TTGGATTACC AAGATCTCGA                                      270
```

(2) INFORMATION FOR SEQ ID NO: 43:

(i) SEQUENCE CHARACTERISTICS:
        (A) LENGTH: 580 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 43:

```
CTTAGTTTTA GACTAGTTTC ATTATACTAC CAGTTTCTAA TATGTTGGTT TTTTATTCAC      60
TATTTGATAT ATTTGTTTTA ATATATGTTC TTGTTTTAGC AGGTAAAAGA ATCATAACAA     120
ATGTTTTTAA AAGAACATTA TTATTCTTTA ATAACTGTCT TTTTATGCAT TTGGCATGCC     180
AACTTTTTTC ATTAACATCT TGGGTATTTT ATAAAAAGAG GGAAAGCTCA ATGTTTAACA     240
GGTAGCTTTT CTTAGGAGCT AAATTAAATA TTTAACAAAT CTCCTTCCCT TCNCCCTTCC     300
CCATCCCTCA AAGNATGGGT GNANTTATCT TTAACTTTTG GGCTNGCATC CNTGNAAGCT     360
TATGGNTANT CATAGTCTNA CMAAACTAGG GTCACCNAAC TTGGCAGCAG AAATAATCTA     420
GTCTTACTGT GATAACTACC CAATTACTTT ATTATTTTTC CAGTTNCAGT TCCAAATGTT     480
TTGTGGNAAN AATTTTTNCT GTTTGTGATT TTCCAAGCTT AGAGGGGGAA ACCAACTTTC     540
CAGTGTTGGA GAGCACTGNA TAGTTTATGN ATTGTGTAAA                           580
```

(2) INFORMATION FOR SEQ ID NO: 44:

(i) SEQUENCE CHARACTERISTICS:
        (A) LENGTH: 347 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 44:

```
TGTTTCTTAA NACAGAAAAA AATTTACTGA TNGGACATTG TTCTAAGTGT ATTATTGTAT      60
TAAATGGATC ATTTAATTTA ATCTTCATAA CTGACATAGG AGTTGAGTAA CTTGTGTGGT     120
CAAATAGCTA GTAAGTGATG AGTAGGCTGG GCGCAGTGGC TCAAGCCTGT AATCCCAGCA     180
CTCTGGGAGG CTGAGGCAGG CAGATCACTT GAGGTCAGGA GTTTGAGACC AGCCTGGNCA     240
ACATGGNAAA ACCTCGTCTC TACTAAAAAT ACAAAAATTA GCTGGGCGTG GTGGGNGCGC     300
```

```
ACTTGTAGNC CCAGNTACTC GGAAGGCTGA GGCAGGAGGA ATCGCTT              347
```

(2) INFORMATION FOR SEQ ID NO: 45:

(i) SEQUENCE CHARACTERISTICS:
        (A) LENGTH: 430 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 45:

```
GCTCATCATG CTTCACGGGG GAGGCTGTGC GGGAAGAATG CTCCCACACA GNATAAAGAA   60

TGCTCCCGCA CAGGATAGAG AATGCCCCCG CACAGCATAG AGAAGCCCCC GCACAGCATA  120

GAGAATGCCC CCNCACAGCA TAGAGAAGCC CCCGCACAGN ATAGAGAATG CTCTTCACCT  180

CTGGGTTTTT AACCAGCCAA ACTAAAATCA CAGAGGGCAA CACATCATTT AAGATAGAAA  240

TTTCTGTATC TTTTAATTTC TTTCAAAGTA GTTTTACTTA TTTNCAGATT CTATTTCTTT  300

ACTAGAATTA AGGGATAAAA TAACAATGTG TGCATAATGA ACCCTATGAA ACAAACAAAA  360

GCTAGGTTTT NTNCATAGGT CTNCTTCCNN ATTGAATGAA CGTCTNTCCT CAAATTTANC  420

CCCCCAGGGA                                                        430
```

(2) INFORMATION FOR SEQ ID NO: 46:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 46:

```
CAAACCCTAT GNGAAATGGA AAGGAAACTA TTCTAAAGCA TAAAAGGTAG AAATATATAT   60

ACCACCCATC AAGAAAGATT ATTTTTGNTG AACTCAAGTC ACCAGAGTGG CTAAAGCCCA  120

GTAGAATGGA AATGATTATA TGGAAGGTGA GGCCAACGGG ACCAGAACAT ACTGTGATAG  180

ACAGNAAGGA GCTGTCTATC TTCTATTCTC CCACAGAAGG AGGTGACTAA GTCANCTGCC  240

CAAGCAATGT TATATCTGCA ATTGATGTNC AGCAGTACAA GTCTGAACAA CTTGGATTGG  300

NTGATTAATG TCCACANTAA ACATACAAGT CNTAATAGCT ATCTCTATAT AGTCTTTGGG  360

TNTTTACAAG GCACTGNCAC ATNATCTCAC CTATTCCTCC                       400
```

(2) INFORMATION FOR SEQ ID NO: 47:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 47:

```
AGNATCCAGA ATTGAGTGNA GNGTTCTCTG GNCCACAGTC TCGGTATCTN CTGTGAAATG   60

GGGTATAGAT TCTACAATAA AACAAACACA NNGGCCCTAG GTCAGTGTTA ATGGAGATCA  120

CCANCCACAT TACCACCTCC AACACAGAAT TTTCTTTTTC TTAATNCAAT NCGTNTCTTA  180

TAAGTCACTT TNCCCCAACT CACCAATCTA GNTAAGAATT TTTACCCTGA GAAAAACAGC  240
```

-continued

```
TACACTCTAA AATTGCTNCA AAGAAAATGT CTAACATNTG GAAAGAAGGA CTTAACATGT    300

GANGNAGACA CTGGCTCCAT CTAGNGGGTG CTTTNTTTTG AAATAATTAT AATNCCNCAT    360

CAAATTTTNG GGGGNTACAG CTTATTAGGA ACTTGTTATA GAACCAGATT CTGCCACAGA    420

ANCCACGTGG GTTGACAAGT GGTTGNCAGA AGAAAGGTAA TATGGCTTAT NATTAGGGNC    480

TCNCATCTGC AGAGTAATTG                                               500
```

(2) INFORMATION FOR SEQ ID NO: 48:

(i) SEQUENCE CHARACTERISTICS:
        (A) LENGTH: 460 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 48:

```
AAAATGCTTG ANNCAAATGT CATCTAGTTC CATCTCTACG ACTCTCATGG GGTCCAAAGA     60

AGAGTTTTAN TTGAGTTTTA GAATGTGAAG TTGTGAAGTG TCTGAAAAAC TACATGGTGN    120

TCTGAAAGNC AAACTTTTAG CCTTGGGGGA GAGCATCTAA GACAGNAGGT GAAGGGNAGG    180

GGTTAGAACT AGAGGGATTG AAGAATATTA TCCATATAGG TTAGGGTTAG GTNNGGCAAC    240

GTTTTATAGA ACAAACATTG GCAAGCTACA GCCACAGGCC AGATCTGTCT NCTACCTTCC    300

CACAAAGGTG TAATAACAAA GTTATTCACA AATGTGTGAA TAAACTNNCA TTGGAAAGTG    360

CCCACGCTCC TNGGTTTATA CATTGTCTGT GGCTGCTTTC ACACTACAGT AGCACAGGTG    420

AGTGTNTGCA CTGGAGACCA TATGCCCCAT AGAGCTTTAA                          460
```

(2) INFORMATION FOR SEQ ID NO: 49:

(i) SEQUENCE CHARACTERISTICS:
        (A) LENGTH: 370 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 49:

```
ATCAAGCAAC AGTGTGTTAT GCCTATACTC CATGTTTATA TGTGTGTATT AAAAAATGTA     60

TTTGTATATA TGTGTATGTA TAAGTGTGTG TGTGTGTATG ATGATTCTNC TCCCGNTTTG    120

AAGGTGAAAG AAAGCACACC TTTATTTAAG CATAAACTTT GGGTTTCAGA TACTGTCTGG    180

AAAAATGATT TATCTCCCAC TTTGAAATTC CAAAATACGT ACATATATTT TTTTTTTCTT    240

TTCTTTTTTA GTTTNAGGGT CTTGCTGTGT TGCCCAGGCT GGAGTGCAGT AGTGTGATCA    300

TAGNTCACAC AGNCTCTAAC TCCCAGGNTC AAGNTATCTT CCTGCCCCAG NCTCCTGAGT    360

AGNTGGGACT                                                          370
```

(2) INFORMATION FOR SEQ ID NO: 50:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 50:

```
CAAAAAATCA AAGGGAAGNT GGAACCCCTG CCCACCTCTC CATTCCCCAT TCTGCTGGTG      60

GTGNCTGCTC TTCCTCACAG TACCTCCTGA AAAGTTCAGA ATTCAGTTAA TACAGAATTA     120

TTGGGTTGAT TTTCAACGTG TAGTTTAAGA TGAAGAGTTC CGNTTGGTTT AAACCACTTC     180

ACCTAACCTC TTGGTAACGG TAGTCCTGAG AGTTCGCAGT GTCANTGAAA ATCGTCCTGT     240

GACCACGCGT CAAGCTGCTG ATGGGGACA GAAACTTCCG GGNCTATCAT ATCTCCTTGA      300

NCTCGGCCCT CAAATCTGGT AGTTTCTGCA CCGAGGGACA CAGTCCACTG CGATGAAGTA     360

TGTTCAAAAT CGNTTTCTTT AGGGAACTCC TTCCAAAGTC CAATAGTGNA AGGTGGTCAA     420

GGAAGGATTT GGAAGGAAGN TGNAAAAGTC AGNCGGGAAT CTTGATTTGG NTAGNTGTGG     480

ANANAGGAAA TCACTTGGCC                                                 500

(2) INFORMATION FOR SEQ ID NO: 51:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 51:

GGAAAGAGGT CTCCTAACAC CCAGACAGTG TAAAAATCCA GTTTTTCTTC CTTTTGGNNG      60

GAGACAGAGT CTCGCACTGT AGCTCAGGCT GGAGTGCAGT GGCAC                    105

(2) INFORMATION FOR SEQ ID NO: 52:

(i) SEQUENCE CHARACTERISTICS:
        (A) LENGTH: 386 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 52:

AGTCCCAGCT ACTCAGGAGG CTGGGGCAGG AAGATAGCTT GAGCCTGGGA GTTAGAGGCT      60

GTGTGAGCTA TGATCACACT ACTGCACTCC AGCCTGGGCA ACACAGCAAG ACCCTAAAAC     120

TAAAAAAGAA AAGAAAAAAA AAATATATGT ACGTATTTTG GAATTTCAAA GTGGGAGATA     180

AATCATTTTT CCAGACAGTA TCTGAAACCC AAAGTTTATG CTTAAATAAA GGTGTGCTTT     240

CTTTCACCTT CAAAGCGGGA GAAGAATCAT CATACACACA CACACACTTA TACATACACA     300

TATATACAAA ATACATTTTT TAATACACAC ATATAAACAT GGAGTATAGG CATAACACAC     360

TGTTGCTTGA TAAAATATAG GGATCC                                         386

(2) INFORMATION FOR SEQ ID NO: 53:

(i) SEQUENCE CHARACTERISTICS:
        (A) LENGTH: 377 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 53:

TATATTTNAT CAAGCAACAG TGTGTTATGC CTATACTCCA TGTTTATATG TGTGTATTAA      60

AAAATGTATT TGTATATATG TGTATGTATA AGTGTGTGTG TGTGTATGAT GATTCTCCTC     120
```

```
CCGNTTGAAG GTGAAAGAAA GCACACCTTT ATTTAAGCAT AAACTTTGGG TTTCAGATAC      180

TGTCTGGAAA AATGATTTAT CTCCCACTTT GAAATTCCAA AATACGTACA TATATTTTTT      240

TTTTCTTTTC TTTTTTAGTT TNAGGGTCTT GCTGTGTTGC CCAGGCTGGA GTGCAGTAGT      300

GTGATCATAG NTCACACAGG CTCTAACTCC CAGGNTCAAG CTATCTTCCT GCCCCAGNCT      360

CCTGAGTAGG TGGGACT                                                    377

(2) INFORMATION FOR SEQ ID NO: 54:

(i) SEQUENCE CHARACTERISTICS:
        (A) LENGTH: 521 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 54:

CTGCAGTAAG CCACGTTCAT GCCACTGTAC TCTAGCGTGG ATGACAGAGA GAGATCCTGT      60

CTTTGGAAGA AAAAACAAA AAGAAAAAAA AAAGAGTATG GCCATGGCCT TATAATATAG       120

AAGGGGTCAC ATATTAATCT CTGAAAATGG ATCTCTTGTG GGCTTTCATA CAAGGCAACA     180

GCCACAGAGT ACGTACCTGA AAGCTGCCTG GGNTTAATGG CTGGNAGTAT GTTCTAACTN     240

GTTCAGGNAC CCATGTCACN ACTGGTGGTT ACAGAATGTG AATCTCACAC TGTCCNAAAT     300

CGGTTTTATT TTTAAAANGA ATAATTCTAN TACATTACCT TATAAAAAGT AGGTAACCTA     360

ATTTTGGNTT TTAAAAGTGA ATTGAGGGCA GATGCAAGTG GNTCACACCT ATTAATCCCA     420

AATACCTTGG AGAGGGCAAG GTAGGAGGAT TGGTTGGAGC CCAGGAGTCC AAAGACCAGG     480

CTAGGGAATA TTGNAAGAAN GTCCTCTCTA CAANAAANAA T                         521

(2) INFORMATION FOR SEQ ID NO: 55:

(i) SEQUENCE CHARACTERISTICS:
        (A) LENGTH: 516 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 55:

CTGCANGAAG CTTTTNTTNC TTTTNGGNGG AGACAGAGTC TTGCTGTGTC ANCCCAGGCT      60

GGGGTGCAGT GGNACAGTCA TAGCTCACTG CAACCTTGAA CTCCCTGGNT CATGCGATCC     120

TCCCACTTCA GCCTCTCAAG TAGCTAGAAC TACAGGTGTG CACCACCATG CCTGACTAAC    180

TTGTTTATTN GNGGGAGAGA GAACGNTCTT GCTATATTGC CTAGGCTGGT CNTTGAACTC    240

TTGGGNTNCA AGCAATCCTC CTACCTTGGC CTCTNCAAGG TANTTGGGAT TNATAGGTGT    300

GAGCCACNTG CATCTGGCCT CAATTCACTT TTAAAATNCA AAATTAGGTT ACCTACTTTT    360

TATAAGGTAA TGTATTAGAA TTATTCTTNN NAAAAATAAA ACCGATTTGG GAAAGNGTGA    420

GANTCACATT CTGTAACCAC CAGTGGTGAA ATGGGTCCCC GAACAAGGTA GAACATACTC    480

CCAGCCATTA ACCCCAGGGA GNGTTCAAGT CCGTNC                              516

(2) INFORMATION FOR SEQ ID NO: 56:

(i) SEQUENCE CHARACTERISTICS:
        (A) LENGTH: 505 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO: 56:

GGATCCTGTT TCTTAAAACA GAAAAAAATT TACTGATAGN ACATTGTTCT AAGTGTATTA      60

TTGTATTAAA TGGATCATTT AATTTAATCT TCATAACTGA CATAGGAGTT GAGTAACTTG     120

TGTGGTCAAA TAGCTAGTAA GTGATGAGTA GGCTGGGCGC AGTGGNTCAA GCCTGTAATC     180

CCAGCACTCT GGGAGGCTGA GGCAGGCAGA TCACTTGAGG TCAGGAGTTT GAGACCAGCC     240

TGGCCAACAT GGNAAAACCT CGTCTCTACT AAAAATACAA AAATTAGCTG GCGTGGTGG      300

GTGCGCACTT GTAGTCCCAG CTACTCGGAA GGGTTGAGGC AGGAGGAATC GCTTGGTCCC     360

CGGGAGGGAG AGGTTGNTNG TGNAGCTGAG ATCACGCCAC TNGCACTCCA GGCTGGGNAA     420

CAAAAGGGAG ACCTTTNCTC AAAAAAAAAT NAAAATAAAA AGTGATGAGT AGGATTGGGA     480

CCCNAGACAT CTTTTCTCCA AGACC                                          505

(2) INFORMATION FOR SEQ ID NO: 57:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 57:

CTGCAGNCTC AAACCCTTGT CCTGGGATCA AACAATCCTC CCACCTCAGC CTTCAAAGTA      60

GATAGAACTA CAGGCATGCA CTACCATGCC TAATTTTTTA AAAAAAATT TTTTTTCAGA     120

GATGAGATCT CACTGTGTTT CCCAGGNTTG TCCGGAACTC CTGGACTCAA GCGATCCTCC     180

CACCTTGGGC TGCCAAAGTG TTGGGATTAC AGGCATGAGC CACCATGCCT GGCCATACAC     240

TTTTTTTTTT TTTTTAANCA AGACGGAGTC TNGTTCTGTC GCCCAGACTG GAGTGCAGGG     300

GCGTNNATCT TGGCTCACTT GAAAGCTTCG CCTCCCAGGG TTCATGCCGT TCTCCTGNCT     360

CAGCCTCCCA AGTNGGTGGG ACTACAGGNA TCTGCACCAC GNCCGGTTAT TTNTTGGGTT     420

TGNNGNAGGG ACGGGGTTTC ACCATGTTAG GCAGGATGAC TTCGGACTTC CNGACCCAAG     480

ATCACCCTGC TCGGCTCCCA                                                500

(2) INFORMATION FOR SEQ ID NO: 58:

(i) SEQUENCE CHARACTERISTICS:
        (A) LENGTH: 440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 58:

GAATTCCAGA CGAGCCTGGG CAACACAGTG AGACTCTATC ACTACAAAAA AATTTTAAAA      60

TTAGCTAAAG TTGATGGNAC ATGCCTGCAG TCCCAGCTAC TCAGGAGGCT GGGGCAGGAA     120

GATAGCTTGA GCCTGGGAGT TAGAGGCTGT GTGAGCTATG ATCACACTAC TGCACTCCAG     180

CCTGGGCAAC ACAGCAAGAC CCTAAAACTA AAAAGAAAA GAAAAAAAAA ATATATGTAC      240

GTNTTTGGGG AATTTCAAAG TGGGAGATAA ATCATTTTTC CAGACAGTNT CTTGAAACCC     300

AAAGTTTATG CTTAAATAAA GGTGTGCTTT CTTTCACCTT CAAANGCGGG AGAAGGATCA     360

```
TCATNCACAC ACACACACTN ATCATNCACA TTTTTACAAA TNCAATTNNN NAATACAACA      420

CATTTTAACA TGGGGTTTTG                                                  440

(2) INFORMATION FOR SEQ ID NO: 59:

(i) SEQUENCE CHARACTERISTICS:
        (A) LENGTH: 513 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 59:

GGATCCTGTT TCTTAAAACA GAAAAAAATT TACTGATAGN ACATTGTTCT AAGTGTATTA       60

TTGTATTAAA TGGATCATTT AATTTAATCT TCATAACTGA CATAGGAGTT GAGTAACTTG      120

TGTGGTCAAA TAGCTAGTAA GTGATGAGTA GGCTGGGCGC AGTGGCTCAA GCCTGTAATC      180

CCAGCACTCT GGGAGGCTGA GGCAGGCAGA TCACTTGAGG TCAGGAGTTT GAGACCAGCC      240

TGGCCAACAT GGNAAAACCT CGTCTCTACT AAAAATACAA AAATTAGCTG GCCGTGGTGG      300

NTGCGCACTT GTAGTCCCAG CTACTCGGAA GGCTNGAGGC AGGAGGAATC GCTTGATCCC      360

NGGGAGGGAG AGGTTGGTNG TGANGCTGAG ATCACGNCAC TTGNACTCCA GNCTGGGNAA      420

CAAANGNGAG ATCTTNTCTC AAAAAAAAAT AAAANTAAAA NGTGATGAGT AGGATTTGGA      480

CCCCAGACAT CCTNTCTCCA GGACCTGGNA TTC                                  513

(2) INFORMATION FOR SEQ ID NO: 60:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 60:

GAATTCCTGG NCTCAAGTGA TCCTCTCACC TCAGCCTCCC AAATTGCTGG GATTAGAGTG       60

TGAGCCACTG TGCCTAGCCT GCATATATCT ATTTTTAATG ACTGCTAAAT CTCATTGTAT      120

GAAAATTTAT GTCCTAGCTA TAAAATTTGN TAGCACATGT TTAATTTTTT CTAATTTCAG      180

ATGTTTTAAA CTAATATTTC CCAAAGTATA GTATGGCATT TTAGGTATGA TATGATCTTT      240

NNTCCTCTTC GTACTCATTT TTATAGTTAT GGCCTGTGCA ACTGGTTTCC CATTTATATG      300

AATGATACAG AGCTTCCTAT TAAGAAAAAG TTCAGCTTGG GGAAAAAAAA AGTGAATTGT      360

CAACTTNGAG GGAAAAAAGT GAATTATTGG                                      390

(2) INFORMATION FOR SEQ ID NO: 61:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 61:

TCAAGTACCT CCCTGAATGG ACTGCGTGGC TCATCTTGGC TGTGATTTCA GTATATGGTA       60

AAACCCAAGA CTGATAATTT GTTTGTCACA GGAATGCCCC ACTGGAGTGT TTTCTTTCCT      120
```

| CATCTCTTTA TCTTGATTTA GAGAAAATGG TAACGTGTAC ATCCCATAAC TCTTCAGTAA | 180 |
| ATCATTAATT AGCTATAGTA ACTTTTTCAT TTGAAGATTT CGGCTGGGCA TGGTAGCTCA | 240 |
| TGCCTGTAAT CTTAGCACTT TGGGAGGCTG AGGCGGGCAG ATCACCTAAG CCCAGAGTTC | 300 |
| AAGACCAGCC TGGGCAACAT GGCAAAACCT CGTATCTACA GAAAATACAA AAATTNGNCG | 360 |
| GGNATG | 366 |

(2) INFORMATION FOR SEQ ID NO: 62:

(i) SEQUENCE CHARACTERISTICS:
        (A) LENGTH: 498 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 62:

| AACACCAGGG NCATGAGGGC ACTAATCATA ATGAGATATG CCTGCTGGAG TCGAAGTGGA | 60 |
| CCTTTCCAGT GAATGGAAAT CATTCCCACC ACACCAAAAT TCCAGATCAG GAGTGNAACA | 120 |
| GTAATGTAGT CCACAGCAAC GTTATAGGTT TTAAACACTT CCCTGAAAAA AAATTACACA | 180 |
| GATTTTAAAA GATGTACAAT AATTTCCACC AAAACATTAT TTAGAATAAT GTGATGGCTC | 240 |
| CCAAACATTA GATATTAATN TCCCACCTTT ATAATTTTAC CATAACCTAT ATCAACTGTG | 300 |
| CTATTATTTA TTTAATNCTT CCCTNTAAAT TAATTTACTC TTTTTTTGTT TTTGTTTTG | 360 |
| NGTTTGGAGC CAGTGTCTCA TTTTGGTTGC CCAGGCTTGG AGTAAAGTGG GTGCAATCAC | 420 |
| GGCTCAACTG NAGTCTTTNC CTCCNGGAGA TCAGGTNGGT CTTCCCCAGG TCCAANCTCC | 480 |
| TAAGTTGGTT NGGANAAC | 498 |

(2) INFORMATION FOR SEQ ID NO: 63:

(i) SEQUENCE CHARACTERISTICS:
        (A) LENGTH: 469 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 63:

| TAAACAACAG GGNCATGAGG GCACTAATCA TAATGAGATA TGCCTGCTGG AGTCGAAGTG | 60 |
| GACCTTTCCA GTGAATGGAA ATCATTCCCA CCACACCAAA ATTCCAGATC AGGAGTGAAA | 120 |
| CAGTAATGTA GTCCACAGCA ACGTTATAGG TTTTAAACAC TTCCCTGAAA AAAAATTACA | 180 |
| CAGATTTTAA AAGATGTACA ATAATTTCCA CCAAAACATT ATTTAGAATA ATGTGATGGC | 240 |
| TCCCAAACAT TAGATATTAA TNTCCCACCT TTATAATTTT ACCATAACCT ATATCAACTG | 300 |
| TGCTATTATT TATTTAATNC TTCCCTCTAA ATTAATTTAC TCTTTTTTTG TTTTTGTTTT | 360 |
| TGTGTTTGGA GCCAGTGTCT CATTTTGGTT GCCCAGGCTT GGAGTAAAGT GGGTGCAATC | 420 |
| ACGGCTCAAC TGNAGTCTTT ACCTCCCGGA GATCANGTTG GTCTTTCCC | 469 |

(2) INFORMATION FOR SEQ ID NO: 64:

(i) SEQUENCE CHARACTERISTICS:
        (A) LENGTH: 370 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 64:

| | | | | | |
|---|---|---|---|---|---|
| GTTTATCAAG | TACCTCCCTG | AATGGACTGN | GTGGCTCATC | TTGGCTGTGA | TTTCAGTATA | 60 |
| TGGTAAAACC | CAAGACTGAT | AATTTGTTTG | TCACAGGAAT | GCCCCACTGG | AGTGTTTTCT | 120 |
| TTCCTCATCT | CTTTATCTTG | ATTTAGAGAA | AATGGTAACG | TGTACATCCC | ATAACTCTTC | 180 |
| AGTAAATCAT | TAATTAGCTA | TAGTAACTTT | TTCATTTGAA | GATTTCGGCT | GGGCATGGTA | 240 |
| GCTCATGCCT | GTAATCTTAG | CACTTTGGGA | GGCTGAGGCG | GGCAGATCAC | CTAAGCCCAG | 300 |
| AGTTCAAGAC | CAGCCTGGGC | AACATGGCAA | AACCTCGTAT | CTACAGAAAA | TACAAAAATT | 360 |
| AGCCNGGNAT | | | | | | 370 |

(2) INFORMATION FOR SEQ ID NO: 65:

(i) SEQUENCE CHARACTERISTICS:
        (A) LENGTH: 316 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 65:

| | | | | | |
|---|---|---|---|---|---|
| GTCATGGTGT | TGGCGGGGAG | TGTCTTTTAG | CATGCTAATG | TATTATAATT | AGCGTATAGT | 60 |
| GAGCAGTGAG | GATAACCAGA | GGTCACTCTC | CTCACCATCT | TGGTTTTGGT | GGGTTTTGGC | 120 |
| CAGCTTCTTT | ATTGCAACCA | GTTTTATCAG | CAAGATCTTT | ATGAGCTGTA | TCTTGTGCTG | 180 |
| ACTTCCTATC | TCATCCCGNA | ACTAAGAGTA | CCTAACCTCC | TGNAAATTGA | AGNCCAGNAG | 240 |
| GTCTTGGCCT | TATTTNACCC | AGCCCCTATT | CAAAATAGAG | TNGTTCTTGG | NCCAAACGCC | 300 |
| CCTGACACAA | GGATTT | | | | | 316 |

(2) INFORMATION FOR SEQ ID NO: 66:

(i) SEQUENCE CHARACTERISTICS:
        (A) LENGTH: 448 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 66:

| | | | | | |
|---|---|---|---|---|---|
| CTGCAGNCCG | GGGGATCCTG | GTAAAAGTCA | CAAGGTCAGC | CTACTAAAGC | AGGGAAAACT | 60 |
| AAAGGCAAGT | AAACACGTGC | AGACAAAAAA | AGGGATAAAG | AAAAGGAATT | AAGAAACTAG | 120 |
| CATTTTTAAN | GTGGGGGAGG | TGAATGCTTC | CCAGAATGGG | TTTATATCAC | TTGCTTGNGG | 180 |
| GCCTTCTGAG | TGTTGGNAAC | AACCTGTCAT | CATCACACAT | ACCTGTCATC | TTTAATGGTC | 240 |
| TCCATACATT | ACTAATAGAT | TATACAGATG | GCCATCACTT | AACACTTCCA | CTCACTCAAT | 300 |
| TTGTNCAACA | TGCAAGGTTA | CCCTCTTTTT | TNGCTTACNG | CCACAAAGCA | TTGGANAAGG | 360 |
| TTTGTGATTT | TTACTAGCCN | CCACTTCATC | AAATTTAAGC | ATTTTCTTTT | TCCTNTTAAC | 420 |
| ANCCAGGACA | GGNTTNAACN | AAGGAAAT | | | | 448 |

(2) INFORMATION FOR SEQ ID NO: 67:

(i) SEQUENCE CHARACTERISTICS:
        (A) LENGTH: 450 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO: 67:

CTGCAGCTCC AAGCACCTTT TTCAAATTCA GCTTTCTGTG ATTTCAGACC ACATATGCAA      60

GGAACTATCT TACCTTAATT AATAAGACTT TAAAATCCTT GTGTCAGAGG CGTTTGGACC     120

AGAGCAACTC TATCTTGAAT AGGGGCTGGG TAAAATAAGG CCAAGACCTA CTGGGCTGCA     180

TTTGCAGGAG GTTAGGTACT CTTAGTTACG GGATGAGATA GGAAGTCAGC ACAAGATACA     240

GCTCATAAAG GATCTTGCTG ATAAAACTGG TTGCAATAAA GAAGCTGGNC AAAACCCACC     300

AAAACCAAGA TGGTGAGGAG AGTGACCTCT GGTTATCCTC ACTGNTCACT ATACGNTAAT     360

TATTATACAT TAGCATGCTA AAAGACACTC CCCGCAACAA CCATGANAGG TTTACAAGTT     420

NCCATGGNAA CGNNCCCGGA NGNTANCTTG                                     450

(2) INFORMATION FOR SEQ ID NO: 68:

(i) SEQUENCE CHARACTERISTICS:
        (A) LENGTH: 388 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 68:

CTGNAGCCTC CACCACCCAG GTTCAGGTGA TTCTCCTGCC GTAGNCTCAT GAGTAGNTGG      60

GATTACAGGC ATGTGCCACC ATGCCCGACT AATTTTTATA TTTTTAGTAG AGACGGGGTT     120

TCACCATGTT GGGCAGGCTG GTCTCAAACT CCTGACCTCA AGTGATCTGC CCACCTTGGC     180

CTCCCAAAGT GCTGGGATTT CAGGCGCCTG GCCTGTTACT TGATTATATG CTAAACAAGG     240

GGTGGATTAT TCATGAGTTT TCTGGGAAAG AGGTGGGCAA TTCCCGGAAC TGAGGGATCC     300

CTCCCCTTNN NAGACCATAC AAGGTAACTT CCGGACGTTG GCATGGNATC TTGTTAAACT     360

TGTCATGGNG TTGGGGGGA GTGTCTTT                                        388

(2) INFORMATION FOR SEQ ID NO: 69:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 69:

CTGCAGAAGT ATGTTTCCTG TATGGTATTA CTGGATAGGG CTGAAGTTAT GCTGAATTGA      60

ACACATAAAT TCTTTTCCAC CTCAGGGNCA TTGGGCGCCC ATTGCTCTTC TGCCTAGAAT     120

ATTCTTTCCT TTTCTAACTT TGGTGGATTA AATTCCTGTC ATCCCCCTCC TCTTGGTGTT     180

ATATATAAAG TNTTGGTGCC GCAAAAGAAG TAGCACTCGA ATATAAAATT TTCCTTTTAA     240

TTCTCAGCAA GGNAAGTTAC TTCTATATAG AAGGGTGCAC CCNTACAGAT GGAACAATGG     300

CAAGCGCACA TTTGGGACAA GGGAGGGGAA AGGGTTCTTA TCCCTGACAC ACGTGGTCCC     360

NGCTGNTGTG TNCTNCCCCC ACTGANTAGG GTTAGACTGG ACAGGCTTAA ACTAATTCCA     420

ATTGGNTAAT TTAAAGAGAA TNATGGGGTG AATGCTTTGG GAGGAGTCAA GGAAGAGNAG     480
```

```
GTAGNAGGTA ACTTGAATGA                                                  500
```

(2) INFORMATION FOR SEQ ID NO: 70:

(i) SEQUENCE CHARACTERISTICS:
        (A) LENGTH: 435 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 70:

```
CTGCAGAGTA ATTGCAACTG GAGTTGTCTT AAGATAATGT CACATATCCA TCTTCCCCTT       60
GTTTCTCATT CACAGAAAAA CATTTTTATT CCAGGTGCCA ATATTCCCAG CCAAAAAGAC      120
TTTACTTCTG ACTCCCTTAT ATTTAGGATG GCTATGAGAA CAAGTAAGGG CAATGACTTC      180
TAGGGAGATG TGTTGTGTAT GGAACTTCTA AGGAGAGAAT TCTGCTGACA TGTCCTATGT      240
TCTTTTCTCC CCTACTCCTT CCTACTGTCA GAAATGAAGG CTAGGGCTCC AGCCTGGACC      300
CTGAAGTAAG CTAGAGGTTA GAAGCTAAAG AAGAAAGAAG GAGATTGAGT CCTTGGATGA      360
ACGTGAAGCC ACCCTACTAA TCTGGACTGN CTACCTCTGN ACTACTCTAT GAGAGAGAAA      420
GTATGTGCAT TATTT                                                      435
```

(2) INFORMATION FOR SEQ ID NO: 71:

(i) SEQUENCE CHARACTERISTICS:
        (A) LENGTH: 439 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 71:

```
CATGCTCTTT GTCCCTGTGA CTCTCTGCAT GGTGGTGGTC GTGGNTACCA TTAAGTCAGT       60
CAGCTTTTAT ACCCGGAAGG ATGGGCAGCT GTACGTATGA GTTTGGTTTT ATTATTCTCA      120
AAGCCAGTGT GGCTTTTCTT TACAGCATGT CATCATCACC TTGAAGGCCT CTGCATTGAA      180
GGGGCATGAC TTAGCTGGAG AGCCCATCCT CTGTGATGGT CAGGAGCAGT TGAGAGAGCG      240
AGGGGTTATT ACTTCATGTT TTAAGTGGAG AAAAGGAACA CTGCAGAAGT ATGTTTCCTG      300
TATGGTATTA CTGGATAGGG CTGAAGTTAT GCTGAATTGA ACACATAAAT TCTTTTCCAC      360
CTCAGGGGCA TTGGGCGCCC ATTGNTCTTC TGCCTAGAAT ATTCTTTCCT TTNCTNACTT      420
GGGNGGATTA AATTCCTGT                                                  439
```

(2) INFORMATION FOR SEQ ID NO: 72:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 72:

```
TCCATCTCTA CGACTCTCAT GGGGTCCAAA GAAGAGTTTT AATTGAGTTT TAGAATGTGN       60
AGTTGTGAAG TGTCTGAAAA ACTACATGGT GNTCTGAAAG NCAAACTTTT AGCCTTGGGG      120
GAGAGCATCT AAGACAGNAG GTGAAGGGGA GGGGTTAGAN CTAGAGGGAT TGAAGAATAT      180
```

-continued

```
TATCCATATA GGTTAGGGTT AGGTGTGGCA ACGTTTTATA GAACAAACAT TGGNAAGCTA        240

CAGACACAGG CCAGNTCTGT CTNCTACCTN TCCACAAAGG TGTNATAACA AAGTTANNCA        300

CAAATGTGTG AATAAACT                                                     318
```

(2) INFORMATION FOR SEQ ID NO: 73:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 73:

```
GTTGCAAAGT CATGGATTCC TTTAGGTAGC TACATTATCA ACCTTTTTGA GAATAAAATG         60

AATTGAGAGT GTTACAGTCT AATTCTATAT CACATGTAAC TTTTATTTGG ATATATCAGT        120

AATAGTGCTT TTTCNTTTTT TTTTTTTNTT TTTTTTNNTT TTNGGGGANA GAGTCTCGCT        180

CTGTCGCCAG GTTGGAGTGC AATGGTGCGA TCTTGGCTCA CTGAAAGCTC CACCNCCCGG        240

GTTCAAGTGA TTCTCCTGCC TCAGCCNCCC AAGTAGNTGG GACTACAGGG GTGCGCCACC        300

ACGCCTGGGA TAATTTTGGG NTTTTTAGTA GAGATGGCGT TTCACCANCT TGGNGCAGGC        360

TGGTCTTGGA ACTCCTGANA TCATGATCTG CCTGCCTTAG CCTCCCCAAA GTGCTGGGAT        420

TNCAGGGGTG AGCCACTGTT CCTGGGCCTC                                        450
```

(2) INFORMATION FOR SEQ ID NO: 74:

(i) SEQUENCE CHARACTERISTICS:
        (A) LENGTH: 489 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 74:

```
CTGCAGNTGA GCCGTGATTG CANCCACTTT ACTCCNAGCC TGGGCAANCA AAATGAGACA         60

CTGGCTNCAA ACACAAAAAC AAAAACAAAA AAAGAGTAAA TTAATTTAAA GGGAAGTATT        120

AAATAAATAA TAGCACAGTT GATATAGGTT ATGGTAAAAT TATAAAGGTG GGATATTAAT        180

ATCTAATGTT TGGGAGCCAT CACATTATTC TAAATAATGT TTTGGTGGAA ATTATTGTAC        240

ATCTTTTAAA ATCTGTGTAA TTTTTTTTCA GGGAAGTGTT TAAAACCTAT AACGTTGCTG        300

TGGACTACAT TACTGTTGCA CTCCTGATCT GGAATTTTGG TGTGGTGGGA ATGATTTCCA        360

TTCACTGGAA AGGTCCACTT CGACTCCAGC AGGCATATCT CATTATGATT AGTGCCCTCA        420

TGGCCCTGGT GTTTATCAAG TACCNCCCTG AATGGACTGG GTGGCTCATC TTGGCTGTGA        480

TTTCAGTAT                                                               489
```

(2) INFORMATION FOR SEQ ID NO: 75:

(i) SEQUENCE CHARACTERISTICS:
        (A) LENGTH: 449 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 75:

```
CTGCAGNCTT GACCTCCTGG GATCAATCGA TCCTCCCACC TCAGCCTCCT AAGTAGCTGG      60

AACTACAGGT GTGCACCACC ATGCCCGGCT AATTTTTGTA TTTTCTGTAG ATACGAGGTT     120

TTGCCATGTT GCCCAGGCTG GTCTTGAACT CTGGGCTTAG GTGATCTGCC CGCCTCAGCC     180

TCCCAAAGTG CTAAGATTAC AGGCATGAGC TACCATGCCC AGCCGAAATC TTCAAATGAA     240

AAAGTTACTA TAGCTAATTA ATGATTTACT GAAGAGTTAT GGGATGTACA CGTTACCATT     300

TTCTCTAAAT CAAGATAAAG AGATGAGGAA AGAAAACACT CCAGTGGGGC ATTCCTGTGA     360

CAAACAAATT ATCAGTCTTG GGTTTTACNA TATACTGAAA TCACAGCCAA GATGAGCCAC     420

GCAGTCCATT CAGGGAGGTA CTTGATAAA                                      449
```

(2) INFORMATION FOR SEQ ID NO: 76:

(i) SEQUENCE CHARACTERISTICS:
        (A) LENGTH: 490 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 76:

```
TTCTTGCCGT TCCCGACCCG AGCCTGGTGC CCCTTCCCCA TTATGATCCT TNTCGCTTCC      60

GGCGGCATCG GGATGCCCCG CGTTGCAGGC CATNCTGTCC CAGNCAGGTA GATGACGACC     120

ATCAGGGACA GCTTCAAGGA TCGCTCGCGG CTCTTACCAG CCTAACTTCG ATCATTGGAC     180

CGCTGATCGT CACGGCGATT TATCCCGCCT CGGCGAGCAC ATGGAACGGG TTGGCATGGA     240

TTGTAGGCGC CGCCCTATAC CTTGTCTGCC TCCCCCGCGT TGCGTCGCGG TGCATGGAGC     300

CGGNCCACCT CGACCTGAAT GGAANCCGGC GGCACCTCGC TAACGGATTC ACCACTCCAA     360

GAATTGGAGC CAATCAATTC TTGCGGAGAA CTGTGAATGC NCAAACCAAC CCTTGGCAGA     420

ACATATCCAT CGCGTCCGCC ATCTCCANCA GCCGCACGCG GCGCATCTCG GGCAGCGTTG     480

GGTCCTGCAG                                                           490
```

(2) INFORMATION FOR SEQ ID NO: 77:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 77:

```
CTGCAGTGTT TAAAAAATAA AATAAACTAA AAGTTTATTT ATGAGGAGTA CACTGCTTTC      60

TTGTAAACAC ATGTACAAGC CATATAATAG AGTTCATTTC NNACCCTAGT TACGAAACA     120

CTAGAAAGTC TNCACCCGGC CAAGATAACA CATCTTTAGG TAAAAATAGC AAGAAATATT     180

TTATGGGTTG TTTACTTAAA TCATAGTTTT CAGGTTGGGC ACAGTGGNTC ATGCCTGTAA     240

TCCCAGCACT TTATGCGGCT GAGGCAGGCA GATCAGTTGA GGTCAGAAGT TTGAGACCAG     300

CCTGGGCAAT GTGGCAAAAC CTCATCTCCA CTAAAAATAC AAAAATTAGC CAGGCATGGT     360

GGTGCACACA TGTTAATTCC CAGCTACTTG GGAGGNTTGA GACAGGAGGG TCGCTTGGNC     420

CTAGGAGGGA AGAAGTTGNA GGGANCTTAA TGTCACTGCA CTCTAGNTTG                470
```

(2) INFORMATION FOR SEQ ID NO: 78:

```
    (i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 78:

CACTCAATTC TGAATGCTGC CATCATGATC AGTGTCATTG TTGTCATGAC TANNCTCCTG      60

GTGGTTCTGT ATAAATACAG GTGCTATAAG GTGAGCATGA GACACAGATC TTTGNTTTCC     120

ACCCTGTTCT TCTTATGGTT GGGTATTCTT GTCACAGTAA CTTAACTGAT CTAGGAAAGA     180

AAAAATGTTT TGTCTTCTAG AGATAAGTTA ATTTTTAGTT TTCTTCCTCC TCACTGTGGA     240

ACATTCAAAA AATACAAAAA GGAAGCCAGG TGCATGTGTA ATGCCAGGCT CAGAGGCTGA     300

GGCAGGAGGA TCGCTTGGGC CCAGGAGTTC ACAAGCAGCT TGGGCAACGT AGCAAGACCC     360

TGCCTCTATT AAAGAAAACA AAAACAAAT ATTGGAAGTA TTTTATATGC ATGGAATCTA      420

TATGTCATGA AAAAATTAGT GTAAA                                          445

(2) INFORMATION FOR SEQ ID NO: 79:

(i) SEQUENCE CHARACTERISTICS:
         (A) LENGTH: 496 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 79:

CCTGTATTTA TACTGAACCA CCAGGAGGAT AGTCATGACT ACAATGACNC TGATCATGAT      60

GGCAGCATTC AGAATTGAGT GCAGGGCTCT CTGGCCCACA GTCTCGGTAT CTTCTGTGAA     120

TGGGGTATAG ATTCTACAAT AAAACAAACA CAAAAGCCCT AGGTCAGTGT TAATGGAGAT     180

CACCAACCAC ATTACCACCT CCAACACAGA ATTTTCTTTT TCTTAATTCA ATTCGNATCT     240

TATAAGTCAC TTTTCCCCAA CTCACCAATN CTAGCTAAGA ATTTTTAACC TGAGAAAAAC     300

AGCTACACTC TAAAATTGCT TCAAAGAAAA TGTCTAACAT ATGGAAAGAA GGACTTAACA     360

TGTGAAGCAG ACACTGGCTC CATCTAGTGG GTGCTTTATA TTGAAATAAT TATAATACCT     420

CATCAAATTT TTTNGGGTAC AGNTTATTAG GAACTTGGTA TGGAACCAGA TTCTGCCACA     480

GAAACCACGN GGGCTG                                                    496

(2) INFORMATION FOR SEQ ID NO: 80:

(i) SEQUENCE CHARACTERISTICS:
         (A) LENGTH: 496 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 80:

CATTAGATAA TGGNTCAGGG TGGCCAAGGC TCCGTCTGTC GTTGTGCTCC TGCCGTTCTC      60

TATTGTCATT CTATAAGCAC AAGAAAAACA TTTTCAGTAA ATCAGATTCT CAGCAGAATC     120

AAGGTAACGG TTAGACCTGG GATTAACAAC AGACCCGTCA CTATGAGTTC TAAAAACCTG     180

AAGCAAGAAA AAACAATGTA CAGGAAGTAT GCAGTTTAAA AGTCTAGATT ATCTATCATT     240

GTTCACTGAA GGCATTCAGG TCCTCTCTTT TACCTGGGTC TTGGNTTGCT CCATTCTCTC     300
```

```
TGTTCATCCC AACATACACA ATTGTACTTA TCCTTTGAGA TGTACCTTAA ATACTGACAC    360

CTGCATGAAA ACTTGTTTAC TGGCTGCAGG TCCAAGCACC TTTTTCNAAA TTCAGCTTTC    420

TGTGATTTCA GACCACATAT GCAAGGAACT ATCTTACCTT AATTAATAAG ANTTTAAAAT   480

CCTTGTGTCA GAGGCG                                                    496

(2) INFORMATION FOR SEQ ID NO: 81:

(i) SEQUENCE CHARACTERISTICS:
        (A) LENGTH: 368 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 81:

AGGANCGCTT GGGCCCAGGA GTTCACAAGC AGCTTGGGCA ACGTAGCAAG ACCCTGCCTC     60

TATTAAAGAA AACAAAAAAC AAATATTGGA AGTATTTTAT ATGCATGGAA TCTATATGTC    120

ATGAAAAAAT TAGTGTAAAA TATATATATT ATGATTAGNT ATCAAGATTT AGTGATAATT    180

TATGTTATNN NGGGATTTCA ATGCCTTTTT AGGCCATTGT CTCAAAAAAT AAAAGCAGAA    240

AACAAAAAAA GTTGTAACTG AAAAATAAAC ATTTCCATAT AATAGCACAA TCTAAGTGGG    300

TTTTTGNTTG TTTGTTTGNT TGTTGAAGCA GGGCCTTGCC CTNCCACCCA GGNTGGAGTG    360

AAGTGCAG                                                             368

(2) INFORMATION FOR SEQ ID NO: 82:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 82:

GAATTCCTTT TTTTTTTTTT TTTTTTTTTT TTNCTCCTAA TGTTTTTATT GTNCCTTAGA     60

TAACTGGATA GNACAAAGTT NGNCTTNGTT TTTTACTTAA AAAACGTACT TTCCGCATAC    120

TGTNGCCCGT ATGACTTTCC TGTCCCATCG GAAACCAGAG TTTCCCCAGG TGAGCCCTTC    180

CTATCTGNGG NTACATGATT TAGCTAATTT AACAAGAAGA GAGTAATTCC TTNGGATTAT    240

TATCAACATG AAACTTGGAC TATGTCTCTA TAAGGGTGAA CACTGATTTT TTTTTTCTTT    300

TTAGAAACAA AAACCATCCA CTTATTAATC CAAACTACGG GATTGGATTT ACAACAATCA    360

TCGCATNAAC TGAACATACG AAGTTACCAC TCAAGGGAAT NACAGAAGAA CGTTGNACAA    420

TNTNTCTTAC GGGGTACGNG AATTCAAACA ATGTGGGGAN AGGAACTTCA NTCTACAAAN    480

TCTGACCATC GNTTCAGTAT                                                500

(2) INFORMATION FOR SEQ ID NO: 83:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 83:
```

```
GAATTCCTTT ACTCTTCTTT AATTCTACCG TCTTTGGGCA TACATCTCAT TTGNTGTGGA      60

AGAAGGTCTG ACAGNAGGGC TGACAGCACC GATTCATAAC ACATTCTTTT CATCATACAA     120

AGAGTAAGAC CCTAGAATAA TGGGACCATC TGCTACCACG ACAGAGCTGC CTTACTGGCT     180

GTAGAAAAAG ACTGCTTGTG TGGGAGAGAA GAATGAGGAC AGAGGAGGCA TCTGGGCAA      240

GTGAGCGTAC AAGTATNTCT ACAAATTCAG AATTTGGTGG AAAATCCAAA TTTGNCTTCA     300

ACATGATAGA GAATTGATGA GAAAATAGCT GTNCTGTTTC CAAAATTTAC TGAATTTGGG     360

AACCTGAGGT TAAAACTTTT AGGATNAAGC AACTCAGGTT CAAGACTTNG NCTNGGGAAG     420

GAATGGAAAC ACAGACGGGA ATGAGTNTCA                                      450
```

(2) INFORMATION FOR SEQ ID NO: 84:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 84:

```
CAACTGTATT TATACAGNAA CCACCAGGAG GATAGTCATG ACAACAATGA CAAACTAGGA      60

ATAGCCCCCT TTCACTTCTG AGTCCCAGAG GTTACCCAAG GCACCCCTCT GACATCCGGC     120

CTGCTTCTTC TCACATGANA AAAACTAGCC CCCAGTNTGA TCCGCAGGTN GAGGAATNCC     180

CCGGGTCGAG GTTCGGATCC TGGATGACAG ACCCTCTCGC CCCTGAAGGN GATAACCGGG     240

TGTGGTACAT GGACGGNTAT CACAACAACC GCTTCGNACG TGAGTACAAG TCCATGGTTG     300

ACTTCATGAA CACGGACAAT TTCACCTCCC ACCGTCTCCC CCACCCCTGG TCGGGCACGG     360

GGNAGGTGGT CTNCAACGGT TCTTTCTNCT TCAACAAGTT CCAGAGCCAC ATCATCATCA     420

GGTTTGGACC TGAAGANAGA GAACATCCTC                                     450
```

(2) INFORMATION FOR SEQ ID NO: 85:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 85:

```
GGATCCCTCC CCTTTTTAGA CCATACAAGG TAACTTCCGG ACGTTGCCAT GGCATCTGTA      60

AACTGTCATG GTGTTGGCGG GGAGTGTCTT TTAGCATGCT AATGTATTAT AATTAGCGTA     120

TAGTGAGCAG TGAGGATAAC CAGAGGTCAC TCTCCTCACC ATCTTGGTTT TGGTGGGTTT     180

TGGCCAGCTT CTTTATTGCA ACCAGTTTTA TCAGCAAGAT CTTTATGAGC TGTATCTTGT     240

GCTGACTTCC TATCTCATCC CGTAACTAAG AGTACCTAAC CTCCTGCAAA TNGCAGCCCA     300

GTAGGTCTTG GNCTTATTTT ACCCAGCCCC TATTCAAGAT AGAGTTGCTC NTGGTCCAAA     360

CGCCTCTGAC ACAAGGATTT TAAAGTCTTA TTAATTAAGG TAAGATAGGT CCTTGGATAT     420

GTGGTCTGAA ATCACAGAAA GCTGAATTTG GAAAAGGTG CTTGGAGCTG CAGCCAGTAA      480

ACAAGTTTTC ATGCAGGTGT                                                 500
```

(2) INFORMATION FOR SEQ ID NO: 86:

```
    (i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 86:

CTGCAGTGAG CCAAAATCGT GCCACTGCAC TTCACTCCAG CCTGGGTGAC AGGGCAAGGC      60

CCTGCTTCAA CAAACAAACA AACAAACAAA AACCCACTTA GATTGTGCTA TTATATGGAA     120

ATGTTTATTT TTCAGTTACA ACTTTTTTTG TTTTCTGCTT TTATTTGTTG AGACAATGGC     180

CTAAAAAGGC ATTGAAATNC CAAAATAACA TAAATTATCA CTAAATCTTG ATAACTAATC     240

ATAATATATA TATTTTACAC TAATTTTTTC ATGACATATA GATTCCATGC ATATAAAATA     300

CTTCCAATAT TTGTTTTTTG TTTTCTTTAA TAGAGGCAGG GTCTTGCTAC GTTGCCCAAG     360

CTGCTTGTGA ACTCCTGGGC CCAAGCGATC CTCCTGCCTC AGCCTCTGAG CCTGGCATTA     420

CACATGCACC TGGCTTCCTT TTTGTNTTTT TTGAATGTTC CACAGTGAGG AGGAAGAAAA     480

CTNAAAATTA ACTTATCTCT                                                 500

(2) INFORMATION FOR SEQ ID NO: 87:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 87:

CTGCAGATGA GAGGCACTAA TTATAAGCCA TATTACCTTT CTTCTGACAA CCACTTGTCA      60

GCCCACGTGG TTTCTGTGGC AGAATCTGGT TCTATAACAA GTTCCTAATA AGCTGTAGCC     120

AAAAAAATTT GATGAGGTAT TATAATTATT TCAATATAAA GCACCCACTA GATGGAGCCA     180

GTGTCTGCTT CACATGTTAA GTCCTTCTTT CCATATGTTA GACATTTTCT TTGAAGCAAT     240

TTTAGAGTGT AGCTGTTTTT CTCAGGTTAA AAATTCTTAG CTAGGATTGG TGAGTTGGGG     300

AAAAGTGACT TATAAGATAC GAATTGAATT AAGAAAAAGA AAATTCTGTG TTGGAGGTGG     360

TAATGTGGGT GGTGATCTTC ATTAACACTG ANCTAGGGNT TTGGGGTTTG GTTTATTGTA     420

GAATCTATAC CCCATTCANA GAAGATACCG                                      450

(2) INFORMATION FOR SEQ ID NO: 88:

(i) SEQUENCE CHARACTERISTICS:
        (A) LENGTH: 502 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 88:

CTGCAGCCAG TAAACAAGTT TTCATGCAGG TGTCAGTATT TAAGGTACAT CTCAAAGGAT      60

AAGTACAATT GTGTATGTTG GGATGAACAG AGAGAATGGA GCAAGCCAAG ACCCAGGTAA     120

AAGAGAGGAC CTGAATGCCT TCAGTGAACA ATGATAGATA ATCTAGACTT TTAAACTGCA     180

TACTTCCTGT ACATTGTTTT TTCTTGCTTC AGGTTTTTAG AACTCATAGT GACGGGTCTG     240
```

```
TTGTTAATCC CAGGTCTAAC CGTTACCTTG ATTCTGCTGA GAATCTGATT TACTGAAAAT        300

GTTTTTCTTG TGCTTATAGA ATGACAATAG AGAACGGCAG GAGCACAACG ACAGACGGAG        360

CCTTGGCCAC CCTGAGCCAT TATCTAATGG ACGACCCAGG GTAACTCCCG GCAGGTGGTG        420

GAGCAAGATG AGGAAGAAGA TGAGGAGCTG ACATTGAAAT ATGGCGGCNA GCATGTGATC        480

ATGCTCNTTG GCCCTGTGAN TC                                                502
```

(2) INFORMATION FOR SEQ ID NO: 89:

(i) SEQUENCE CHARACTERISTICS:
        (A) LENGTH: 499 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 89:

```
CTGCAGTGTT CCTTTTCTCC ACTTAAAACA TGAAGTAATA ACCCCTCGNT CTCTCAACTG         60

CTCCTGACCA TCACAGAGGA TGGGCTCTCC AGCTAAGTCA TGCCCCTTCA ATGNAGAGGC        120

CTTCAAGGTG ATGATGACAT GCTGTAAAGA AAAGCCACAC TGGGTTTGAG AATAATAAAA        180

CAAAACTCAT ACGTACAGCT GCCCATCCTT CCGGGTATAA AAGCTGACTG ACTTAATGGT        240

AGCCACGACC ACCACCATGC AGAGAGTCAC AGGGACAAAG AGCATGATCA CATGCTTGGC        300

GNCATATTTC AATGTCAGNT CCTCATCTTC TTCCTCATCT TGNTCCACCA CCTGCCGGGA        360

GTTACCNTGG GTCGTCCATT AGATAATGGG TCAGGGTGGC CAAGGCTCCG TCTGTCGTTG        420

TGCTCCTGCC GTTCTCTATT GTCATTCTAT AAGCACAAGA AAAACATTTN CAGTAAATCA        480

GATNCTCAGC AGAATCAAG                                                    499
```

(2) INFORMATION FOR SEQ ID NO: 90:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 90:

```
TAACTCCCAG GNTCAAGATN TCTNCCTGCG TTAGCCTCCT GAGTAGCTGG GACTATAGGT         60

ATGTGCCACT ATTCCTGAAA ACATAATCAG TTTTGAAGGT AGTGTCTGGG CTGGGCGCAG        120

TGGNTCACGC CTTCAATCCC AGCACTTTGG GAGGNCGAGG TGGGCGGATC ACCTGAGGTC        180

AGGAGTTCGA GACCAGCCTG ACCAACATGG GATAAGACTC CATCTCTACT AAAAATACAA        240

AAAATTAGCC AGGCATGGTG GNGCATGCCT GTAATCCCAG CTACTCAGGA GGNTGAGGNA        300

GGAGAATTGG TTGGAACCTA GGAAGCAGAG GCTGTGGTGG AGCCGAGATC GCACCATTGG        360

ACTCCAGGCT GGGNAACAAG AGTGAAAATC CNTCTTAAAA AAAAAAAAAA AAAGGTAGNG        420

TTTTGNCCGG NGCGGGGGGT CACGCCTGTA ATCCCAGNAT TGGGGANGGC AAGGNGGGGG        480

GTCANNANGN NAGNAGTCCG                                                   500
```

(2) INFORMATION FOR SEQ ID NO: 91:

(i) SEQUENCE CHARACTERISTICS:
        (A) LENGTH: 502 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 91:

GAATTCTGCT GACATGTCCT ATGTTCTTTT CTCCCCTACT CCTTCCTACT GTCAGNAATG     60

AAGGGTAGGG CTCCAGCCTG GACCCTGAAG TAAGCTAGAG GTTAGAAGCT AAAGAAGAAA    120

GAAGGAGATT GAGTCCTTNG ATGAACGTGA AGCCACCGTA CTAATCTGGA CTGCCTACCT    180

CTGCACTACT CTATGAGAGA GAAAGTATGT GCATTATTTA AACCAGTTGG GTTGATTTTC    240

TATTAACAAA GTCAGAAACA TCTCTGTAAA AAGCCAGACT GAATATTTTA AGCTCTATGG    300

GTCATATGGT CTCCAGGGCA AACACTCAAC TGTGCTACTG TAGTGTGAAA GCAGGCACAG    360

ACAATGTATT AACCAAGGAG GGTGGTCACT TTCCAATGAA AGTTTATCAC AAATTGGNGA    420

ATACTTGGTA TTACACCNNG GGGGAAGGTA GGAGAAGATC TTGCCTGTGG TTGTNGNTGG    480

CAATGTTGGT CTTTTATACG NG                                            502

(2) INFORMATION FOR SEQ ID NO: 92:

(i) SEQUENCE CHARACTERISTICS:
        (A) LENGTH: 495 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 92:

GAATTCTCTC CTTAGAAGTT CCATACACAA CACATCTCCC TAGAAGTCAT TGCCCTTACT     60

TGTTCTCATA GCCATCCTAA ATATAAGGGA GTCAGAAGTA AAGTCTGGNT GGCTGGGAAT    120

ATTGGCACCT GGAATAAAAA TGTTTTTCTG TGAATGAGAA ACAAGGGGAA GATGGATATG    180

TGACATTATC TTAAGACAAC TCCAGTTGCA ATTACTCTGC AGATGAGAGG CACTAATTAT    240

AAGCCATATT ACCTTTCTTC TGACAACCAC TTGTCAGCCC ACGTGGTTTC TGTGGCAGAA    300

TCTGGTTCTA TAACAAGTTC CTAATAAGCT GTAGCCAAAA AAATTTGATG AGGTATTATA    360

ATTATTTCAA TATAAAGCAC CCACTAGATG GAGCCAGTGT CTGCTTCACA TGTTAAGTCC    420

TTCTTTCCAT ATGTTAGACA TTTCTTTGAA GCAATTTTAG AGTGTAGCTG TTTCTCAGGT    480

TAAAATTCTT AGTAG                                                    495

(2) INFORMATION FOR SEQ ID NO: 93:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 93:

TATGGTTGCC TATTCTTGTC ACAGTAACTN AACTGATCTA GGAAAGAAAA AATGTTTTGT     60

CTTCTAGAGA TAAGTTAATT TTTAGTTTTC TTCCTCCTCA CTGTGGAACA TTCAAAAAAT    120

ACAAAAGGA AGCCAGGTGC ATGTGTAATG CCAGGCTCAG AGGCTGAGGC AGGAGGATCG    180

CTTGGGCCCA GGAGTTCACA AGCAGCTTGG GCAACGTAGC AAGACCCTGC CTCTATTAAA    240

GAAAACAAAA AACAAATATT GGAAGTATTT TATATGCATG GAATCTATAT GTCATGAAAA    300

AATTAGTGTA AAATATATAT ATTATGATTA GTTATCAAGA TTTAGTGATA ATTTATGTTA    360

```
TTTTGGGATT TCAATGCCTT TTTAGGCCAT TGTCTCAAAA AAATAAAAGC AGGAAAACAA      420

AAAAAGTTGT AACTTGAAAA ATAAACATTT CCATATTTAT AGCCAACTAA GTGGGTTTNG      480

GGTNGGTTGG GTTGGTTGGT                                                  500

(2) INFORMATION FOR SEQ ID NO: 94:

(i) SEQUENCE CHARACTERISTICS:
        (A) LENGTH: 385 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 94:

TTATCATTAA CAGGTCCCAC AACCCTTAAA AAGTACAGAT TTTTTTTTTC TTNGTGGAGA       60

CAGGGTCTCA CTTGGTCGCC CAGACTGGAG TGCAGTGGCA CGATCTCAGT TCACCACAAC      120

CTCTGCCTCC TGGGTTCAAG CAATNCTCGT GCTTAAGCCT CCTGAGTAGG TGGAACCACG      180

CGTGCGCGCC ACCACGCTAG GTTNATTGTG GCTTTTTTAG TAGAGACAGG GTTTCGCCAT      240

GTTGCCCAGG CTGGTCTCAN ATTCCNGACC TCAAGTGATC CGNCCGCCTC AGACTCCCAA      300

AGTGNTGAGC ATTACAGNTG TGTACCACTA TGTCCCNGNC CNCATCTCTC TTTAAAACAN      360

CTTNCATTTA CCTAGTCCAC TCCTG                                            385

(2) INFORMATION FOR SEQ ID NO: 95:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 95:

GACCTAGAAA AGAAAGCATT TCAANNTAAT TAACAGGTCC CACAACCCTT AAAAAGTACA       60

GATTTTTTTT TTCTTTNNGG AGACAGGGTC TCACTTTGTC GCCCAGACTG GAGTGCAGTG      120

GCACGATCTC AGCTCACCAC ANCCTCTGCC TCCTGGGTTC AAGNANTTCT CGTGCTTANG      180

CCTCCTGAGT AGGTGGAACC ACGCGTGTGC GCCACCACGC TAGGCTACTT TNTGTATTTT      240

TAGTAGAGAC AGGGTTTCGC CATNTTGCCC AGGCTGNTCT CAAATTCCTG ACCCNCAAGT      300

GATCCCCCCN CCTTCAGTAC TCCCCATCAG                                       330

(2) INFORMATION FOR SEQ ID NO: 96:

(i) SEQUENCE CHARACTERISTICS:
        (A) LENGTH: 382 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 96:

GGTGGNCGTT CTAGAACTAG TGGCNCCCAA GGNAGAAGAA GTTTTCTTAG TACAGAACAA       60

AATGAAANGT CTCCCATGTC TACTTCTTTC TACACAGACA CGGCATCCAT CCGTTTTTCT     120

CANTCTTTCC NCCACCTTTC CCGTCTTTCT ATTCCACAAA GCCGNCATTG TCATCCTGGC     180

CCNTTCTCAA TGAGCTGTTG NNTACACCTC CCAGACGGCG TGGTGGNCGG TCAGAGGGGC     240
```

```
TCCTCACTTC CCAGTAGGGG TGGCCGNGCA GGNGGTGCCC CNCACCCCCC GGGCGGGGTG      300

GTTNGTCCNN CCGGNGGGNT GCACCNCCCC CACCCCTCCC CNCTCTNCTA CTGGCGGTCG      360

TNTATTNCAN NATCTTTAAG CA                                                382

(2) INFORMATION FOR SEQ ID NO: 97:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 97:

GGATCCAAAG GAAGTTAGAG GCCAGCTCAG TCTACACCTG CTACTGNTCA GTGCCCACCC       60

GGTCAAGGGA GACCAACACA TGGTAAAGGT CAAGGGCTTC TTGGAAGGCA GTCAGCAGCC      120

TGTGCAAGAT GTTCTCCACA CTGCTCAGNT TAAGGGGAGC TGGGGCAGG ACCTCAGCTG      180

GNATCTCTGC TTCACCAGTG TCCAGGGGTT GCACAATTCT TGTTTACTCG TAGGATATTT      240

AATCTTGGNN GGTGCTATCA TAAATGGGAC TTATCCNCTN ATTATGTTTT CTTACTAGTT      300

GTTTATGTGA AGGTTATTGA TTTGGGTTTC ACTTTATTTN GTGGNAATGG AGTTTCACTC      360

(2) INFORMATION FOR SEQ ID NO: 98:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 98:

AATGTCACGG ATTCCTTTAG GTAGNTACAC CCATCAACCT TTTTGAGAAT AAAATGAATT       60

GAGAGTGTTA CAGTCTAATT CTATATCACA TGTAACTTTT ATTTGGATAT ATCAGTAATA      120

GTGCTTTTTT TTTTTTTTTT TTTTTTTTTT TTTTTTTTNG GNGANAGAGT CTCGCTCTGT      180

CGCCAGGTTG GAGTGNAATG GTGCGATC                                        208

(2) INFORMATION FOR SEQ ID NO: 99:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 99:

AACAAGGTTT CTCGGTCGGC GGTGAATATA CCGGGGCGTC GATATTTGTT GCGGAATACT       60

CCCCTGACCG TAAACGTGGC TTTATGGGCA GCTGGCTGGA CTTCGGTTCT ATTGCCGGGT      120

TTGTGCTGGG TGCGGGCGTG GTGGTGTTAA TTTCGACCAT TGTCGGCGAA GCGAACTTCC      180

TCGATTGGGG CTGGCGTATT CCGTTCTTTA TCGCTCTGCC GTTAGGGATT ATCGGGCTTT      240

ACCTGCGCCA TGCGCTGGAA GAGACTCCGG CGTTCCAGCA GNATGTCGAT AAACTGGAAC      300

AGGGCGACCG TGAAGGTTTG GAGGATGGCC CGAAAGTCTC GTTTAAAGAG ATTGGCACTA      360

AATACTGGNG CAGNCTGTTG AATGTTTGGG CTTGGTAATT GGCAACCAAC GTGATTACTA      420
```

NATGTTGGTG ACCTATATTG CCGAGTTATT GGCGGATAAC CTGAATTATC      470

(2) INFORMATION FOR SEQ ID NO: 100:

(i) SEQUENCE CHARACTERISTICS:
        (A) LENGTH: 440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 100:

TAATTATATT GAAATGCTTC TCNTCTAGGT CATCCATGNC TGGNTTATTA TATCATCTCT      60

ATTGNTGNTG CTCTTTTTTA CATNCATTTA CTTGGGGTAA GTTGTGAAAT TTGGGGTCTG      120

TCTTTCAGAA TTAACTACCT NNGTGCTGTG TAGCTATCAT TTAAAGCCAT GTACTTTGNT      180

GATGAATTAC TCTGAAGTTT TAATTGTNTC CACATATAGG TCATACTTGG TATATAAAAG      240

ACTAGNCAGT ATTACTAATT GAGACATTCT TCTGTNGCTC CTNGCTTATA ATAAGTAGAA      300

CTGAAAGNAA CTTAAGACTA CAGTTAATTC TAAGCCTTTG GGGAAGGATT ATATAGCCTT      360

CTAGTAGGAA GTCTTGTGCN ATCAGAATGT TTNTAAAGAA AGGGTNTCAA GGAATNGTAT      420

AAANACCAAA AATAATTGAT      440

(2) INFORMATION FOR SEQ ID NO: 101:

(i) SEQUENCE CHARACTERISTICS:
        (A) LENGTH: 449 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 101:

AAAACAAAGC CTCTTGAGGT TCTGAAAAGG GAAAGAAAAA CAGAACTTTG TGCACTACAA      60

TTATACTGTT ATAAAAAACA CTTCCATAGA TTACATTAAG CAGAAACAAA CCTTTCTTTC      120

ATGTGTTCTC CTCCAGGCCA AGCTGTCTAA GGACCGCAAA GGCTGTTGTC ACTTGCAGGC      180

TCCCAGATTA GGTCTGAAAT AGGATTTCAC CAGGTCATCC ATTGTTAGTT AAATCCTAGT      240

AAATTCATTT ANACCAATCA ATACTTATA AGACCAATTT GTAAACCAGG AATGTATTAA      300

TTTGTCACGA CTTTCAACTA ACTGACAAAT TTACTATAAG CTCAAGGTAG GACTCTTTAG      360

CAATAAGTAG GAACCGCCTG AGACAACCAA ACATTTTCAA CCCACAAANG ATACTTTAAT      420

GACTTTCTGA TTTNCCAGCA AAAGGGGGG      449

(2) INFORMATION FOR SEQ ID NO: 102:

(i) SEQUENCE CHARACTERISTICS:
        (A) LENGTH: 425 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 102:

GGATCCGCCC TCCTCGGCCT CCCAAAGTGT TGGGATTACA GGCGTGAGCC ACCGCACCTG      60

GCTTTTTTTT TTTTTTTTTT TGGNGGAGAC AGAGTCTTAC TCTGTTGCCC AAGCTGGAGT      120

GCAGTGGTGC AATCTTGGTT CACTGNAACC TCCACCTCCA GAGTTCAAGC AATTCTCTGC      180

```
CTCAGTTTCT GGAGTAGCTG GGATTACAGG TGCCTGCCAT CACGCCTGGC TAAATTTGGN       240

ATTTTTTTTT AGTAGAGACA GGGTTTCACC ATGTTGGCCA GGCTGGTCTT GAACTCCTGA       300

CCTTGTGATC CACCAGCCTC GGCCTCCCAA ATTGNTGGGA TTACAGGCGT GAGCCACCAC       360

AACCAGGCTA AAGTTTTAAA ACATGCCAAG TGTATTTACA TAATGCGATA CGANTTATGT       420

ACATA                                                                  425

(2) INFORMATION FOR SEQ ID NO: 103:

(i) SEQUENCE CHARACTERISTICS:
        (A) LENGTH: 386 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 103:

GGATCCGCCC GCCTTGGCCT CCCAAAGTGC TGGGATTACA GGCATGAGCC ACCGCTCCTG        60

GCTGAGTCTG CGATTTCTTG CCAGCTCTAC CCAGTTGTGT CATCTTAAGC AAGTCACTGA       120

ACTTCTCTGG ATTCCCTTCT CCTNTTGTAA AATAAGCATG TTATCTGTCC NNCCTGCCTT       180

GGGCATTGTG ATAAGGATAA GATGACATTA TAGAATNTNG CAAAATTAAA AGCGCTAGAC       240

AAATGATTTT ATGAAAATAT AAAGATTAGN TTGAGTTTGG GCCAGCATAG AAAAAGGAAT       300

GTTGAGAACA TTCCNTTAAG GATTACTCAA GCTCCCTTTG GTGTATATCA GNNGTCANNA       360

CNTATCTTNG GGGCTGAAAA ATGTTT                                            386

(2) INFORMATION FOR SEQ ID NO: 104:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 104:

GAAAAGGGAA AGAAAAACAG AACTTTGTGC ACTACAATTA TACTGTTATA AAAAACACTT        60

CCATAGATTA CATTAAGCAG AAACAAACCT TTCTTTCATG TGTTCTCCTC CAGGCCAAGC       120

TGTCTAAGGA CCGCAAAGGC TGTTGTCACT TGCAGGCTCC CAGATTAGGT CTGAAATAGG       180

ATTTCACCAG GTCATCCATT GTTAGTTAAA TCCTAGTAAA TNCA                        224

(2) INFORMATION FOR SEQ ID NO: 105:

(i) SEQUENCE CHARACTERISTICS:
        (A) LENGTH: 440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 105:

GGATCCGCCC TCCTCGGCCT CCCAAAGTGT TGGGATTACA GGCGTGAGCC ACCGCACCTG        60

GCTTTTTTTT TTTTTTTTTT TGGNGGAGAC AGAGTCTTAC TCTGTTGCCC AAGCTGGAGT       120

GCAGTGGTGC AATCTTGGTT CACTGCAACC TCCACCTCCA GAGTTCAAGC AATTCTCTGC       180

CTCAGTTTCT GGAGTAGCTG GGATTACAGG TGCCTGCCAT CACGCCTGGN TAAATTTGGG       240
```

```
ATTTTTTTTT AGTAGAGACA GGGTTTCANC ATGTTGGCCA GGNTGGTCTT GGACTCCTGA        300

CCTGGTGAAC CACCAGGCTC GGGCTCCAAA TTTGGTTGGG ATTACAGGGG GTNAANCAAC        360

CACAACCCAG NCTAAAGTTT TNAAAACATN CAAAGTGTTT TAAAATNATG NGATACGATT        420

TATTGTACAA TTAATTTTAT                                                    440
```

(2) INFORMATION FOR SEQ ID NO: 106:

(i) SEQUENCE CHARACTERISTICS:
        (A) LENGTH: 448 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 106:

```
GTCTTTCCCA TCTTCTCCAC AGAGTTTGTG CCTTACATTA TTACTCCTTG CCATTTTCAA         60

GAAAGCATTG TCAGCTCTTC CAATCTCCAT CACCTTTGGG CTTGTTTTCT ACTTTGCCAC        120

AGATTATCTT GTACAGCCTT TTATGGACCA ATTAGCATTC CATCAATTTT ATATCTAGCA        180

TATTTGCGGN TAGAATCCCA TGGATGTTTC TTCTTTGACT ATAACAAAAT CTGGGGAGGA        240

CAAAGGTGAT TTTCCTGTGT CCACATCTAA CAAAGTCAAG ATCCCCGGCT GGACTTTTGG        300

AGGTTCCTTC CAAGTCTTCC TGACCACCTT GCACTATTGG ACTTTGGNAA GGAGGTGCCT        360

ATAGAAAACG ATTTTGGAAC ATACTTCATC GCAGGGGAC TGTGTCCCCC GGTGGCAGAA         420

NCTACCAAGA TTTGCGGGNC GAGGTCAA                                           448
```

(2) INFORMATION FOR SEQ ID NO: 107:

(i) SEQUENCE CHARACTERISTICS:
        (A) LENGTH: 198 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 107:

```
GGATCCGCCC GCCTTGGCCT CCCAAAGTGC TGGGATTACA GGCATGAGCC ACCGCTCCTG         60

GCTGAGTCTG CGATTTCTTG CCAGCTCTAC CCAGTTGTGT CATCTTAAGC AAGTCACTGA        120

ACTTCTCTGG ATTCCCTTCT CCTTNAGTAA AATAAGNATG TTATCTGNCC GCCCTGCCTN        180

GGNNATTGNG ATAAGGAT                                                      198
```

(2) INFORMATION FOR SEQ ID NO: 108:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 108:

```
CTGCAGTGAG CCGTGATTGC ACCACTTTAC TCCAGCCTGG CAACAAAAT GAGACCCTGG          60

CTCAAAAACA AAACAAAAA CAAAAAAAGA GTAAATTAAT TTAAAGGGAA GTATTAAATA         120

AATAATAGCA CAGTTGATAT AGGTTATGGT AAAATTATAA AGGTGGGATA TTAATATCTA        180

ATGTTTGGGA GCCATCACAT TATTCTAAAT AATGTNTTGG TGAAAATTAT TGTACATCTT        240
```

```
TTAAAATCTG TGTAATTTTT TTTCAGGGAA GTGTTTAAAA CCTATAACGT TGCTGTGGAC      300

TACATTACTG TTGCACTCCT GATCTGGAAT TTTGGGTGTG GTGGGAATGA TTTCCATTCA      360

CTGGAAAGGT CCACTTCGAC TCCAGCAGGC ATATCTCATT ATGATTAGTG CCTCATGGNC      420

CTGGTGTTTA TCAAAGTACC TCCCTGAATG GACTGCGTGG GTCATCTTGG NTGTGATTCA      480

GTATATGGTA AAACCCAAGA                                                  500
```

(2) INFORMATION FOR SEQ ID NO: 109:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 109:

```
CTGCAGCCTT GACCTCCTGG GATCAATCGA TCCTCCCACC TCAGCCTCCT AAGTAGCTGG       60

AACTACAGGT GTGCACCACC ATGCCCGGCT AATNGNTGTA TTTTCTGTAG ATACGAGGTN      120

TNGCCATGTT GCCCAGGCTG GTCTTGAACT CTGGGCTTAG GTGATCTGCC CGCCTCAGCC      180

TCCCAAAGTG CTAAGATTAC AGGCATGAGC TACCATGCCC AGCCGAAATC TTCAAATGAA      240

AAAGTTACTA TAGCTAATTA ATGATTTACT GAAGAGTTAT GGGATGTACA CGTTACCATT      300

TTCTCTAAAT CAAGATAAAG AGATGAGGAA AGAAAACACT CCAGTGGGGC ATTCCTGTNA      360

CAAAACAAAT TATCAGTCTT GGGGTTTNAC CATATACTGA AATCACAGGC AAGATGAGCC      420

ACGCAGTCCA TNCAGGGAGG TACTGGATAA CACCAGGGNC ATGAGGGACT AATCATAATG      480

AGATATGCTG CTGGAGTCGA                                                  500
```

(2) INFORMATION FOR SEQ ID NO: 110:

(i) SEQUENCE CHARACTERISTICS:
        (A) LENGTH: 550 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 110:

```
CTGCAGGATG AGAGCGATCT CTTNTTNCAT TTCCTGCGCT ACGCGCTGCG GGCGACCAAA       60

TTCTTTCGCC ATAATAAATT CTCCTGACNA AAAAGGGGCT GTTAGCCCCT TTTTAAAATT      120

AATTTCAGGT GGAAGGGCTG TTCACGTTGA CCTGATAAGA CGCGCCAGCG TCACATCAGG      180

CAATCCATGC CGGATGCAGC GTAAACGCCT TATCCCGCAT GGAACCCTAA AAACCTTAAG      240

CAATGGTACG TTGGATCTCG ATGATTTCGA ATACTTCGAT CACATCGNCA GTGCGGACGT      300

CGTTGTAGTT CTTAACGCCG ATACCACATT CCATACCGTT ACGGGACTTC GTTAACGTCA      360

TCTTTGGAAG CGGGGCAGGG ACTCCAGCTC GNCTTCGTAG ATAACCACGT TGGCACGCAG      420

GAACGCGGGT CGGGTTGTGA CGTTTAACAC AACTTCCGGG TAACCATACA GGCTGNGATG      480

GNACCAAATT TCGGGGGATT TGGACAAGTC AAGAACTTCC CGCCAGACCG ATAATCTTGT      540

TGTTCAGTTC                                                             550
```

(2) INFORMATION FOR SEQ ID NO: 111:

(i) SEQUENCE CHARACTERISTICS:

(A) LENGTH: 541 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 111:

CTGCAGCTTT CCTTTAAACT AGGAAGACTT GTTCCTATAC CCAGTAACG ATACACTGTA    60

CACTAAGCAA ATAGCAGTCA AACCCAAATG AAATTTNTAC AGATGTTCTG TGTCATTTTA   120

TNTTGTTTAT GTTGTCTCCC CCACCCCCAC CAGTTCACCT GCCATTTATT TCATATTCAT   180

TCAACGTCTN NNTGTGTAAA AAGAGACAAA AAACATTAAA CTTTTTTCCT TCGTTAATTC   240

CTCCCTACCA CCCATTTACA AGTTTAGCCC ATACATTTTA TTAGATGTCT TTTATGTTTT   300

TCTTTTNCTA GATTTAGTGG CTGNGTTGTG TCCGAAAGGT CCACTTCGTA TTGCTGGTTG   360

AAACAGCTCA GGAGAGAAAT GAAACGCTTT TTCCAGCTCT CATTTACTCC TGTAAGTATT   420

TGGAGAATGA TATTGAATTA GTAATCAGNG TAGAATTTAT CGGGAACTTG AAGANATGTN   480

ACTATGGCAA TTTCANGGNA CTTGTCTCAT CTTAAATGAN AGNATCCCTG GACTCCTGNA   540

G                                                                  541

(2) INFORMATION FOR SEQ ID NO: 112:

(i) SEQUENCE CHARACTERISTICS:
        (A) LENGTH: 241 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 112:

NNCCCNCNCN NNNNNNNTTN NTNTTGCCCG ATAACTATAG GGNGACTTGG AGATCCACCG    60

CGGTGGCGGN CGNTCTAGAA CTAGTGGATC CCCCGGGNTG CAGGACCCAA CGCTGCCCGA   120

GATGCGCCGC GTGCGGTTGC TGGAGATGGC GGACGCGATG GATATGTTCT GCCAAGGGTT   180

GGTTTGCGCA TTCACAGTTC TCCGCAAGAA TTGATTGGCT CCAATTCTTG GAGTGGTGAA   240

T                                                                  241

(2) INFORMATION FOR SEQ ID NO: 113:

(i) SEQUENCE CHARACTERISTICS:
        (A) LENGTH: 834 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 113:

CCCCCCCNCC NNNNNTTTTN NGCAGCCCGT AATTACCCTC ACTNCCGGGA ACAAAAGCTG    60

GGTACCGGGC CCCCCCTCGA GGTCGACGGT ATCGATAAGC TTGATATCGA ATTCCTGCAG   120

TGTTTAAAAA ATAAAATAAA CTAAAAGTTT ATTTATGAGG AGTACACTGC TTTCTTGTAA   180

ACACATGTAC AAGCCATATA ATAGAGTTCA TTTTTTACCC TAGTTACGGA AACACTAGAA   240

AGTCTTCACC CGGCCAAGAT AACACATCTT TAGTAAAAAT AGCAAGAAAT ATTTTATGGG   300

TTGTTTACTT AAATCATAGT TTTCAGGTTG GGCACAGTGG NTCATGCCTG TAATCCCAGC   360

ACTTTATGCG GNTGAGGCAG GCAGATCAGT TGAGGTCAGA AGTTTGGAGA CCAGNCTGGG   420

```
CAATGTGGNA AAACCTCATC TCCACTAAAA ATACAAAAAT TAGNCAGGCA TGGTGGTGCA      480

CACATGTAAT TCCAGNTACT TGGGGAGGCT GAGACAGGAG GATCGNTTGA ACCTAGGGAG      540

GGAGGAGTTG GAGTGAGCTA ATGTCAATGC ACTCTTGGTT GGGGCGANAG AGCAAGATCT      600

TTCTTCCAAA AAAAAAAAAA AAAAAAAGC CAGGTGNGGN GGTCAAGGCT GTAATCCAGA       660

ATTNGGGAGG CCGNGGAGGN NATCANTGNG GNAGGNGTCA AGNGGGGCNG GCCACATGGG      720

GAACCCGTTN TTNTTAAATN AAAATTAGCC GGGGNGGGGG AGGACTNTAT CCNGTTCCGG      780

NGGTGNGGAG GATCNTTATT NTGGNGGAGG GTGGATGNNC CAGTTGACNC CCCC            834

(2) INFORMATION FOR SEQ ID NO: 114:

(i) SEQUENCE CHARACTERISTICS:
        (A) LENGTH: 838 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 114:

TTGGGCNCNC GCCCCTTAAN TTTTTATNGN TTNCTANAAA AANANNNGGC NCNNTAAAAT       60

ATATTTTTTN TTGTGACCCC TTTTAAAAGG GACCCNCTAA AAAATTTTNT GGTTNNTTTN      120

GATTTANGTG GGTGNTTTTN TTATATTTTT GGNGAGNNTC TGTAGTCNTC NCCCTCAAAC      180

ANNTCNTACN ATNGGNANCG TGACTCTGTC NTTNGTNANN NTCGNTNTCN NGTNATTCNA      240

GGNNCCTCGC GCNNCNCGGG CNNNGTTTTT TTTNNCNNTT TTTAAGCCNA ANNCTCAGTA      300

NCNTCCAACG GNGCTNNGAC ANNNGNNNCT NTCGNGGGTN CCCTCTNTNT NGNNCNNGGC      360

TNNNGNNNNC NGNCNGCNGN GCCNTGCGNN NNGNNNGNGG NNNGNTNNCA TANGGATNGN      420

GNTGCTCNNC NCNNGNGTNN TNAGTAGGNA NTTTTNTNNT ACTTGCCNNC NNNTNGCTGC      480

GAGNANAGCN ANNTNGNNGN AGNGNNGNTG CGCGGANNTT CCCCTGATNA NCTCGAGCNG      540

NTTACNGGNG CNNCCTNGAA NAAGNGNNGT ANNGTGCCGA GNCGCTANNC TGAGCCTGAG      600

TNTCGACNGG NATNGTGNNT CNTACNGTTA NGGGNNGCNN GANCGGGNTG ANTCNCCGGN      660

NGANCNAGCG ACTGCCTNTC ANGCGAANCG TNTCANGNNN GTAGAGCANA GGGTNANNNG      720

TCNNNNAAGC NTNNAGTGAN TGTCNTNACN NGTGANTTAC GGCNTAGNCT TGATNTNNAN      780

NCGAGGNNNN ATNNANNNTT GGANANTTNN TNNNNTCNCN TCGCGGNGNG NCNNGCCG        838

(2) INFORMATION FOR SEQ ID NO: 115:

(i) SEQUENCE CHARACTERISTICS:
        (A) LENGTH: 803 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 115:

ATTCGCGCGT AGCCCGATAA CTATAGGGCG ACNTGGAGNT CCACCGCGGT GGCGGCCGCT       60

CTAGNAACTA GTGGATCCCC CGGGCTGCAG GAATTCACGG ACTAATCCTC TACAGATCTT      120

GCTGGAGTGG CCTTTCAGCC TTTTGTGACT GTTTGTAGTG AAATGTACAC ACAAGCCTAC      180

AAGGCAGCCC AGATGTACCA TAACTGTGGG AAAATTAAAA AAAAAAAAAC ACAGAACCTC      240

TCTATGTTGC CCATGCTGGA CTCAAACTCT TAGACAAGCA ATCCTCGTAC CTCAGCCTCC      300

TGAGTTCCTG AGTAGCTGGG ACTACAAGCA TGCACCACCA TGCCAGGCTA TGAGAAAGTT      360
```

```
CTTTTTATTG ATCCAGACCT TATTGCCTGG TAACTTCCAC CACTGTTCCT AGCTCTGNTC      420

TCTGGTCCTA ACAGAGGAAA ATCTTGACCC CACACCTAGT GCAACTGGAT AGCTTATNGT      480

TGGGCTNGTG TTTCCTCTAT TCTGGGTCCA CCCTAAAATC CNATAGATAC TCCAACTGCT      540

CANAGNAAAC CAAGCTCTCT CTCTNNCTTN CTTTCTTNNN CTCTATTNAT TNATGGGNNA      600

TNATTNATTN NGGGGATGGN GTTCGGTCGC CGCCCGGCTG GNGTGAAATG GGGGAGGCAA      660

TCAATTTAAC CCCACCCNGG GTCCAGGGAT CTCGTTNAAA CCGNNNNNNN NNNNNNNNNA      720

NGNNCNNCNC NNNCCNNTNN NNNGGTTTNN NNGNNNNGGG NNNCCNNNNN NANNNNNNTN      780

NNNCCNCCNA NNNTNCNNNN CCC                                             803
```

(2) INFORMATION FOR SEQ ID NO: 116:

(i) SEQUENCE CHARACTERISTICS:
        (A) LENGTH: 780 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 116:

```
CNNNNNNNCC CNNTNATTNT ACGCCAGCCG CGTAATTAAC CCTCACTAAA GGGAACAAAA       60

GCTGGGTACC GGGCCCCCCC TCGAGGTCGA CGGTATCGAT AAGCTTGATA TCGAATTCCA      120

ACTCCTCACT TGCCAGATGT GACCTTAAGC AAGTGAACTT CTGTGTGCCA CACTGTTTTC      180

ATCTGTAAAA GGATAAAGGG AATATCATAA ATTAGNTTGT TAAGCCTTAG TTTAATAATG      240

TCTCTAAGTT TTACATATAA GTAGACAGTG TCTTTCTTGT TTAGTGAATA ATCATTCTTA      300

TTATTTAATA GTATCTCTAC TAAATTTATT GTGTAAGATT ATACTAATCT TGTTTAGTGC      360

GTGGTAATCA CTTCTGCTCA TATTTAACCT ATAAGCATAA TATAGTTTAT TTATATACCA      420

NTTATTTATT TTATTTTATT TGNNGAGATG CAGCTTGTCT TTTNCAACCC AGGGNTGNGG      480

NGNAGNNGNG NAANCTTGNT TCACTGNAAC CNCCACCNCC CAGGTNCAAG NGATTCTCCT      540

GNTCAAGCCN CCTNAGNAGN TGGNATTACA GNACGANTAC ANNCCAGNTA NNNNGGNTNT      600

NNGNTNGNNA GGNNNCACAN NNGNCAGGTN NNTCGNCTCC NNGCCANTNA CTNNNNCCAN      660

CCCCNNNGNN NNNNATANAG NATNANCANN NNCCNCNNNN NCNNNNNNNG GNGGANNCCN      720

NNTNGCNGNN ANNGNNANNN NNTNNNNNNN NNGGNCNNNG NNNNNNNNCC NNNNNNCCCC      780
```

(2) INFORMATION FOR SEQ ID NO: 117:

(i) SEQUENCE CHARACTERISTICS:
        (A) LENGTH: 803 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 117:

```
NNNNNNNNNC CNNNNNNTTC GNNCGTAACN CGANTCACTA TAGGGCGACT TGGAGCTCCA       60

CCGCGGTGGC GGCCGCTCTA GAACTAGTGG ATCCCCCGGG CTGCAGGAAT TCGATATCAA      120

GCTTTNGTGT GTAAAAAGTA TTAGAATCTC ATGTTTTTGA ACAAGGTTGG CAGTGGGTTG      180

GGAGGAGGGA TTGGAGATTG ATGCGATAGG AATGTGAAGG GATAGCTTGG GGTGGATTTT      240

ATTTTTTAAT TTTAATTTTT ATTTNTTGAG ATGGAGTCTT GCTCTGTCTC CCAGGCTGGA      300
```

```
GTGCAGTGGT GTGATCTCAG CTCACGGGTT CAAGCGATTC TCCTGCTGCA GCCTCCCGAG    360

TAGCTGGGAT TACAGGAGCG CGCCACCACA CCCGGNTAAT TTNNTTGTAT TTTTAGTAGA    420

GACGGGGTTT CACCATGTTG GTTAGGCTGG TCTAGAACTC CCAACCTCAT GATCCGCCTG    480

CTTCGGCCTC CCAAAGTGCC GGAATTACAG GCGTGAGCGA CTGCACCCGG CCGCTTGGGG    540

GTGGATTTTT AAAGAAATTT AGAAGAATGT AACTTGGCCA GATACCATGT ACCCGTTAAT    600

TCATTTNCGG TTTTTTGGAT ACCCATTTTG NNATTCTCCC NCCACTGGAT AAATAAGGGN    660

GGTTCATTNT NGNTTAGTTT GGGTNTTTTT NAGTGTGGNT TCTGCTTATN ATTAGAATGG    720

NCTNCTTTNC CAANCTGGAA AGGGAGGAGT TAAAATCANT ACCAGAANCA GAAATTCTTT    780

TCANTTGTTG CNCNAGAAAT GCC                                           803

(2) INFORMATION FOR SEQ ID NO: 118:

(i) SEQUENCE CHARACTERISTICS:
        (A) LENGTH: 819 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 118:

TNCCNNNNCN NNNNNAATTT TNGCAGNCGC GTAATTAACC TCACTAAAGG GAACAAAAGC     60

TGGGTACCGG GCCCCCCCTC GAGGTCGACG GTATCGATAA GCTTCCCTCC CCTTCCTCAG    120

CTCTGGCGAC CCTGCGCTGT GGTGGTTCTC CAACCACACT CATTCTCCTC AGCTGGCTCC    180

TTGCTCTTCT TCCACCCCCT CGTTGGAAGT GTTCCTAAGT GTTTGGCTTG GCCTCCTCTT    240

CCCCTTCCTT AGNTTAGACT TCTCCACTGC TCCAACATCA ACTGGAAATC TATGGAATTG    300

ATTCCTGTTT TCAGCTCCAG TCCTGTTCAC AGGGCATTTT CACCTGCTGG CACTTCCAAA    360

GTGACACTTC CAAACCACTT CCTCGCCCTC CTCTCTAAAC CAGGTCTTTC TTCCTAACTT    420

CCTTATTTCT GAGAATGTCT CTGNCATGTT CTAAACTGAA AACTCCTAGT CAACTNCACA    480

CTTTATTCCC TGGATCCTCA ATTGGGTTCC CATGTNCCGT TAGTGTTTCT TGGTAAGNCT    540

CTGCCANCAC CGNAGGATCG ACTCTAATCA CATCTCAACT GAATTATGGN AAAGTCAACT    600

CAATTCTCTC AACCATCCCA GGCTCCACTA TGGNTAATAT GCTAAGGAGA GCTGACCCAA    660

CGGGGAGAAG ATCTGNGGGG GAGGAGAGAA ACAAAGNTAA TGGAATNATT CTCGAAAAGC    720

CCACAAGGNG AAGGATAACC CNCTTCCNCT CGAAAGAGGG GGGATCGCCA GATNTCGCGC    780

CCGGAAAGAA ACCGGGGNGA GGGGGTTACA NTGTAAGNC                          819

(2) INFORMATION FOR SEQ ID NO: 119:

(i) SEQUENCE CHARACTERISTICS:
        (A) LENGTH: 796 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 119:

TNTTGGCTGG TACTGCTTGA GCAACTGGTG AAACTCCGCG CCTCACGCCC CGGGTGTGTC     60

CTTGTCCAGG GGCGACGAGC ATTCTGGGCA AGTCCGCAC GCCTCTTGTT CGAGGCGGAA     120

GACGGGGTCT GATGCTTTCT CCTTGGTCGG GACTGTCTCG AGGCATGCAT GTCCAGTGAC    180

TCTTGTGTTT GCTGCTGCTT CCCTCTCAGA TTCTTCTCAC CGTTGTGGTC AGCTCTGCTT    240
```

```
TAGGCATATT AATCCATAGT GGAGGCTGGG ATGGGTGAGA GAATTGAGGT GACTTTTCCA      300

TAATTCAGGT GAGATGTGAT TAGAGTTCGA TCTGCGGTGG TGGCAGAGGC TTACAAGAAA      360

CACTAACGGG ACATGGGAAC CAATTGAGGA TCAGGGAATA AAGTGTGAAG TTGACTAGGA      420

GGTTTTCAGT TTAGAACATG GCAGAGACAT TCTCAGAAAT AAGGAAGTTA GGAAGAAAGA      480

CTGGTTTAGA GAGGAGGGCG ANGAAGTGGT TTGGGAAGTG TCACTTTGGG AAGTGCCAGC      540

AGGTGAAAAT GCCTGTGACA GGATGGAGCT GAAAACAGGA TCAATTCCAT AGATTCCAGT      600

TGATGTNGGA GCAGGGGAGA AGTCTTAGCT AAGGAAGGGG AAGAGGAGGC CAAGGNAACA      660

CTTAGGACAA TTGNAACGAN GGGGGGGGAG AAGAGNAAGG GCCACTTAGG GGAATAATNT      720

GGTGGGGGAC CCCCAAGNNA GGGCGCANNN TTAGGAGGGG GGGANNTCAN AGGAAAGTGG      780

AAGNTTGGGT TTANCT                                                     796

(2) INFORMATION FOR SEQ ID NO: 120:

(i) SEQUENCE CHARACTERISTICS:
        (A) LENGTH: 802 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 120:

ATTCGTCGTA NCCCGATNAC TATAGGGCGA CTTGGAGCTC CACCGCGGTG GCGGNCGCGG       60

GCAGGGNCCG GNCCTTTGTG GCCGCCCGGG CCGCGAAGCC GGTGTCCTAA AAGATGAGGG      120

GCGGGGCGCG GNCGGTTGGG GCTGGGGAAC CCCGTGTGGG AAACCAGGAG GGGCGGCCCG      180

TTTCTCGGGC TTCGGGCGCG GCCGGGTGGA GAGAGATTCC GGGGAGCCTT GGTCCGGAAA      240

TGCTGTTTGC TCGAAGACGT CTCAGGGCGC AGGTGCCTTG GGCGGGATT AGTAGCCGTC       300

TGAACTGGAG TGGAGTAGGA GAAAGAGGAA GCGTCTTGGG CTGGGTCTGC TTGAGCAACT      360

GGTGAAACTC CGCGCCTCAC GCCCCGGGTG TGTCCTTGTC CAGGGGCGAC GAGCATTCTG      420

GGCGAAGTCC GCACGCCTCT TGTTCGAGGC GGAAGACGGG GTCTTGATGC TTTCTCCTTG      480

GGTCGGGGAC TGTCTCGAGG CATGCATGTC CAGTGACTCT TGTGTTTGGT GNTGCTTCCC      540

TCTCAGATCT TCTCACCGNG GTGGGCAACT CTGTTTAGGC ATATTATCCA TAGNGGAGGC      600

TGGATGGTTG AAANAATTGA GGTNATTTTC CATAATCAAG TGAAATTTGA TAGAGTCCGN      660

CTTTNGGGGT GNAAGGGTTA AAAAAAAATA ACGGAAATGG AACAATGAGG TCAAGGATTA      720

GTTGAGTTGN TAGNGGTTCA ATTAGANATG AAGGNATCTA AAATAGGAGT AGAGAANNNG      780

TTNAAAGAGG GAAAATTTTG CC                                              802

(2) INFORMATION FOR SEQ ID NO: 121:

(i) SEQUENCE CHARACTERISTICS:
        (A) LENGTH: 793 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 121:

ATATGCAGCC GCGTAATTAA CCTCACTAAA GGGAACAAAA GCTGGGTACC GGGCCCCCCC       60

TCGAGGTCGA CGGTATCGAT AAGCTTGATA TCGAATTCCT GCAGCCCGGG GGATCCGCCC      120
```

```
CGCGGCCTCC CAAAGTGCTG GGATTACAGG CGTGAGCCAC CGCCCCGGGN CTCACATTTT      180

ATTTCTATTG GCTAGCGCTG CTCTAAATCT TCTGTTCCTT CTGCTACACC AGGCCTAACA      240

CTCAAAATCC CTGCCAACCT TTTCCTTCCT GAAGCTTCCC TCCCCTTCCT CAGCTCTGGC      300

GACCCTGCGC TGTGGTGGTT CTCCAACCAC ACTCATTCTC CTCAGCTGGC TCCTTGCTCT      360

TCTTCCACCC CCTCGNTGGA AGTGTTCCTA AGTGTTTGGC TTGGCCTCCT CTTCCCCTTC      420

CTTAGCTTAG ACTTCTCCAC TGCTCCAACA TCAACTGGAA ATCTATGGAA TTGATTCCTG      480

TTTCAGCTCC AGTCCTGTTC ACAGGGGATT TTCANCTGGT GGCATTTCCA AAGTGAAATT      540

CCAAACCACT TCCTCGGCCT CCTCTTCTAA ANCAGGTCTT TCTTCCTAAC TTCCTTATTC      600

TTGAGAATGT CTCTGCATGT TCTTAAANTG AAAACTCCTA GTCAAATTCA AATTTATCCC      660

TGATCCCAAA TGGTCCCATT CCCGTAGGGT TTNTGTAGCC TGCACACCGA GGTCGGANTT      720

TATNNATTCA CCGATTATGG AAAGTAACCA ATCTTNACCA NCCAGCTCAT TTGTTNTNTG      780

CTAAGAGGGT NCC                                                        793

(2) INFORMATION FOR SEQ ID NO: 122:

(i) SEQUENCE CHARACTERISTICS:
        (A) LENGTH: 440 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 122:

AAAGTCATGG ATTCCTTTAG GTAGCTACAT TATCAACCTT TTTGAGAATA AAATGAATTG       60

AGAGTGTTAC AGTCTAATTC TATATCACAT GTAACTTTTA TTTGGATATA TCAGTAATAG      120

TGCTTTTTCN TTTTTTTTTT TTNTTTTTTT TNNTTTTNGG GGANAGAGTC TCGCTCTGTC      180

GCCAGGTTGG AGTGCAATGG TGCGATCTTG GCTCACTGAA AGCTCCACCN CCCGGGTTCA      240

AGTGATTCTC CTGCCTCAGC CNCCCAAGTA GNTGGGACTA CAGGGGTGCG CCACCACGCC      300

TGGGATAATT TTGGGNTTTT TAGTAGAGAT GGCGTTTCAC CANCTTGGNG CAGGCTGGTC      360

TTGGAACTCC TGANATCATG ATCTGCCTGC CTTAGCCTCC CCAAAGTGCT GGGATTNCAG      420

GGGTGAGCCA CTGTTCCTGG                                                 440

(2) INFORMATION FOR SEQ ID NO: 123:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 123:

CTTAGTCTGT NTCGTAGTCA TATTAATTGT AAGTNTACAC TAATAAGAAT GTGTCAGAGC       60

TCTTAATGTC AAAACTTTGA TTACACAGTC CCTTTAAGGC AGTTCTGTTT TAACCCCAGG      120

TGGGTTAAAT ATTCCAGCTA TCTGAGGAGC TTTTNGATAA TTGGACCTCA CCTTAGTAGT      180

TCTCTACCCT GGCCACACAT TAGAATCACT TGGGAGCTTT TAAAACTGTA AGCTCTGCCC      240

TGAGATATTC TTACTCAATT TAATTGTGTA GTTTTTAAAA TTCCCAGGA AATTCTGGTA       300

TTTCTGTTTA GGAACCGCTG CCTCAAGCCT AGCAGNACAG ATATGTAGGA AATTAGCTCT      360

GTAAGGTTGG TCTTACAGGG GATAAACAGA TCCTTCCTTA GNCCCTGGGA CTTAATCACT      420
```

```
GAGAGTTTGG GTGGNGGTTT NGNATTTAAT GAC                                  453

(2) INFORMATION FOR SEQ ID NO: 124:

(i) SEQUENCE CHARACTERISTICS:
        (A) LENGTH: 369 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 124:

GACACACATT CACACATAAT TATGAAAGCA TTTTCAGGCA AAACTCAATC ACAAGTCTGG       60

GTTTTTAACA TAGTTAACTG AATATTTCCC TTGGGGGGTT AAATTTTAGA ACAGACGTNC      120

ATNCAATCTG GAAGAAGAGC TATGAAAAAA ACCTAGCTTG GGTNGGTTTC ATAGGGTNCA      180

TTATGNACAC ATTGTTATTT TATCCCTTAA TNCTAGTAAA GAAATAGAAT CTGAAAATAA      240

GTAAAACTAC TTGGAAAAAA NTTAAAAGAT ACAGAAATTT CTATCTTAAA TGATGTGTGG      300

GCCNCTGTGA TTTTAGTNGG GNTGGTTAAA ANCCCAGAGG TGAAGAGNAT NCTCTATGCT      360

GTGNGGGGG                                                             369

(2) INFORMATION FOR SEQ ID NO: 125:

(i) SEQUENCE CHARACTERISTICS:
        (A) LENGTH: 516 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 125:

GCTCATCATG CTTCACGGGG GAGGCTGTGC GGGAAGAATG CTCCCACACA GNATAAAGAA       60

TGCTCCCGCA CAGGATAGAG AATGCCCCCG CACAGCATAG AGAAGCCCCC GCACAGCATA      120

GAGAATGCCC CCNCACAGCA TAGAGAAGCC CCCGCACAGC ATAGAGAATG CTCTTCACCT      180

CTGGGTTTTT AACCAGCCAA ACTAAAATCA CAGAGGSCMA CACATCATTT AAGATAGAAA      240

TTTCTGTATC TTTTAATTTY TTTCMAAGTA GTTTTACTTA TTTTCAGATT CTATTTCTTT      300

ACTAGAATTA AGGGATAAAA TAACAATGTG TGCATAATGA ACCCTATGAA ACMAACMMAA      360

GCTAGGTTTT TTTCATAGST CTTCTTCCAG ATTGAATGAA CGTCTGTTCT AAAATTTAAC      420

CCCCCAGGGA AATATTCAGT TAACTATGTT AAAAACCCAG ACTTGTGATT GAGTTTTGCC      480

TGAAAATGCT TCATAATTA TGTGTGAATG TGTGTC                                516

(2) INFORMATION FOR SEQ ID NO: 126:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 126:

GTATAATGCA GGTGCTATAA GGTGAGCATG AGACACAGAT CTTTGCTTTC CACCCTGTTC       60

TTCTTATGGT TGGGTATTCT TGTCACAGTA ACTTAACTGA TCTAGGAAAG AAAAAATGTT      120

T                                                                     121
```

(2) INFORMATION FOR SEQ ID NO: 127:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 127:

TGGAGACTGG AACACAAC                                                 18

(2) INFORMATION FOR SEQ ID NO: 128:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 128:

GTGTGGCCAG GGTAGAGAAC T                                             21

(2) INFORMATION FOR SEQ ID NO: 129:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 129:

ATCTCCGGCA GGCATATCT                                                19

(2) INFORMATION FOR SEQ ID NO: 130:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 130:

TGAAATCACA GCCAAGATGA G                                             21

(2) INFORMATION FOR SEQ ID NO: 131:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 131:

CCATAGCCTG TTTCGTAGC                                                19

(2) INFORMATION FOR SEQ ID NO: 132:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 132:

CCATAGCCTA TTTCGTAGC                                       19

(2) INFORMATION FOR SEQ ID NO: 133:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 133:

TCACAGAAGA TACCGAGACT                                      20

(2) INFORMATION FOR SEQ ID NO: 134:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 134:

TCTGTACTTT TTAAGGGTTG TG                                   22

(2) INFORMATION FOR SEQ ID NO: 135:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 135:

GACTCCAGCA GGCATATCT                                       19

(2) INFORMATION FOR SEQ ID NO: 136:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 136:

GATGAGACAA GTNCCNTGAA                                      20

(2) INFORMATION FOR SEQ ID NO: 137:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO: 137:

TTAGTGGCTG TTTNGTGTCC                                               20

(2) INFORMATION FOR SEQ ID NO: 138:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 138:

GTGTGGCCAG GGTAGAGAAC T                                             21

(2) INFORMATION FOR SEQ ID NO: 139:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 139:

CCCAACCATA AGAAGAACAG                                               20

(2) INFORMATION FOR SEQ ID NO: 140:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 140:

ACTTCAGAGT AATTCATCAN CA                                            22

(2) INFORMATION FOR SEQ ID NO: 141:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 141:

TGAAATCACA GCCAAGATGA G                                             21

(2) INFORMATION FOR SEQ ID NO: 142:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 142:

CACCCATTTA CAAGTTTAGC                                           20

(2) INFORMATION FOR SEQ ID NO: 143:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 143:

TGGAGACTGG AACACAAC                                             18

(2) INFORMATION FOR SEQ ID NO: 144:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 144:

CCATAGCCTG TTTCGTAGC                                            19

(2) INFORMATION FOR SEQ ID NO: 145:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 145:

CCATAGCCTA TTTCGTAGC                                            19

(2) INFORMATION FOR SEQ ID NO: 146:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 146:

GTTGTCATGA CTATC                                                15

(2) INFORMATION FOR SEQ ID NO: 147:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 147:

GTTGTCMTGA CTATC                                                15

(2) INFORMATION FOR SEQ ID NO: 148:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 148:

GTCATCCATG CCTGG                                        15

(2) INFORMATION FOR SEQ ID NO: 149:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 149:

GTCATCCRTG CCTGG                                        15

(2) INFORMATION FOR SEQ ID NO: 150:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 150:

GAGCCACGCA GTCCA                                        15

(2) INFORMATION FOR SEQ ID NO: 151:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 151:

GAGCCACKCA GTCCA                                        15

(2) INFORMATION FOR SEQ ID NO: 152:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 152:

CCAGCTCTCA TTTAC                                        15

(2) INFORMATION FOR SEQ ID NO: 153:

(i) SEQUENCE CHARACTERISTICS:

-continued

```
         (A) LENGTH: 15 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO: 153:

CCAGCTSTCA TTTAC                                                          15

(2) INFORMATION FOR SEQ ID NO: 154:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO: 154:

ATAGCCTGTT TCGTA                                                          15

(2) INFORMATION FOR SEQ ID NO: 155:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO: 155:

ATAGCCTRTT TCGTA                                                          15
```